(12) United States Patent
Gabra

(10) Patent No.: US 11,857,624 B2
(45) Date of Patent: Jan. 2, 2024

(54) CANCER THERAPEUTIC METHODS UTILIZING OPCML FRAGMENT

(71) Applicant: Hani Gabra, London (GB)

(72) Inventor: Hani Gabra, London (GB)

(73) Assignee: PAPYRUS THERAPEUTICS, INC., West Chester, PA (US)

( * ) Notice: Subject to any disclaimer, the term of this patent is extended or adjusted under 35 U.S.C. 154(b) by 588 days.

(21) Appl. No.: 16/882,362

(22) Filed: May 22, 2020

(65) Prior Publication Data

US 2020/0353080 A1  Nov. 12, 2020

Related U.S. Application Data

(63) Continuation of application No. 15/481,018, filed on Apr. 6, 2017, now Pat. No. 10,660,955, which is a continuation of application No. 13/639,643, filed as application No. PCT/GB2011/050754 on Apr. 15, 2011, now Pat. No. 9,649,378.

(60) Provisional application No. 61/325,013, filed on Apr. 16, 2010.

(30) Foreign Application Priority Data

Apr. 1, 2011  (GB) .................................... 1105584

(51) Int. Cl.

| A61K 39/395 | (2006.01) |
|---|---|
| A61K 31/506 | (2006.01) |
| A61K 38/17 | (2006.01) |
| A61K 45/06 | (2006.01) |
| C07K 16/28 | (2006.01) |
| C07K 16/32 | (2006.01) |
| C12Q 1/6886 | (2018.01) |
| A61K 31/404 | (2006.01) |
| A61K 31/555 | (2006.01) |
| A61K 31/7064 | (2006.01) |
| A61K 31/517 | (2006.01) |

(52) U.S. Cl.
CPC ...... *A61K 39/39558* (2013.01); *A61K 31/404* (2013.01); *A61K 31/506* (2013.01); *A61K 31/517* (2013.01); *A61K 31/555* (2013.01); *A61K 31/7064* (2013.01); *A61K 38/1774* (2013.01); *A61K 45/06* (2013.01); *C07K 16/28* (2013.01); *C07K 16/2863* (2013.01); *C07K 16/32* (2013.01); *C12Q 1/6886* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2004/0241682 A1 * 12/2004 Sellar ...................... A61P 35/00
435/6.12

* cited by examiner

*Primary Examiner* — Misook Yu
*Assistant Examiner* — Sarah A Alsomairy
(74) *Attorney, Agent, or Firm* — GORMAN IP LAW, APC

(57) ABSTRACT

A method of treating a patient having a cancer in which HER2, HER4, FGFR1, EPHA2 and/or FGFR3 is upregulated and/or in which HER2, HER4, FGFR1, EPHA2 and/or FGFR3 mediated-signaling is upregulated, the method comprising administering to the patient a compound comprising or consisting of an OPCML polypeptide (SEQ ID NO: 1), or a fragment thereof which comprises at least one Ig domain of OPCML, or a variant thereof having at least 90% sequence identity with the OPCML polypeptide or the fragment thereof, or a nucleic acid molecule which encodes the OPCML polypeptide or fragment or variant thereof.

20 Claims, 48 Drawing Sheets

Specification includes a Sequence Listing.

FIGURE 1
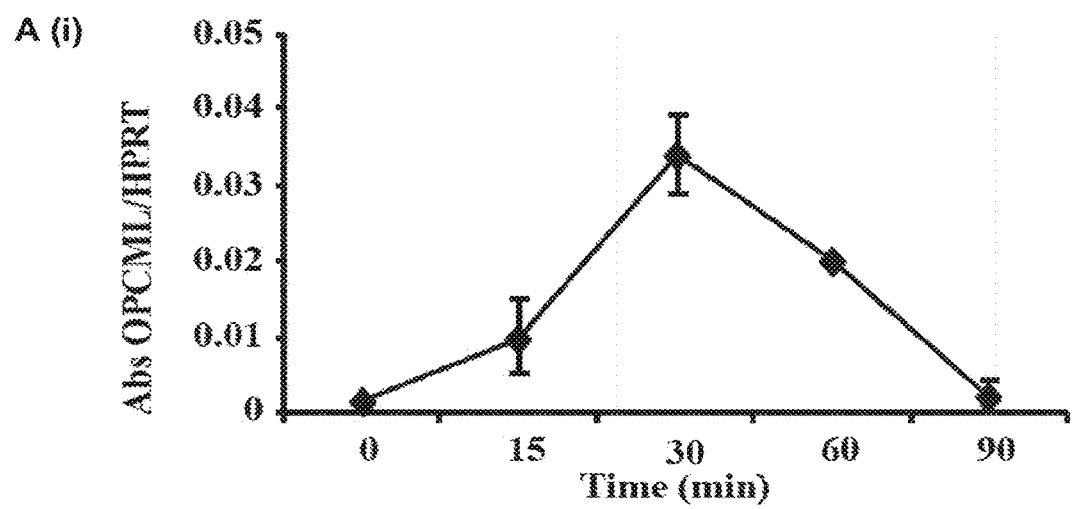
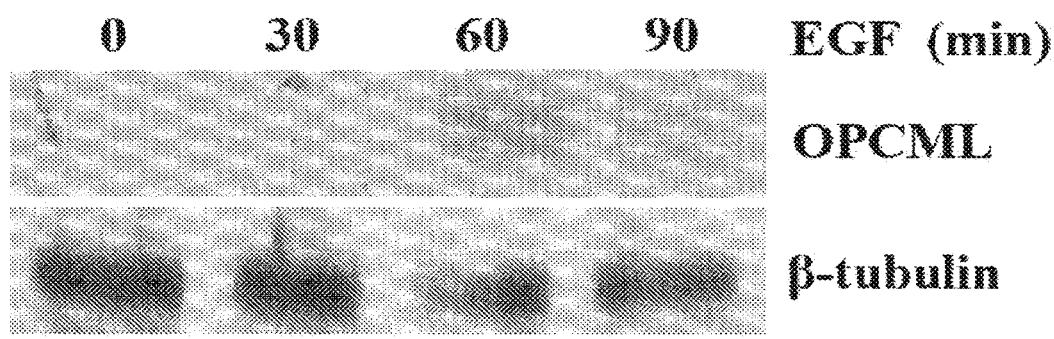

FIGURE 1 Continued
B (i)
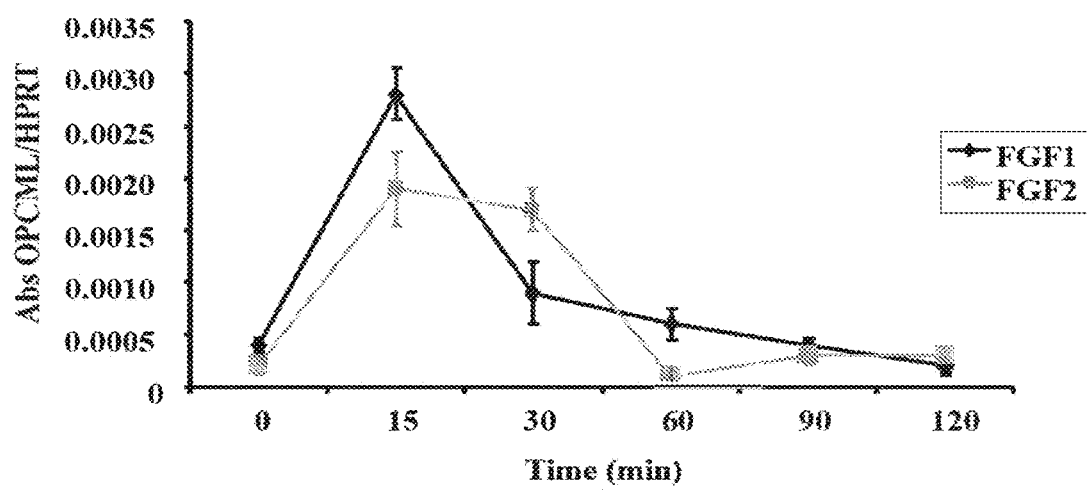
B (ii)
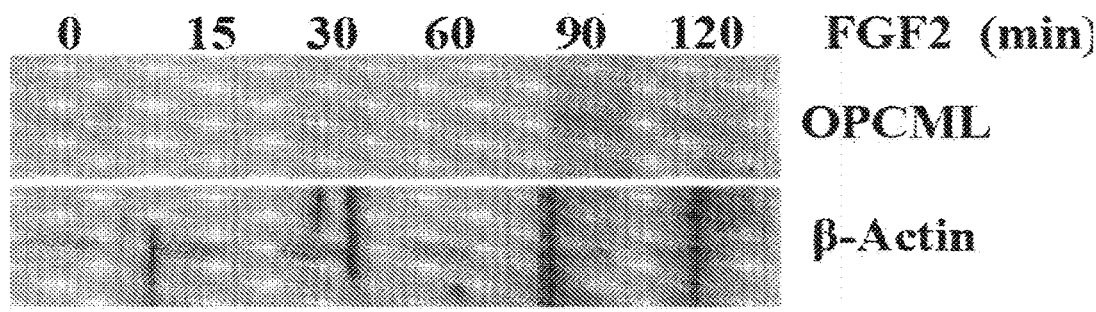

FIGURE 2
A (i)
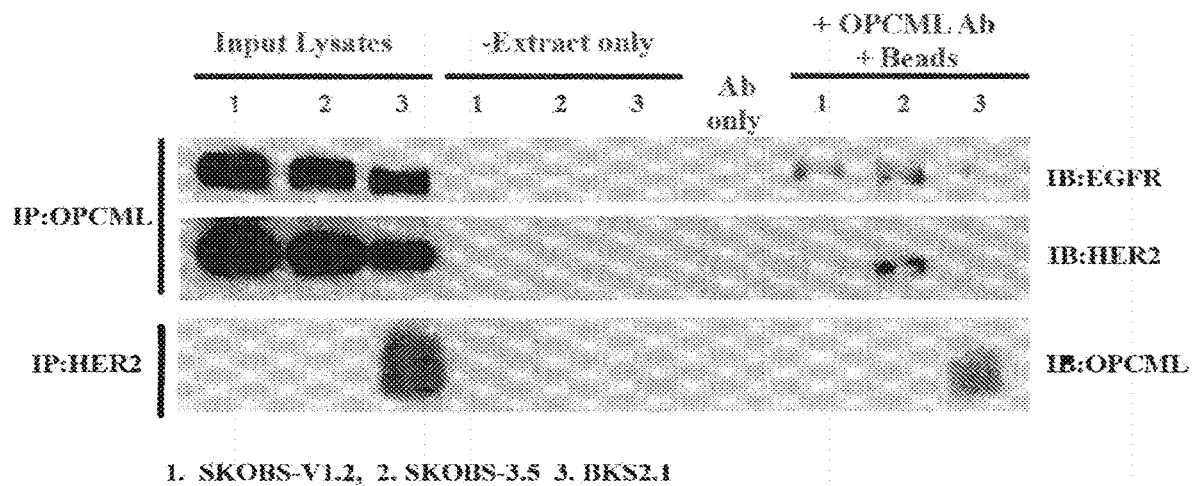
1. SKOBS-V1.2, 2. SKOBS-3.5 3. BKS2.1
A (ii)
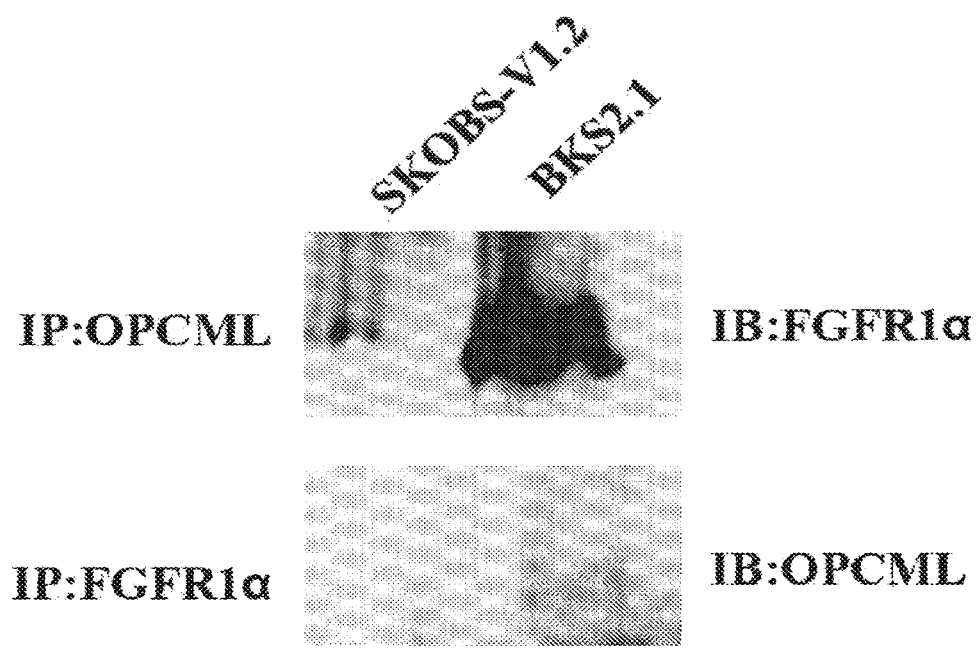

FIGURE 2 Continued
C (i)
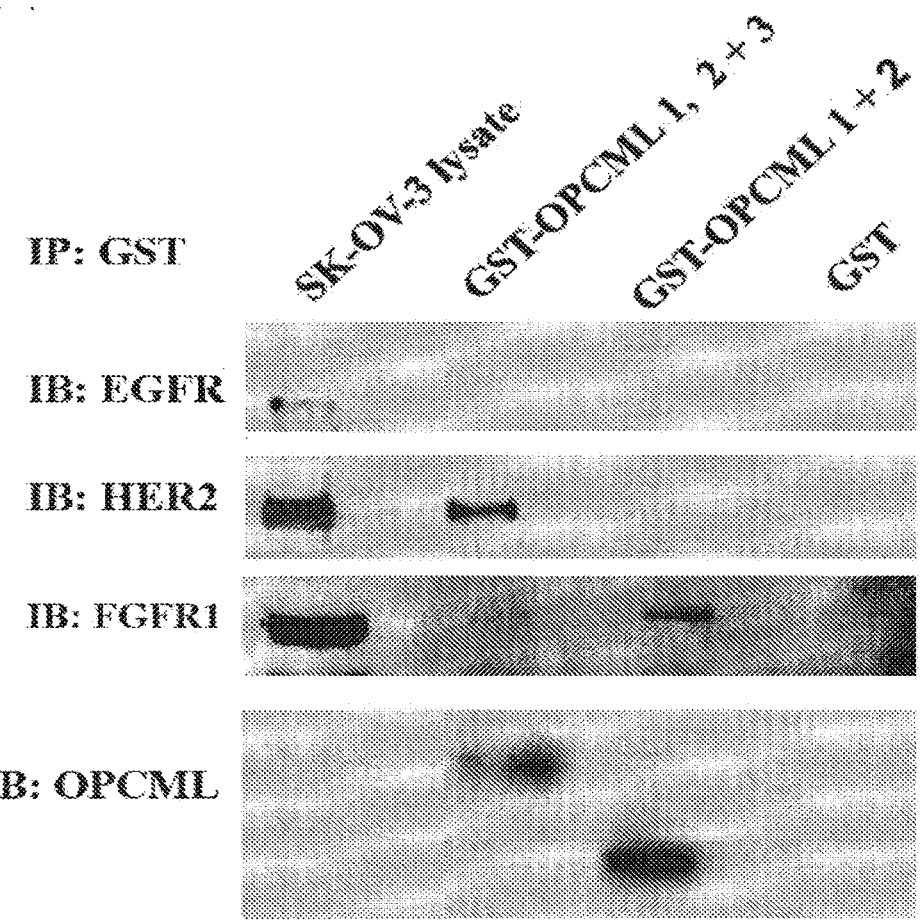
C (ii)
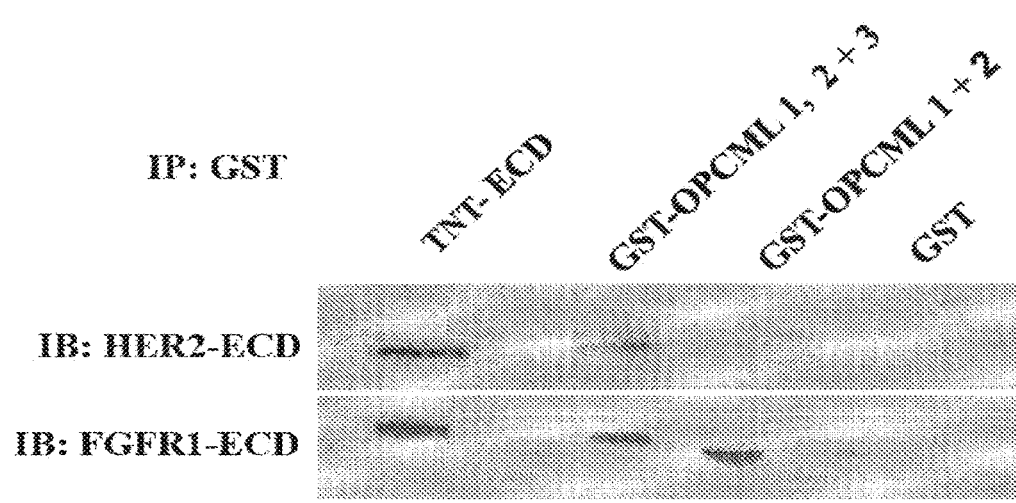

FIGURE 3
A (i)
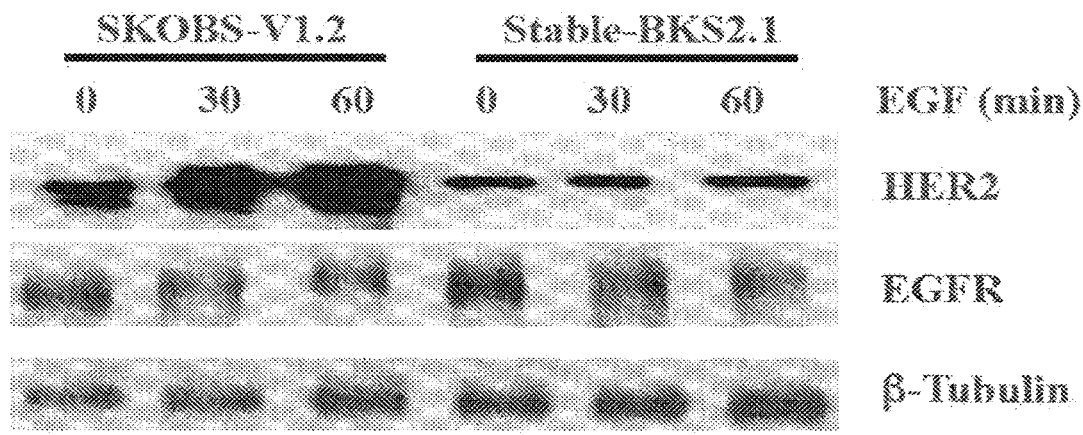
A (ii)
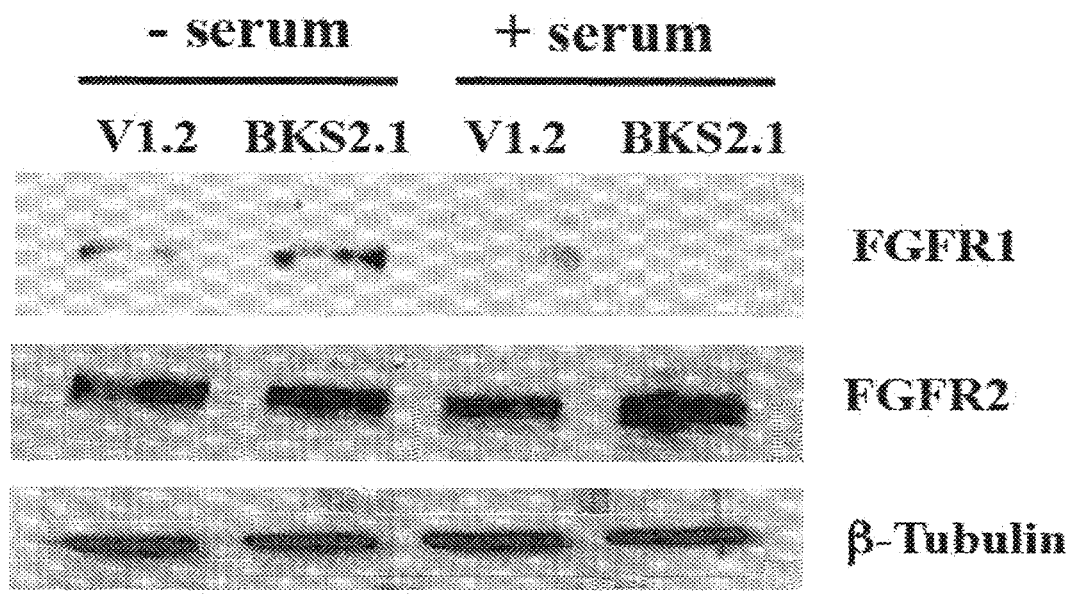

FIGURE 3 Continued
C (i)
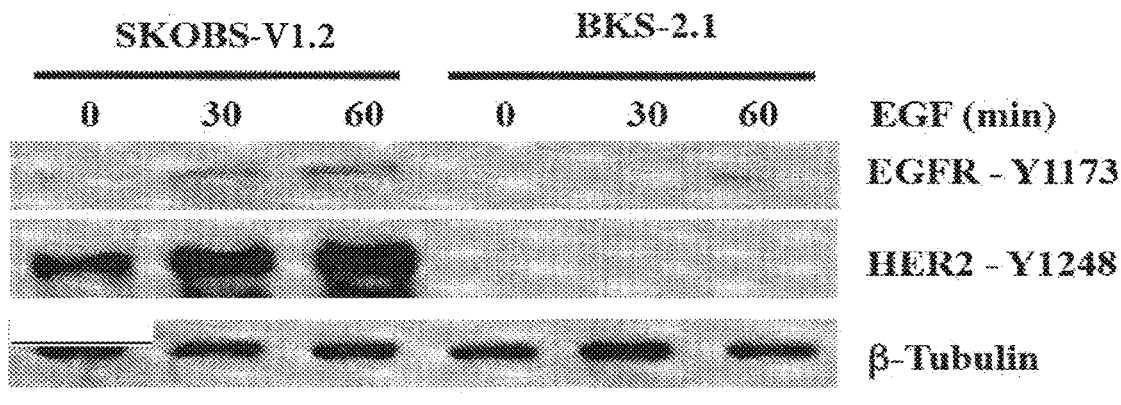
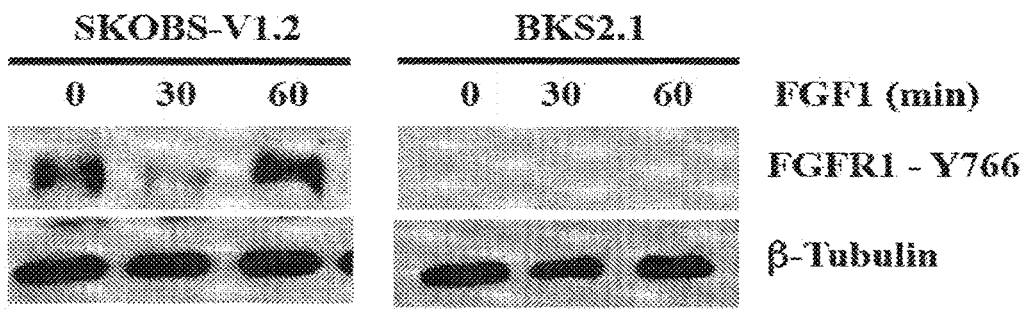
C (ii)
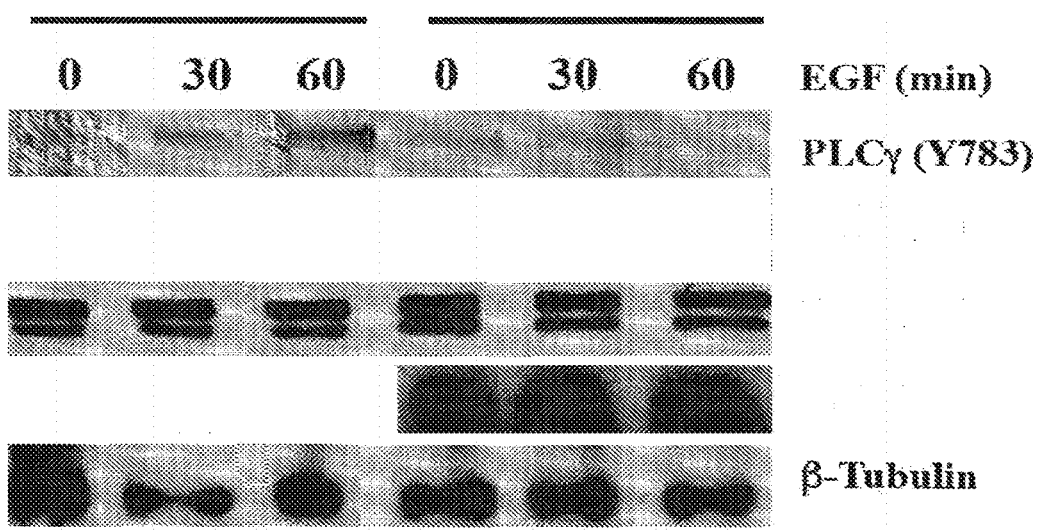

FIGURE 3 Continued
C(iii)
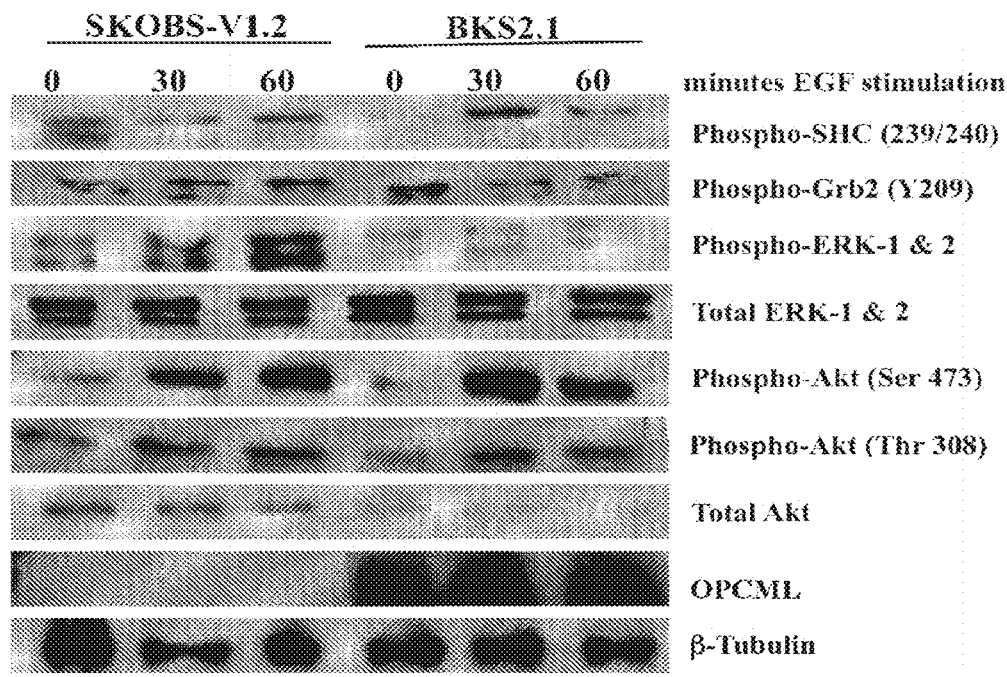
C(iv)
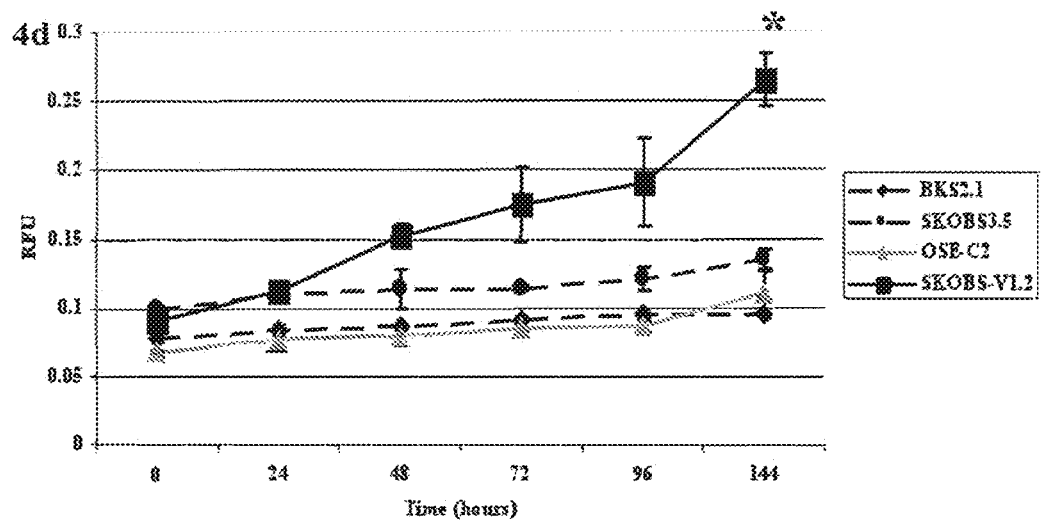
MTT for 0.25% FCS medium supplemented with 50ng/ml EGF
\* $p < 0.0001$

FIGURE 3 Continued
D
(i) Stable OPCML Transfection
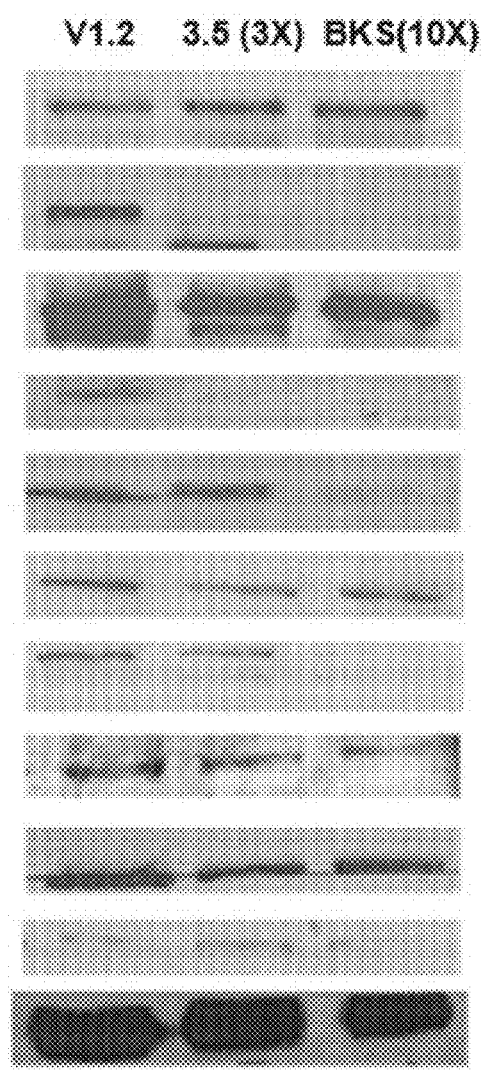
(ii) OPCML SiRNA
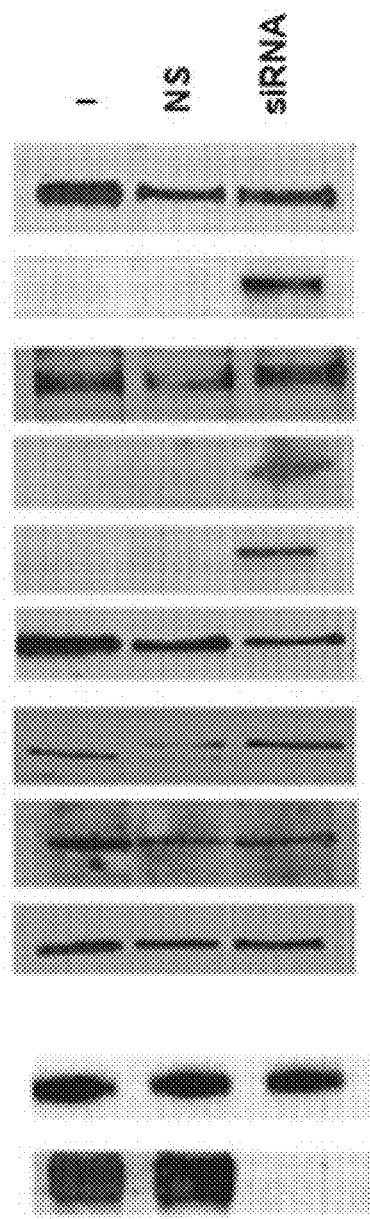

FIGURE 4
A
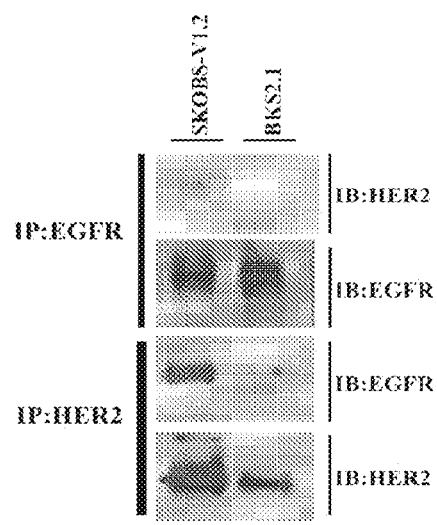
B
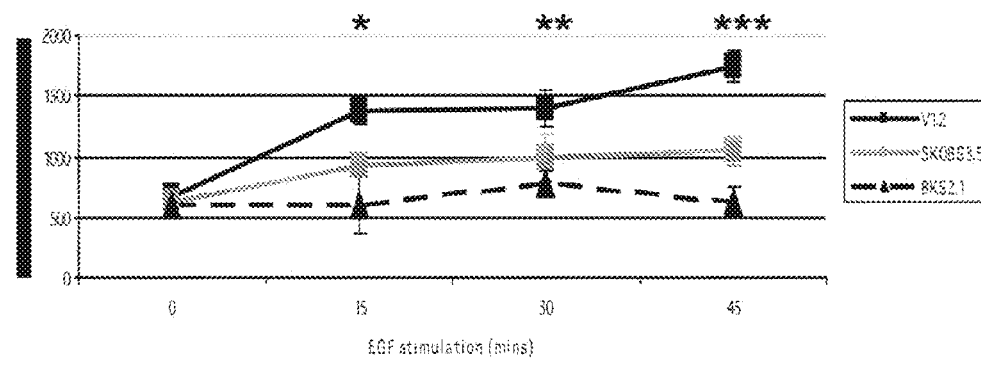
Receptor availability through [$^{125}$-I] EGF binding
*P=0.005, P=0.024, *P=0.003

A (ii)

A (iii)

FIGURE 5 Continued
B (i)
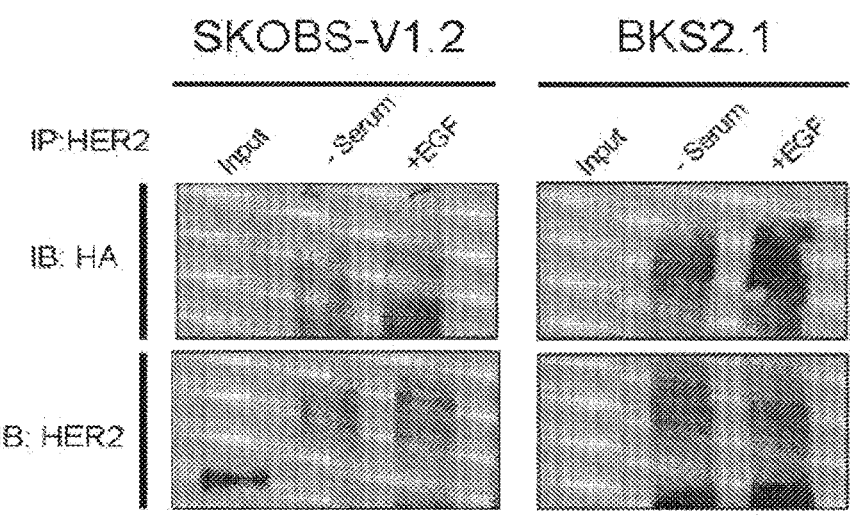
B (ii)
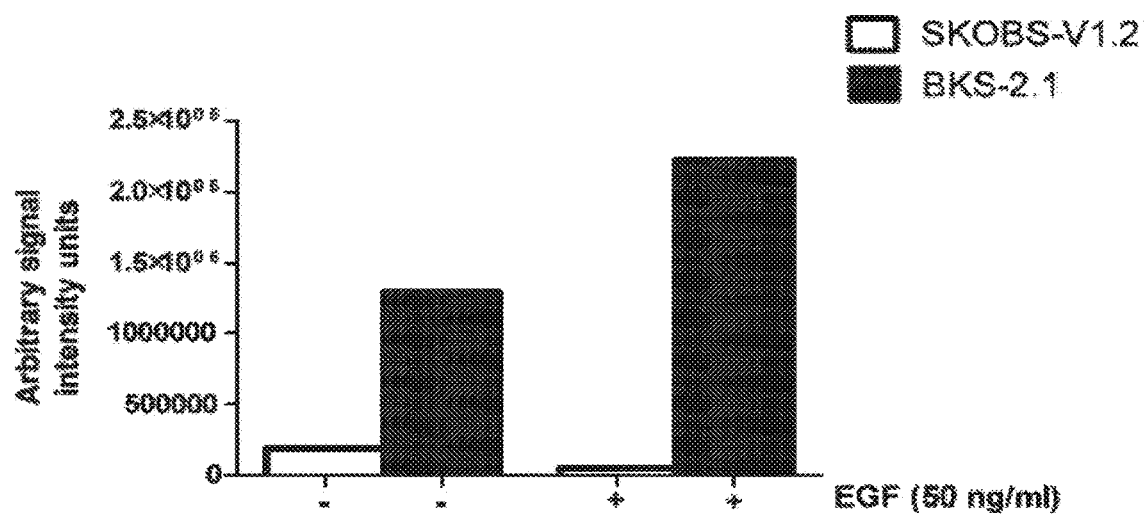

FIGURE 5 Continued
C (i)
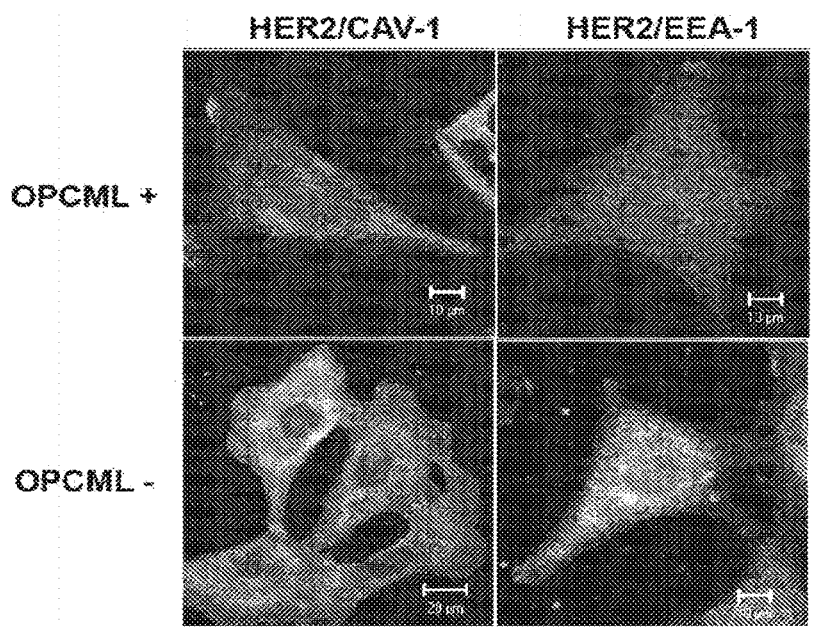
C (ii)
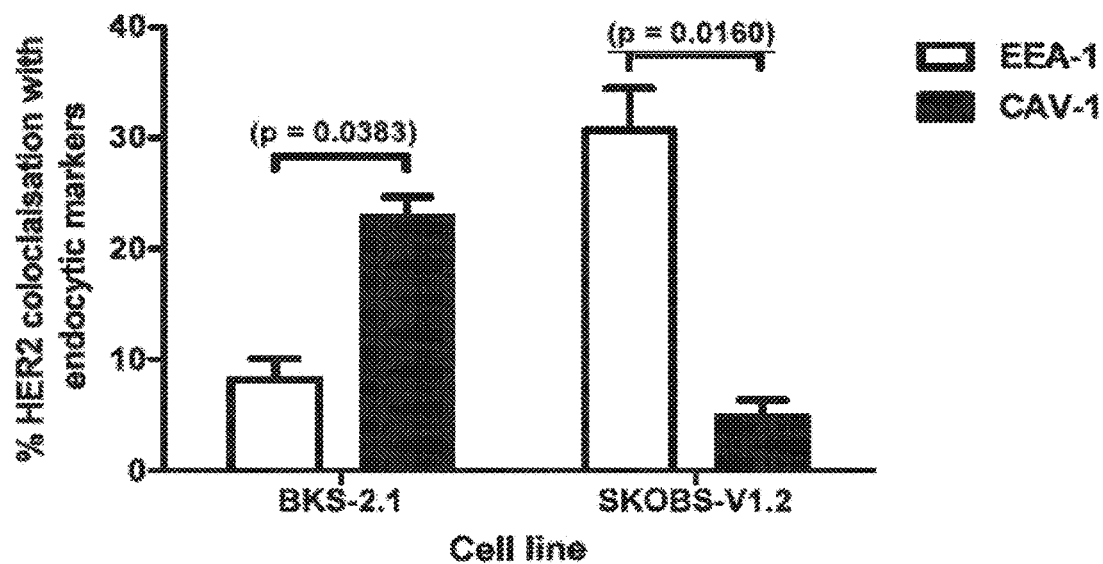

FIGURE 5 Continued
D (i)
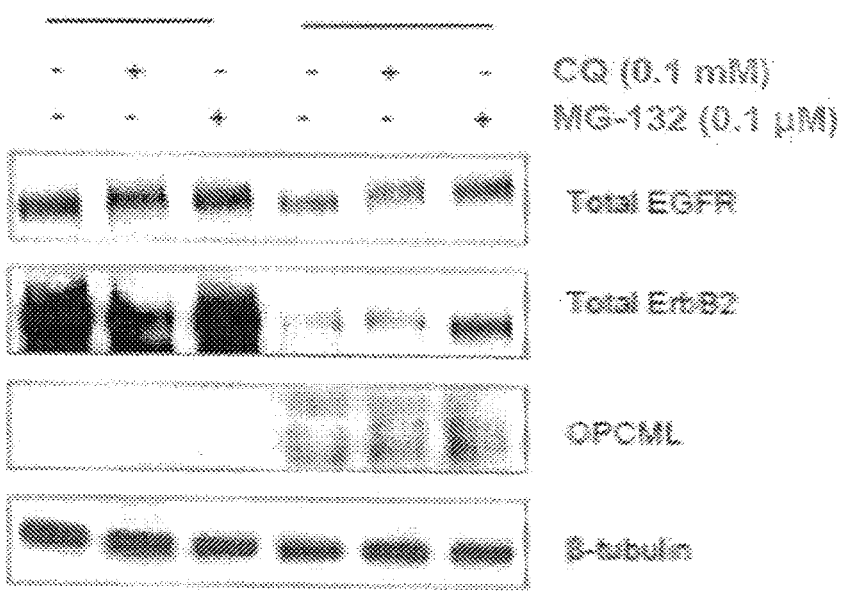
D (ii)
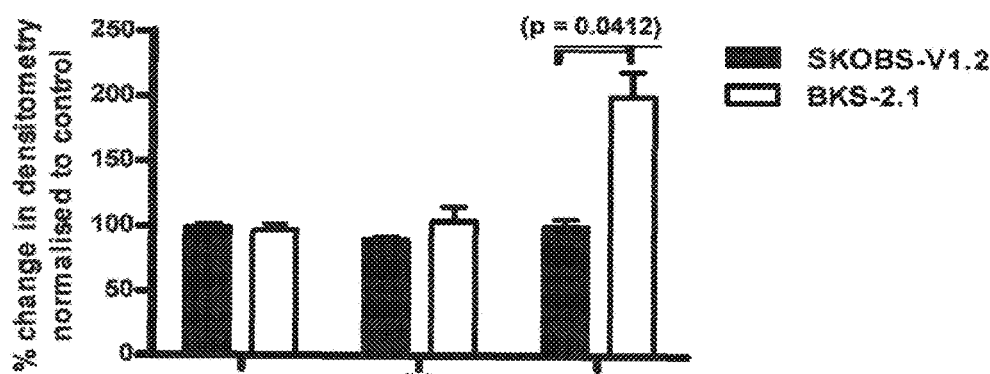
D (iii)

FIGURE 6
A (i)
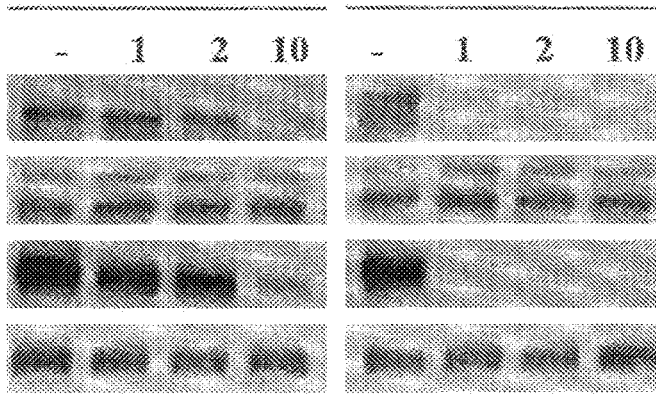
A (ii)
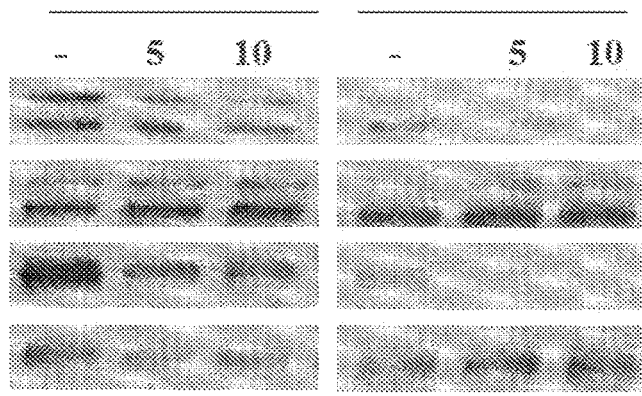

A (i)

Malignant cases only, OPCML alone dichotomous at median cut-off

A (ii)

Malignant cases only, Combinations of Her2 and OPCML

Affymetrix ID: 206215_at
Gene Symbol: OPCML
Survival option: Relapse Free Survival
Split patients by: Lower quartile
Compute median over entire database: false
Cutoff value used in analysis: 46
Expression range of the probe: 1 - 1133

Restrictions

ER status: all
*derive ER status from gene expression data:* false
Lymph node status: all
Grade: all

Results

P value: 0
Multiple testing corrected p value: 0

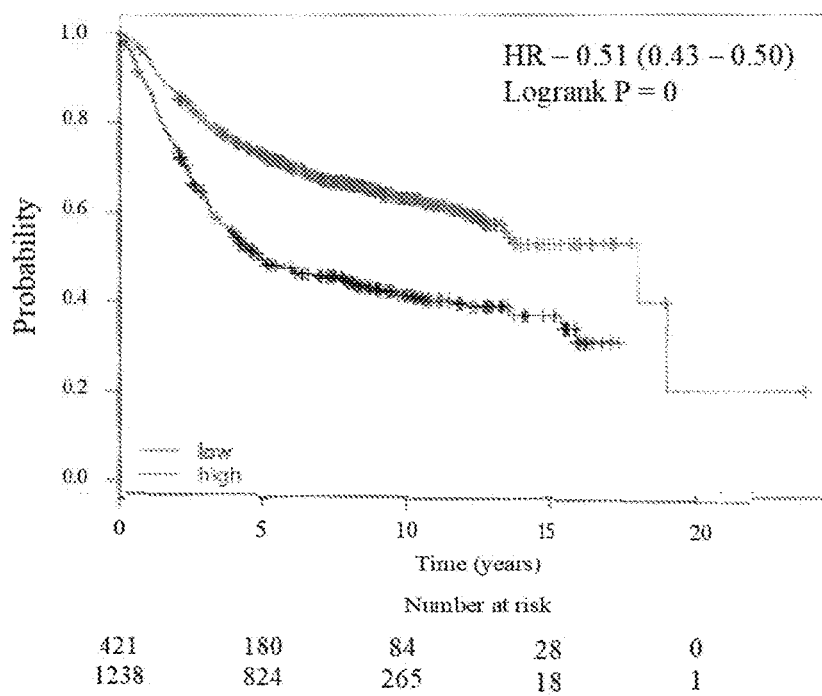

A3

Affymetrix ID: 206215_at
Gene Symbol: OPCML
Survival option: Relapse Free Survival
Split patients by: Lower quartile
Compute median over entire database: false

Restrictions

ER status: negative
*derive ER status from gene expression data:* true
Lymph node status: all
Grade: all

Results

P value: 0

C

D

FIGURE 13
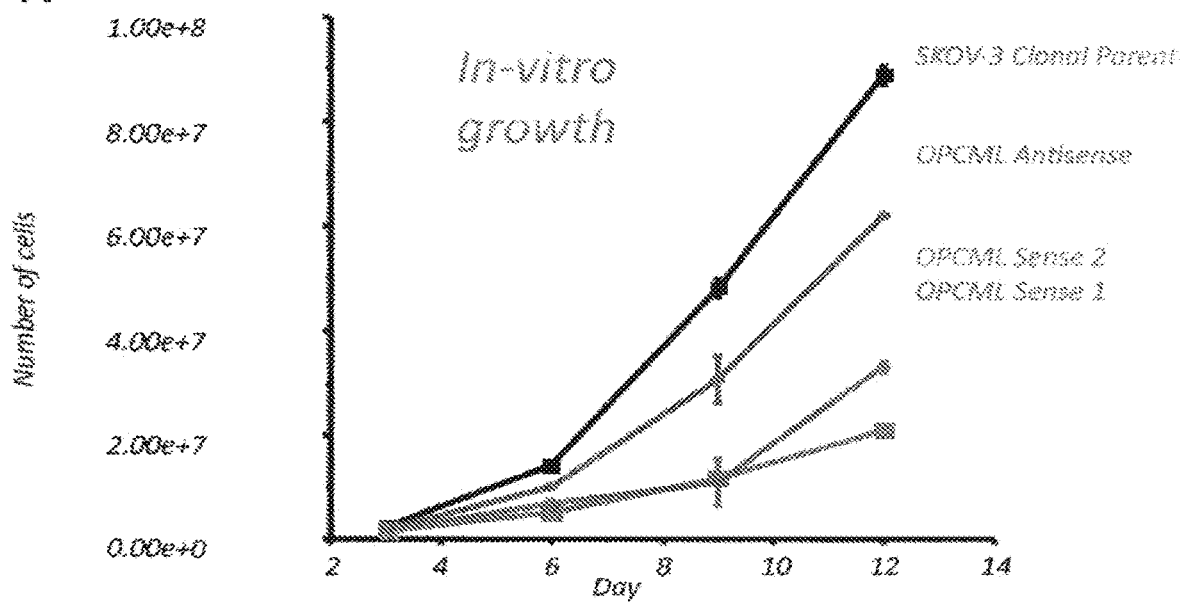
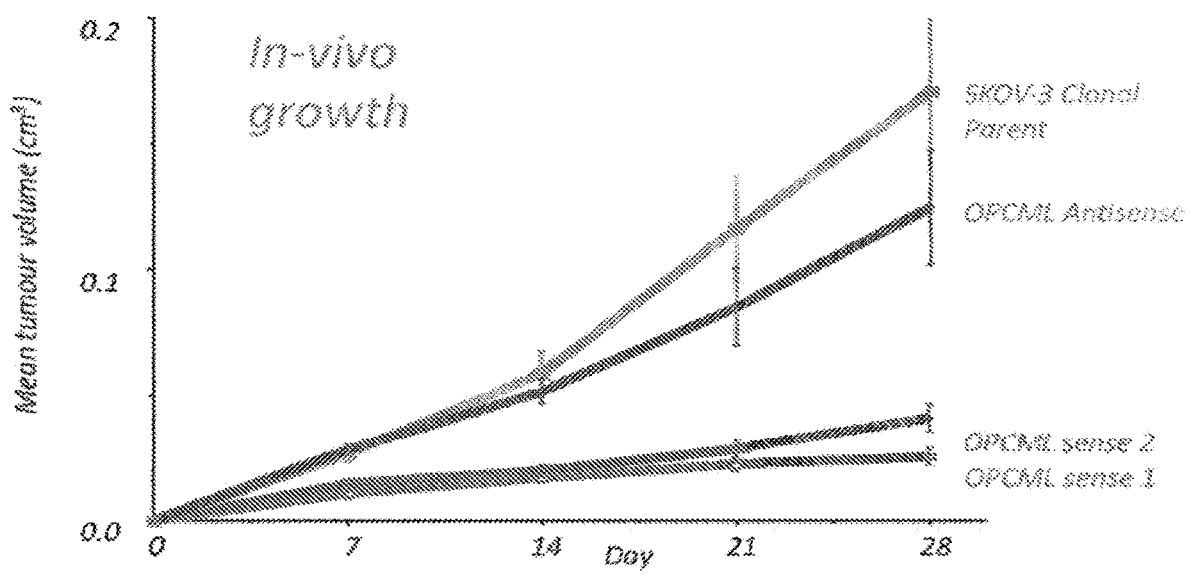

FIGURE 14

```
  1  MGVCGYLFLP WKCLVVVSLR LLFLVPTGVP VRSGDATFPK AMDNVTVRQG ESATLRCTID
 61  DRVTRVAWLN RSTILYAGND KWSIDPRVII LVNTPTQYSI MIQNVDVYDE GPYTCSVQTD
121  NHPKTSRVHL IVQVPPQIMN ISSDITVNEG SSVTLLCLAI GRPEPTVTWR HLSVKEGQGF
181  VSEDEYLEIS DIKRDQSGEY ECSALNDVAA PDVRKVKITV NYPPYISKAK NTGVSVGQKG
241  ILSCEASAVP MAEFQWFKEE TRLATGLDGM RIENKGRMST LTFFNVSEKD YGNYTCVATN
301  KLGNTNASIT LYGPGAVIDG VNSASRALAC LWLSGTLLAH FFIKF
```

PKAMDNVTVRQGESATLRCTIDDRVTRVAWLNRSTILYAGNDKWSIDPRVIILVNT
PTQYSIMIQNVDVYDEGPYTCSVQTDNHPKTS

Ig 2:

PQIMNISSDITVNEGSSVTLLCLAIGRPEPTVTWRHLSVKEGQGFVSEDEYLEISDI
KRDQSGEYECSALNDVAAPDVRKVKIT

Ig 3:

PPYISKAKNTGVSVGQKGILSCEASAVPMAEFQWFKEETRLATGLDGMRIENKGR
MSTLTFFNVSEKDYGNYTCVATNKLGNTNASIT

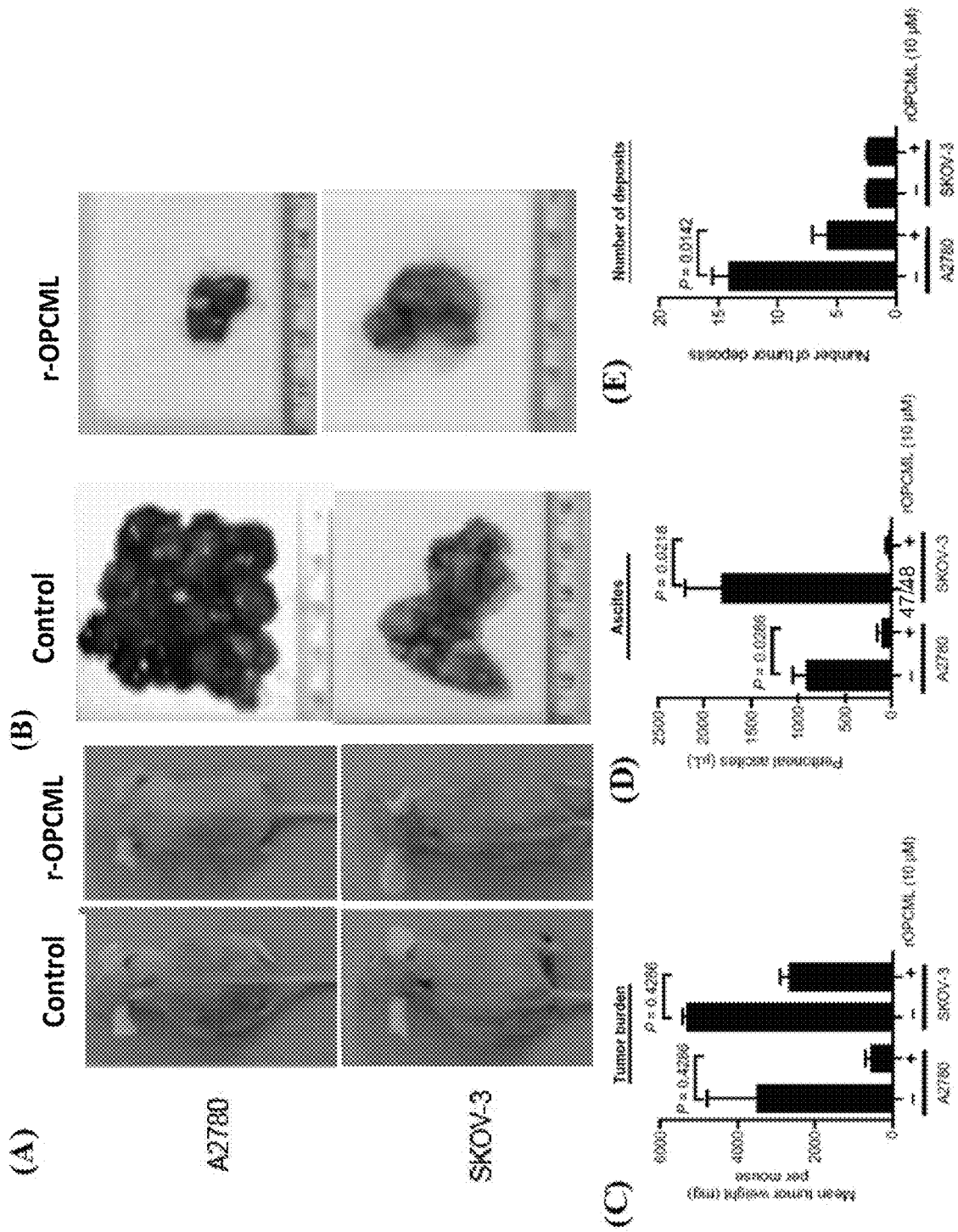

SEQUENCE LISTING

```
<160> NUMBER OF SEQ ID NOS: 6

<210> SEQ ID NO 1
<211> LENGTH: 345
<212> TYPE: PRT
<213> ORGANISM: Homo sapiens

<400> SEQUENCE: 1

Met Gly Val Cys Gly Tyr Leu Phe Leu Pro Trp Lys Cys Leu Val Val
1               5                   10                  15

Val Ser Leu Arg Leu Leu Phe Leu Val Pro Thr Gly Val Pro Val Arg
            20                  25                  30

Ser Gly Asp Ala Thr Phe Pro Lys Ala Met Asp Asn Val Thr Val Arg
        35                  40                  45

Gln Gly Glu Ser Ala Thr Leu Arg Cys Thr Ile Asp Asp Arg Val Thr
    50                  55                  60

Arg Val Ala Trp Leu Asn Arg Ser Thr Ile Leu Tyr Ala Gly Asn Asp
65                  70                  75                  80

Lys Trp Ser Ile Asp Pro Arg Val Ile Ile Leu Val Asn Thr Pro Thr
                85                  90                  95

Gln Tyr Ser Ile Met Ile Gln Asn Val Asp Val Tyr Asp Glu Gly Pro
            100                 105                 110

Tyr Thr Cys Ser Val Gln Thr Asp Asn His Pro Lys Thr Ser Arg Val
        115                 120                 125

His Leu Ile Val Gln Val Pro Pro Gln Ile Met Asn Ile Ser Ser Asp
    130                 135                 140

Ile Thr Val Asn Glu Gly Ser Ser Val Thr Leu Leu Cys Leu Ala Ile
```

```
                145                 150                 155                 160
Gly Arg Pro Glu Pro Thr Val Thr Trp Arg His Leu Ser Val Lys Glu
                    165                 170                 175

Gly Gln Gly Phe Val Ser Glu Asp Glu Tyr Leu Glu Ile Ser Asp Ile
                    180                 185                 190

Lys Arg Asp Gln Ser Gly Glu Tyr Glu Cys Ser Ala Leu Asn Asp Val
                    195                 200                 205

Ala Ala Pro Asp Val Arg Lys Val Lys Ile Thr Val Asn Tyr Pro Pro
                    210                 215                 220

Tyr Ile Ser Lys Ala Lys Asn Thr Gly Val Ser Val Gly Gln Lys Gly
225                 230                 235                 240

Ile Leu Ser Cys Glu Ala Ser Ala Val Pro Met Ala Glu Phe Gln Trp
                    245                 250                 255

Phe Lys Glu Glu Thr Arg Leu Ala Thr Gly Leu Asp Gly Met Arg Ile
                    260                 265                 270

Glu Asn Lys Gly Arg Met Ser Thr Leu Thr Phe Phe Asn Val Ser Glu
                    275                 280                 285

Lys Asp Tyr Gly Asn Tyr Thr Cys Val Ala Thr Asn Lys Leu Gly Asn
                    290                 295                 300

Thr Asn Ala Ser Ile Thr Leu Tyr Gly Pro Gly Ala Val Ile Asp Gly
305                 310                 315                 320

Val Asn Ser Ala Ser Arg Ala Leu Ala Cys Leu Trp Leu Ser Gly Thr
                    325                 330                 335

Leu Leu Ala His Phe Phe Ile Lys Phe
                    340                 345

<210> SEQ ID NO 2
<211> LENGTH: 84
<212> TYPE: PRT
<213> ORGANISM: Homo sapiens

<400> SEQUENCE: 2

Pro Gln Ile Met Asn Ile Ser Ser Asp Ile Thr Val Asn Glu Gly Ser
1               5                   10                  15

Ser Val Thr Leu Leu Cys Leu Ala Ile Gly Arg Pro Glu Pro Thr Val
                20                  25                  30

Thr Trp Arg His Leu Ser Val Lys Glu Gly Gln Gly Phe Val Ser Glu
            35                  40                  45

Asp Glu Tyr Leu Glu Ile Ser Asp Ile Lys Arg Asp Gln Ser Gly Glu
        50                  55                  60

Tyr Glu Cys Ser Ala Leu Asn Asp Val Ala Ala Pro Asp Val Arg Lys
65                  70                  75                  80

Val Lys Ile Thr

<210> SEQ ID NO 3
<211> LENGTH: 88
<212> TYPE: PRT
<213> ORGANISM: Homo sapiens

<400> SEQUENCE: 3

Pro Pro Tyr Ile Ser Lys Ala Lys Asn Thr Gly Val Ser Val Gly Gln
1               5                   10                  15

Lys Gly Ile Leu Ser Cys Glu Ala Ser Ala Val Pro Met Ala Glu Phe
                20                  25                  30

Gln Trp Phe Lys Glu Glu Thr Arg Leu Ala Thr Gly Leu Asp Gly Met
            35                  40                  45
```

Arg Ile Glu Asn Lys Gly Arg Met Ser Thr Leu Thr Phe Phe Asn Val
    50                  55                  60

Ser Glu Lys Asp Tyr Gly Asn Tyr Thr Cys Val Ala Thr Asn Lys Leu
65                  70                  75                  80

Gly Asn Thr Asn Ala Ser Ile Thr
                85

<210> SEQ ID NO 4
<211> LENGTH: 88
<212> TYPE: PRT
<213> ORGANISM: Homo sapiens

<400> SEQUENCE: 4

Pro Lys Ala Met Asp Asn Val Thr Val Arg Gln Gly Glu Ser Ala Thr
1               5                   10                  15

Leu Arg Cys Thr Ile Asp Asp Arg Val Thr Arg Val Ala Trp Leu Asn
                20                  25                  30

Arg Ser Thr Ile Leu Tyr Ala Gly Asn Asp Lys Trp Ser Ile Asp Pro
            35                  40                  45

Arg Val Ile Ile Leu Val Asn Thr Pro Thr Gln Tyr Ser Ile Met Ile
    50                  55                  60

Gln Asn Val Asp Val Tyr Asp Glu Gly Pro Tyr Thr Cys Ser Val Gln
65                  70                  75                  80

Thr Asp Asn His Pro Lys Thr Ser
                85

<210> SEQ ID NO 5
<211> LENGTH: 816
<212> TYPE: DNA
<213> ORGANISM: Homo sapiens

<400> SEQUENCE: 5
cccaaagcta tggacaacgt gacggtccgg caggggagag cgccaccct caggtgtacc      60 atagatgacc gggtaacccg ggtggcctgg ctaaaccgca gcaccatcct ctacgctggg    120
aatgacaagt ggtccataga ccctcgtgtg atcatcctgg tcaatacacc aacccagtac    180
agcatcatga tccaaaatgt ggatgtgtat gacgaaggtc cgtacacctg ctctgtgcag    240
acagacaatc atcccaaaac gtcccgggtt cacctaatag tgcaagttcc tcctcagatc    300
atgaatatct cctcagacat cactgtgaat gagggaagca gtgtgaccct gctgtgtctt    360
gctattggca gaccagagcc aactgtgaca tggagacacc tgtcagtcaa ggaaggccag    420
ggctttgtaa gtgaggatga gtacctggag atctctgaca tcaagcgaga ccagtccggg    480
gagtacgaat gcagcgcgtt gaacgatgtc gctgcgcccg atgtgcggaa agtaaaaatc    540
actgtaaact atcctcccta tatctcaaaa gccaagaaca ctggtgtttc agtcggtcag    600
aagggcatcc tgagctgtga agcctctgca gtccccatgg ctgaattcca gtggttcaag    660
gaagaaacca ggttagccac tggtctggat ggaatgagga ttgaaaacaa aggccgcatg    720
tccactctga ctttcttcaa tgtttcagaa aaggattatg gaactatac ttgtgtggcc    780 acgaacaagc ttgggaacac caatgccagc atcaca                              816

<210> SEQ ID NO 6
<211> LENGTH: 272
<212> TYPE: PRT
<213> ORGANISM: Artificial
<220> FEATURE:
<223> OTHER INFORMATION: Recombinant human OPCML

```
<400> SEQUENCE: 6

Pro Lys Ala Met Asp Asn Val Thr Val Arg Gln Gly Glu Ser Ala Thr
1               5                   10                  15

Leu Arg Cys Thr Ile Asp Asp Arg Val Thr Arg Val Ala Trp Leu Asn
                20                  25                  30

Arg Ser Thr Ile Leu Tyr Ala Gly Asn Asp Lys Trp Ser Ile Asp Pro
            35                  40                  45

Arg Val Ile Ile Leu Val Asn Thr Pro Thr Gln Tyr Ser Ile Met Ile
        50                  55                  60

Gln Asn Val Asp Val Tyr Asp Glu Gly Pro Tyr Thr Cys Ser Val Gln
65                  70                  75                  80

Thr Asp Asn His Pro Lys Thr Ser Arg Val His Leu Ile Val Gln Val
                85                  90                  95

Pro Pro Gln Ile Met Asn Ile Ser Ser Asp Ile Thr Val Asn Glu Gly
                100                 105                 110

Ser Ser Val Thr Leu Leu Cys Leu Ala Ile Gly Arg Pro Glu Pro Thr
            115                 120                 125

Val Thr Trp Arg His Leu Ser Val Lys Glu Gly Gln Gly Phe Val Ser
        130                 135                 140

Glu Asp Glu Tyr Leu Glu Ile Ser Asp Ile Lys Arg Asp Gln Ser Gly
145                 150                 155                 160

Glu Tyr Glu Cys Ser Ala Leu Asn Asp Val Ala Ala Pro Asp Val Arg
                165                 170                 175

Lys Val Lys Ile Thr Val Asn Tyr Pro Pro Tyr Ile Ser Lys Ala Lys
            180                 185                 190

Asn Thr Gly Val Ser Val Gly Gln Lys Gly Ile Leu Ser Cys Glu Ala
        195                 200                 205

Ser Ala Val Pro Met Ala Glu Phe Gln Trp Phe Lys Glu Glu Thr Arg
    210                 215                 220

Leu Ala Thr Gly Leu Asp Gly Met Arg Ile Glu Asn Lys Gly Arg Met
225                 230                 235                 240

Ser Thr Leu Thr Phe Phe Asn Val Ser Glu Lys Asp Tyr Gly Asn Tyr
                245                 250                 255

Thr Cys Val Ala Thr Asn Lys Leu Gly Asn Thr Asn Ala Ser Ile Thr
                260                 265                 270
```

CANCER THERAPEUTIC METHODS UTILIZING OPCML FRAGMENT

The present invention relates to the field of medicine, more specifically to the field of cancer. In particular, the present invention relates to the role of OPCML in cancer prognosis, theragnosis, treatment and research.

Cancer is a leading cause of mortality worldwide, accounting for 7.9 million deaths (around 13% of all deaths) in 2007, with lung, stomach, liver, colon and breast cancers causing the most deaths each year (World Health Organization, WHO). According to the WHO, deaths from cancer worldwide are projected to continue rising, with an estimated 12 million deaths in 2030. There is thus a very great need for additional and improved methods of treating cancers.

The etiology of cancer is multifactorial, with genetic, environmental, medical, and lifestyle factors interacting to produce a given malignancy. Knowledge of cancer genetics is rapidly improving our understanding of cancer biology, helping to identify at-risk individuals, furthering the ability to characterize malignancies, establishing treatment tailored to the molecular fingerprint of the disease, and leading to the development of new therapeutic modalities. Thus there is a need for greater knowledge and understanding of cancer genetics in order to improve all aspects of cancer management, including prevention, screening, and treatment.

OPCML (also known as OBCAM) is a member of the IgLON family of cell-surface GPI-anchored proteins and has been previously validated as an epigenetic biomarker for ovarian cancer. In WO 03/002765, and in Sellar et al (2003, Nature Genetics 34(3): 337-343), we showed that the OPCML gene shows frequent loss of heterozygosity in human tumors, that OPCML gene inactivation is via extensive methylation of a CpG island in the promoter, and that OPCML behaves as a tumor suppressor gene in in vivo models.

Subsequently, OPCML was found to be epigenetically inactivated and downregulated in a wide a variety of cancers. For example, Reed et al found that OPCML is down-regulated in gliomas and other brain tumors (Reed et al (2007) "Expression of cellular adhesion molecule 'OPCML' is down-regulated in gliomas and other brain tumors" *Neuropathology and Applied Neurobiology* 33(1): 77-85), Cui et al found that the expression of OPCML is frequently silenced or down-regulated in multiple tumors due to its high level of promoter methylation (Cui et al (2008) "OPCML Is a Broad Tumor Suppressor for Multiple Carcinomas and Lymphomas with Frequently Epigenetic Inactivation", *PLoS ONE* 3(8): e2990), and Li et al found OPCML methylation in hepatocellular carcinoma (Li et al (2010) "CpG Island Methylator Phenotype Associated with Tumor Recurrence in Tumor-Node-Metastasis Stage I Hepatocellular Carcinoma" *Ann. Surg. Oncol.* [Epub ahead of print]).

We have now found that OPCML is a genetic marker of cancer that can be used, alone or in combination with other genetic markers, for the prognosis of cancer in human patients and to assess progression free survival (PFS). Our studies on the role and effect of OPCML on receptor tyrosine kinases (RTKs) have shown that OPCML can be used as a genetic marker to select specific treatments for cancer patients. We have also shown that OPCML can be used as treatment for specific subsets of patients defined by their RTK profile.

Specifically, we have shown that OPCML mediates a growth suppressive effect by negatively regulating specific receptor tyrosine kinases, especially HER2, HER4, FGFR1, EPHA2 and FGFR3, and we highlight prognostic, predictive and therapeutic approaches based on OPCML's role in cancer. In Example 1 we demonstrate the effect of OPCML on receptor tyrosine kinase signaling in OPCML expressing cell lines and show that OPCML is a prognostic factor for ovarian cancer; in Example 2 we provide evidence that exogenous OPCML inhibits proliferation of cancer cell lines in vitro; in Example 3 we confirm that OPCML is also a prognostic factor for breast, lung and glioma cancers; in Example 4 we provide evidence of the effect of OPCML on inhibiting cancer cell growth in vivo; and in Example 5 we provide further supporting evidence of the effects of OPCML.

Accordingly, a first aspect of the invention provides a method of treating a patient having a cancer in which HER2, HER4, FGFR1, EPHA2 and/or FGFR3 is upregulated and/or in which HER2, HER4, FGFR1, EPHA2 and/or FGFR3 mediated-signaling is upregulated, the method comprising administering to the patient a compound comprising or consisting of an OPCML polypeptide (SEQ ID NO: 1), or a fragment thereof which comprises at least one Ig domain of OPCML, or a variant thereof having at least 90% sequence identity with the OPCML polypeptide or the fragment thereof, or a nucleic acid molecule which encodes the OPCML polypeptide or fragment or variant thereof.

This aspect of the invention includes the use of a compound comprising or consisting of an OPCML polypeptide (SEQ ID NO: 1), or a fragment thereof which comprises at least one Ig domain of OPCML, or a variant thereof having at least 90% sequence identity with the OPCML polypeptide or the fragment thereof, or a nucleic acid molecule which encodes the OPCML polypeptide or fragment or variant thereof, in the preparation of a medicament for treating a patient having a cancer in which HER2, HER4, FGFR1, EPHA2 and/or FGFR3 is upregulated and/or in which HER2, HER4, FGFR1, EPHA2 and/or FGFR3 mediated-signaling is upregulated.

This aspect of the invention also includes a compound comprising or consisting of an OPCML polypeptide (SEQ ID NO: 1), or a fragment thereof which comprises at least one Ig domain of OPCML, or a variant thereof having at least 90% sequence identity with the OPCML polypeptide or the fragment thereof, or a nucleic acid molecule which encodes the OPCML polypeptide or fragment or variant thereof for use in treating a patient having a cancer in which HER2, HER4, FGFR1, EPHA2 and/or FGFR3 is upregulated and/or in which HER2, HER4, FGFR1, EPHA2 and/or FGFR3 mediated-signaling is upregulated.

The cDNA and amino acid sequences of human HER2 (aka ERBB2; Entrez Gene ID: 2064) are publicly available from the GenBank database under Accession Nos. NM_004448 and NP_004439.

The cDNA and amino acid sequences of human HER4 (aka ERBB4; Entrez Gene ID: 2066) are publicly available from the GenBank database under Accession Nos. NM_005235 and NP_005226.

The cDNA and amino acid sequences of human FGFR1 (Entrez Gene ID: 2260) are publicly available from the GenBank database under Accession Nos. NM_023110 and NP_075598.

The cDNA and amino acid sequences of human FGFR3 (Entrez Gene ID: 2261) are publicly available from the GenBank database under Accession Nos. NM_000142 and NP_000133.

The cDNA and amino acid sequences of human EPHA2 (Entrez Gene ID: 1969) are publicly available from the GenBank database under Accession Nos. NM_004431 and NP_004422 (update version 20 Mar. 2011).

The upregulation of HER2, HER4, FGFR1, EPHA2 and/or FGFR3 may be determined by assessing HER2, HER4, FGFR1, EPHA2 and/or FGFR3 mRNA levels, polypeptide levels or gene copy number using methods that are well known in the art.

In an embodiment, by a cancer in which HER2, HER4, FGFR1, EPHA2 and/or FGFR3 is upregulated we mean that the HER2, HER4, FGFR1, EPHA2 and/or FGFR3 mRNA or polypeptide levels in the cancer are at least 2× greater than control levels. Preferably, the HER2, HER4, FGFR1, EPHA2 and/or FGFR3 mRNA or polypeptide levels are at least 3×, or at least 4×, or at least 5×, or at least 10×, or at least 20×, or at least 30×, or at least 40×, or at least 50×, or at least 100× greater than control levels. The HER2, HER4, FGFR1, EPHA2 and/or FGFR3 mRNA or polypeptide levels in the cancer may be at least 500×, or at least 1,000×, or at least 10,000× greater than control levels.

In an embodiment, by a cancer in which HER2, HER4, FGFR1, EPHA2 and/or FGFR3 is upregulated, we mean that the HER2, HER4, FGFR1, EPHA2 and/or FGFR3 mRNA or polypeptide levels in the cancer are above-median, and preferably are upper quartile, compared to control levels.

In an embodiment, the control levels for HER2, HER4, FGFR1, EPHA2 and/or FGFR3 in the cancer of a specific tissue or organ may be the average (mean, or preferably median) level of HER2, HER4, FGFR1, EPHA2 and/or FGFR3 found in the same tissue or organ in a population of individuals who do not have cancer in that tissue or organ, and typically do not have cancer at all. Typically, the population of individuals is matched for gender, age, and ethnic origin. Preferably, the population of control individuals comprises at least 5, 10, 50, 100, 200, 300, 400 or 500 individuals and more preferably at least 1000, 5000 or 10000 individuals.

In an alternative embodiment, the control levels for HER2, HER4, FGFR1 and/or FGFR3 in the cancer of a specific tissue or organ may be the average (mean, or preferably median) level of HER2, HER4, FGFR1 and/or FGFR3 found in a population of patients with the same cancer. Typically, the population of individuals is matched for gender, age, and ethnic origin. Preferably, the population of control individuals comprises at least 5, 10, 50, 100, 200, 300, 400 or 500 individuals and more preferably at least 1000, 5000 or 10000 individuals.

In an specific embodiment, the level of HER2, HER4, FGFR1, EPHA2 and/or FGFR3 mRNA or polypeptide that is indicative of upregulation is a level of HER2, HER4, FGFR1, EPHA2 and/or FGFR3 in the tissue or organ with the cancer that is equal to or greater than the mean +2 standard deviations (SD) of the level of HER2, HER4, FGFR1, EPHA2 and/or FGFR3 mRNA or polypeptide found in a population of control individuals, usually the control individuals without cancer.

The HER2, HER4, FGFR1, EPHA2 and/or FGFR3 mRNA levels may be measured by methods such as quantitative RT-PCR, as is well known in the art.

In another embodiment, the HER2, HER4, FGFR1, EPHA2 and/or FGFR3 polypeptide levels may be measured by immunohistochemistry (IHC). Using HercepTest™, a semi-quantitative immunohistochemical assay for determination of HER2 protein (c-erbB-2 oncoprotein) overexpression in cancer tissues, HER2 is routinely graded as 0, 1+, 2+, or 3+. If the results are 3+ the cancer is considered to be HER2-positive (HER2+). For the avoidance of doubt, in the context of this invention a HER2+ cancer is one in which HER2 is upregulated.

A similar IHC grading scale may be used for HER4, FGFR1, EPHA2 and FGFR3 wherein a 3+ grading indicates that the cancer is HER4+, FGFR1+, EPHA2+ or FGFR3+, and that the cancer has upregulated HER4, FGFR1, EPHA2 or FGFR3, respectively.

Alternatively, the HER2, HER4, FGFR1, EPHA2 and/or FGFR3 gene copy number may be measured by Fluorescence In Situ Hybridization (FISH). This test uses fluorescent probes to look at the number of gene copies in a cancer cell. If there are more than two copies of the HER2 or HER4 gene, then the cancer is HER2+ or HER4+ positive, and is considered to have upregulated HER2 or HER4, respectively.

For FGFR1 and FGFR3, if >50% of the neoplastic cells have >5 copies of the gene or large gene clusters, the cancer is considered to be FGFR1+ or FGFR3+, and may be considered to have upregulated FGFR1+ or FGFR3+, respectively (Elsheikh et al (2007) "FGFR1 amplification in breast carcinomas: a chromogenic in situ hybridisation analysis" *Breast Cancer Research* 9: R23).

EPHA2 upregulation can readily be determined using methods well known in the art, such as those described, for example, by Kataoka et al (2004) "Correlation of EPHA2 overexpression with high microvessel count in human primary colorectal cancer." *Cancer Sci.* 95: 136-141; Miyazaki et al (2003) "EphA2 overexpression correlates with poor prognosis in esophageal squamous cell carcinoma." *Int J Cancer.* 103: 657-663; and Nakamura et al (2005) "EPHA2/EFNA1 expression in human gastric cancer." *Cancer Sci.* 96: 42-47.

Thus, by a cancer in which HER2, HER4, FGFR1, EPHA2 and/or FGFR3 is upregulated, we also mean that the cancer is considered to 'positive' for HER2, HER4, FGFR1, EPHA2 and/or FGFR3.

In an embodiment, the upregulation of HER2, HER4, FGFR1, EPHA2 and/or FGFR3 mediated-signaling may be determined by assessing HER2, HER4, FGFR1, EPHA2 and/or FGFR3 ligand levels in the patient. EPHRINA1 (EFNA1) is the ligand for EPHA2. Increased ligand levels, e.g. 2×, 5×, 10×, 50× or 100× above control levels, or above-median or upper-quartile levels, compared to control levels, may be indicative that the RTK mediated-signaling is upregulated. Ligand levels can be determined, for example, using methods that are well known in the art such as FISH to measure gene copy number, qRT-PCR, to measure mRNA levels and semi-quantitative protein evaluation by IHC or Western blotting.

Cancers in which HER2, HER4, FGFR1, EPHA2 and/or FGFR3 mediated-signaling is upregulated may be determined by various methods in the art. For example, the expression of HER2, HER4, FGFR1, EPHA2 and/or FGFR3 may be assayed in any biological sample that is directly or indirectly derived from the patient such as a cancer biopsy or extract. In an embodiment, antibody-based techniques may be preferred. The normal range of HER2, HER4, FGFR1, EPHA2 and/or FGFR3 expression can then be defined using values from either healthy individuals, or a population of individuals with the same cancer, which can be compared to those obtained from a test patient. Alternatively, the level of HER2, HER4, FGFR1, EPHA2 and/or FGFR3 mediated-signaling can be determined by assessing downstream targets. For example, a particular protein whose expression is known to be under the control of the HER2, HER4, FGFR1, EPHA2 and/or FGFR3 signaling pathway(s)

may be quantified either at the nucleic acid or protein level, typically by qRT-PCR, IHC or Western blotting.

In some cancers, a mutation in the ligand-binding domain of HER2, HER4, FGFR1, EPHA2 and/or FGFR3 may cause constitutive activation of the receptor in the absence of ligand binding, and thus the upregulation of HER2, HER4, FGFR1, EPHA2 and/or FGFR3 mediated-signaling (Arteaga (2002) "Epidermal growth factor receptor dependence in human tumors: more than just expression?" *Oncologist* 7: Suppl 4: 31-39). Mutations that cause constitutive activation of HER2, HER4, FGFR1, EPHA2 and/or FGFR3 can be determined, for example, using methods that are well known in the art, such as DNA sequencing of constitutively active receptors.

In an embodiment, by a cancer in which HER2, HER4, FGFR1, EPHA2 and/or FGFR3 mediated-signaling is upregulated we also include a cancer that is addicted to a HER2, HER4, FGFR1, EPHA2 or FGFR3 signaling pathway. As is known in the art, when a cancer is 'addicted' to a specific RTK pathway, such as a HER2, HER4, FGFR1, EPHA2 or FGFR3 signaling pathway, the cancer becomes largely reliant on the single activated oncogene for cellular signaling (Weinstein & Joe (2008) "Oncogene addiction" *Cancer Res.* 68: 3077-3080; Weinstein & Joe (2006) "Mechanisms of disease: oncogene addiction—a rationale for molecular targeting in cancer therapy" *Nat Clin Pract Oncol.* 3: 448-457; Sharma et al (2006) "Oncogenic shock: explaining oncogene addiction through differential signal attenuation" *Clin Cancer Res.* 12: 4392s-4395s).

The addiction of a cancer to the HER2, HER4, FGFR1, EPHA2 or FGFR3 pathway may be determined by methods well known in the art, such as copy number estimation via SNP chip or by comparative genomic hybridization (CGH), by IHC/Western blotting, or by qRT-PCR.

In an embodiment, the method may further comprise the prior step of identifying a patient having a cancer in which HER2, HER4, FGFR1, EPHA2 and/or FGFR3 is upregulated and/or in which HER2, HER4, FGFR1, EPHA2 and/or FGFR3 mediated-signaling is upregulated. Typically, this involves identifying a patient having a cancer in which HER2, HER4, FGFR1, EPHA2 and/or FGFR3 is upregulated and/or in which HER2, HER4, FGFR1, EPHA2 and/or FGFR3 mediated-signaling is upregulated from the results of previously-conducted testing.

In an alternative embodiment, the method may further comprise the prior step of determining whether the patient has a cancer in which HER2, HER4, FGFR1, EPHA2 and/or FGFR3 is upregulated, and/or in which HER2, HER4, FGFR1, EPHA2 and/or FGFR3 mediated-signaling is upregulated. Typically, this involves testing a sample from the patient to determine whether the patient has a cancer in which HER2, HER4, FGFR1, EPHA2 and/or FGFR3 is upregulated, and/or in which HER2, HER4, FGFR1, EPHA2 and/or FGFR3 mediated-signaling is upregulated.

OPCML (aka OBCAM) was described in 1995 by Shark & Lee (Shark & Lee (1995) "Cloning, sequencing and localization to chromosome 11 of a cDNA encoding a human opioid-binding cell adhesion molecule (OBCAM)" *Gene* 155: 213-217). The cDNA and amino acid sequences of human OPCML are publicly available from GenBank under Accession Nos. NM_002545 and NP_002536. The amino acid sequence from NP_002536 is also shown in FIG. 14 (SEQ ID NO: 1). Further sequences for OPCML in rat and cow are available from GenBank under the following Accession Nos: M88711 (*Rattus norvegicus*) and X12672 (*Bos taurus*).

The Ig1 domain of OPCML spans residues 39-126 of human OPCML, the Ig2 domain of OPCML spans residues 136-219 of human OPCML, and the Ig3 domain of OPCML spans residues 223-310 of human OPCML. The amino acid sequence of the Ig1 domain (SEQ ID No: 4), Ig2 domain (SEQ ID No: 2) and Ig3 domain (SEQ ID No: 3) of human OPCML are listed in FIG. 15.

In a preferred embodiment, the fragment of OPCML may be one which is lacking the signal sequence, which is found at residues 1-27 of human OPCML.

Additionally or alternatively preferably, the fragment of OPCML may be one which is lacking the C-terminal GPI-anchor site, which is at N322, and residues 323-345 which are cleaved in the attachment process. We have shown that recombinant OPCML lacking this site, i.e. lacking residues 322-345, has activity in in vitro and in vivo studies. This is particularly surprising as it would not expected that the recombinant OPCML protein would have activity if it lacked its membrane attachment site. Thus, it is appreciated that the invention includes a pharmaceutical composition comprising a fragment of OPCML, preferably human OPCML, that lacks the GPI-anchor site; its use as a medicament; the use of such a fragment of OPCML in the preparation of a medicament for treating cancer; a method of treating cancer by administering such a fragment of OPCML to a patient; and such a fragment of OPCML for use in treating cancer.

Accordingly, in an embodiment, the fragment of OPCML for use in the above methods may be one that comprises or consists of residues 28-321 of human OPCML. It is appreciated that the invention includes a pharmaceutical composition comprising such a fragment of human OPCML; its use as a medicament; the use of such a fragment of OPCML in the preparation of a medicament for treating cancer; a method of treating cancer by administering such a fragment of OPCML to a patient; and such a fragment of OPCML for use in treating cancer.

In a further embodiment, the fragment of OPCML for use in the above methods may be one that comprises or consists of residues 39-310 of human OPCML. It is also appreciated that the invention includes a pharmaceutical composition comprising such a fragment of human OPCML; its use as a medicament; the use of such a fragment of OPCML in the preparation of a medicament for treating cancer; a method of treating cancer by administering such a fragment of OPCML to a patient; and such a fragment of OPCML for use in treating cancer.

In another embodiment, the fragment of OPCML for use in the above methods may be one that comprises or consists of residues 39-219 of human OPCML. It is also appreciated that the invention includes a pharmaceutical composition comprising such a fragment of human OPCML; its use as a medicament; the use of such a fragment of OPCML in the preparation of a medicament for treating cancer; a method of treating cancer by administering such a fragment of OPCML to a patient; and such a fragment of OPCML for use in treating cancer.

In yet another embodiment, the fragment of OPCML for use in the above methods may be one that comprises or consists of residues 39-126 and residues 223-310 of human OPCML. It is also appreciated that the invention includes a pharmaceutical composition comprising such a fragment of human OPCML; its use as a medicament; the use of such a fragment of OPCML in the preparation of a medicament for treating cancer; a method of treating cancer by administering such a fragment of OPCML to a patient; and such a fragment of OPCML for use in treating cancer.

In still yet another embodiment, the fragment of OPCML for use in the above methods may be one that comprises or consists of residues 136-310 of human OPCML. It is also appreciated that the invention includes a pharmaceutical composition comprising such a fragment of human OPCML; its use as a medicament; the use of such a fragment of OPCML in the preparation of a medicament for treating cancer; a method of treating cancer by administering such a fragment of OPCML to a patient; and such a fragment of OPCML for use in treating cancer.

It is appreciated that a fragment of OPCML that comprises a specified region of OPCML may contain additional residues of OPCML outside the specified region, but does not include the full length protein. More preferably, if the fragment of OPCML comprises a specified region of OPCML and contains additional residues of OPCML outside the specified region, it does not include the GPI-anchor site, the signal sequence or either of the GPI-anchor site and the signal sequence.

It is also appreciated that a fragment of OPCML that comprises or consists of a specified region of OPCML may be in the form of a fusion molecule, as discussed below.

In an embodiment, the fragment of OPCML is at least 85 amino acids in length, such as at least 90, at least 100, at least 125, at least 150, at least 175, at least 200, at least 225, at least 250, at least 275, at least 300 or at least 325 amino acids in length.

In an embodiment, the variant of the OPCML polypeptide or the fragment thereof has at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity, with the OPCML polypeptide or the fragment thereof. Such fragments and variants may be made, for example, using the methods of recombinant DNA technology, protein engineering and site-directed mutagenesis, which are well known in the art, and discussed in more detail below.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., (1994) *Nucleic Acids Res* 22, 4673-80). The parameters used may be as follows: Fast pairwise alignment parameters: K-tuple (word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM.

It is appreciated that OPCML mutations, albeit infrequent, have been detected in ovarian cancer, some of which somatic mutations have been inactivating and lead to a complete loss of function. It is thus preferred that the variant of OPCML or the fragment thereof does not possess any of the mutations that are known to be inactivating of OPCML function. In particular, it is preferred that the variant of OPCML or the fragment thereof does not have a P95R somatic mutation which demonstrates loss of components of domain 1 function, such as intercellular adhesion and cell-matrix binding inhibition on collagen substrates.

It is preferred that the fragment of OPCML, or the variant of the OPCML or fragment thereof possesses at least 50% of the activity of full length human OPCML in inhibiting the proliferation of cancer cells in vitro. It is more preferred if the fragment of OPCML, or the variant of the OPCML or fragment thereof possesses at least 50%, or at least 60%, or at least 70%, or at least 80%, or at least 90%, or at least 100% or more of the activity of full length human OPCML in inhibiting the proliferation of cancer cells in vitro. This can be determined using methods well known in the art and described in the Examples below.

In an embodiment, OPCML activity may be measured by the ability (e.g., of the fragment or variant) to downregulate HER2, HER4, FGFR1, EPHA2 and/or FGFR3. The activity of OPCML may also be defined by downstream functional readouts such as phosphor ERK inactivation or downregulation, and also downregulation of phospho AKT.

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA.

The terms "polypeptide" and "protein" are used interchangeably, and refer to a polymer of amino acid residues. Except when the context requires otherwise, such polymers of amino acid residues may contain natural and/or non-natural amino acid residues. The terms "polypeptide" and "protein" also include post-translationally modified polypeptides and proteins, including, for example, glycosylated, sialylated, acetylated, and/or phosphorylated polypeptides and proteins.

The OPCML, fragment or variant thereof may be prepared using an in vivo or in vitro expression system. Preferably, an expression system is used that provides the polypeptides in a form that is suitable for pharmaceutical use, and such expression systems are known to the skilled person. As is clear to the skilled person, polypeptides of the invention suitable for pharmaceutical use can be prepared using techniques for peptide synthesis.

A nucleic acid molecule encoding the OPCML, fragment or variant thereof, or fusion polypeptide thereof, may be used to transform a host cell or host organism for expression of the desired polypeptide. Suitable hosts or host cells are known to the skilled person, and may be any suitable fungal, prokaryotic or eukaryotic cell or cell line or any suitable fungal, prokaryotic or eukaryotic organism, for example: a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*; a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi; a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica*; an amphibian cell or cell line, such as *Xenopus* oocytes; an insect-derived cell or cell line, such as cells/cell lines derived from lepidoptera, including but not limited to *Spodoptera* SF9 and Sf21 cells or cells/cell lines derived from *Drosophila*, such as Schneider and Kc cells; a plant or plant cell, for example in tobacco plants; and/or a mammalian cell or cell line, for example a cell or cell line derived from a human, a cell or a cell line from mammals including but not limited to CHO-cells, BHK-cells (for example BHK-21 cells) and human cells or cell lines such as HeLa, COS (for example COS-7) and PER.C6® cells; as well as all other hosts or host cells known per se for the expression and production of polypeptides known to the skilled person.

For production on industrial scale, preferred heterologous hosts for the (industrial) production of OPCML, a fragment or variant thereof, or a polypeptide fusion thereof, include strains of *E. coli, Pichia pastoris* and *S. cerevisiae* that are suitable for large scale expression/production/fermentation, and in particular for large scale pharmaceutical (i.e. GMP grade) expression/production/fermentation. Suitable examples of such strains are known to the skilled person. Such strains and production/expression systems are commercially available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are commercially available.

The choice of the specific expression system depends, in part, on the requirement for certain post-translational modifications, more specifically glycosylation. The production of a protein for which glycosylation is desired or required necessitates the use of mammalian expression hosts that have the ability to glycosylate the expressed protein. In this respect, it is clear to the skilled person that the glycosyation pattern obtained (i.e. the kind, number and position of residues attached) will depend on the cell or cell line that is used for the expression. Preferably, either a human cell or cell line is used (i.e. leading to a protein that essentially has a human glycosyation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the described host cells and expression systems may be used in the invention, depending on the desired polypeptide amino acid sequence to be obtained and its desired use. Thus, according to one embodiment, the OPCML, fragment or variant thereof, or polypeptide fusion thereof, is glycosylated. According to an alternative embodiment, it may not be glycosylated.

Thus the OPCML, fragment or variant thereof, or a polypeptide fusion thereof (see below), may be produced in a bacterial cell, in a yeast cell, in an insect cell, in a plant cell, or in a mammalian cell, in particular in a human cell or in a cell of a human cell line, which is suitable for large scale pharmaceutical production.

When expression in a host cell is used to produce the OPCML, fragment or variant thereof, or polypeptide fusion thereof, they can be produced either intracellullarly (e.g. in the cytosol, in the periplasm or in inclusion bodies) and then isolated from the host cells and optionally further purified; or they can be produced extracellularly (e.g. in the medium in which the host cells are cultured) and then isolated from the culture medium and optionally further purified. When eukaryotic host cells are used, extracellular production is usually preferred since this considerably facilitates further isolation and downstream processing.

Bacterial cells such as strains of *E. coli* normally do not secrete proteins extracellularly, except for a few classes of proteins such as toxins and hemolysin, and secretory production in *E. coli* refers to the translocation of proteins across the inner membrane to the periplasmic space. Periplasmic production provides several advantages over cytosolic production. For example, the N-terminal amino acid sequence of the secreted product can be identical to a natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in *E. coli* are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, recombinant strains of bacteria that have been genetically modified so as to secrete a desired protein can be used.

Some preferred promoters for use with host cells include, for expression in *E. coli*: lac promoter (and derivatives thereof such as the lacUV5 promoter); arabinose promoter; left-(PL) and rightward (PR) promoter of phage lambda; promoter of the trp operon; hybrid lac/trp promoters (tac and trc); T7-promoter (more specifically that of T7-phage gene 10) and other T-phage promoters; promoter of the Tn10 tetracycline resistance gene; engineered variants of the above promoters that include one or more copies of an extraneous regulatory operator sequence; for expression in *S. cerevisiae*: constitutive: ADH1 (alcohol dehydrogenase 1), ENO (enolase), CYC1 (cytochrome c iso-1), GAPDH (glyceraldehydes-3-phosphate dehydrogenase), PGK1 (phosphoglycerate kinase), PYK1 (pyruvate kinase); regulated: GAL1,10,7 (galactose metabolic enzymes), ADH2 (alcohol dehydrogenase 2), PHO5 (acid phosphatase), CUP1 (copper metallothionein); heterologous: CaMV (cauliflower mosaic virus 35S promoter); for expression in *Pichia pastoris*: the AOX1 promoter (alcohol oxidase 1); for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1 α) promoter from human, chimpanzee, mouse or rat; the SV40 early promoter; HIV-1 long terminal repeat promoter; and the β-actin promoter.

Some preferred vectors for use with host cells include: vectors for expression in mammalian cells: pMAMneo (Clontech), pcDNA3 (Invitrogen), pMC1neo (Stratagene), pSG5 (Stratagene), EBO-pSV2-neo (ATCC 37593), pBPV-1 (8-2) (ATCC 37110), pdBPV-MMTneo (342-12) (ATCC 37224), pRSVgpt (ATCC37199), pRSVneo (ATCC37198), pSV2-dhfr (ATCC 37146), pUCTag (ATCC 37460) and 1ZD35 (ATCC 37565), as well as viral-based expression systems, such as those based on adenovirus; vectors for expression in bacterial cells: pET vectors (Novagen) and pQE vectors (Qiagen); vectors for expression in yeast or other fungal cells: pYES2 (Invitrogen) and Pichia expression vectors (Invitrogen); vectors for expression in insect cells: pBlueBacII (Invitrogen) and other baculovirus vectors; vectors for expression in plants or plant cells: for example vectors based on cauliflower mosaic virus or tobacco mosaic virus, suitable strains of *Agrobacterium*, or Ti-plasmid based vectors.

Some preferred secretory sequences for use with these host cells include: for use in bacterial cells such as *E. coli*: PelB, Bla, OmpA, OmpC, OmpF, OmpT, StI, PhoA, PhoE, MalE, Lpp, LamB, and the like; TAT signal peptide, hemolysin C-terminal secretion signal; for use in yeast: α-mating factor prepro-sequence, phosphatase (phoI), invertase (Suc), etc.; for use in mammalian cells: indigenous signal in case the target protein is of eukaryotic origin; murine Ig κ-chain V-J2-C signal peptide; etc.

Suitable techniques for transforming a host or host cell of the invention are well known to the skilled person and depend on the intended host cell/host organism and the genetic construct to be used.

After transformation a step for detecting and selecting those host cells or host organisms that have been successfully transformed with the nucleotide sequence/genetic construct of the invention may be performed. This may for instance be a selection step based on a selectable marker present in the genetic construct or a step involving the detection of the OPCML amino acid sequence, e.g. using specific antibodies.

Preferably, the host cells express, or are (at least) capable of expressing (e.g. under suitable conditions), the OPCML, fragment or variant thereof, or polypeptide fusion thereof. To produce/obtain expression of the OPCML, fragment or variant thereof, or polypeptide fusion thereof, the transformed host cell may generally be kept, maintained and/or cultured under conditions such that the polypeptide is expressed/produced. Suitable conditions are known to the skilled person and depend upon the host cell/host organism used, as well as on the regulatory elements that control the expression of the (relevant) nucleotide sequence.

Generally, suitable conditions include the use of a suitable medium, the presence of a suitable source of food and/or suitable nutrients, the use of a suitable temperature, and optionally the presence of a suitable inducing factor or compound (e.g. when the nucleotide sequences are under the control of an inducible promoter); all of which may be selected by the skilled person. Again, under such conditions, the desired polypeptide may be expressed in a constitutive manner, in a transient manner, or only when suitably induced.

It will also be clear to the skilled person that the OPCML, fragment or variant thereof, or polypeptide fusion thereof, may (first) be generated in an immature form, which may then be subjected to post-translational modification, depending on the host cell/host organism used. Also, the OPCML, fragment or variant thereof, or polypeptide fusion thereof, may be glycosylated, again depending on the host cell/host organism used.

The OPCML, fragment or variant thereof, or polypeptide fusion thereof, may then be isolated from the host cell/host organism and/or from the medium in which it was cultivated, using protein isolation and/or purification techniques known per se, such as (preparative) chromatography and/or electrophoresis techniques, differential precipitation techniques, affinity techniques (e.g. using a specific, cleavable amino acid sequence fused with the OPCML, fragment or variant thereof, or polypeptide fusion thereof) and/or preparative immunological techniques (i.e. using antibodies against the polypeptide to be isolated).

Less preferably, the OPCML, fragment or variant thereof, may be made by chemical synthesis. For example, peptides may be synthesized by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesized. Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from Calbiochem-Novabiochem (UK). Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

Nucleic acid molecules encoding the OPCML, fragment or variant thereof, or a polypeptide fusion thereof, may be prepared using methods very well known in the art of molecular biology. For example, many of the techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* ($2^{nd}$ edition, Cold Spring Harbor Laboratory Press, Cold Spring Harbor, N.Y. (1989)), among other places.

In certain embodiments, the OPCML, fragment or variant thereof may be in the form of a fusion molecule in which the OPCML, fragment or variant thereof is attached to a fusion partner to form a fusion protein. Many different types of fusion partners are known in the art. One skilled in the art can select a suitable fusion partner according to the intended use of the fusion protein. Examples of fusion partners include polymers, polypeptides, lipophilic moieties, and succinyl groups. Preferred protein fusion partners include serum albumin and an antibody Fc domain. Preferred polymer fusion partners include, but are not limited to, polyethylene glycol, including polyethylene glycols having branched and/or linear chains. Thus, in certain preferred embodiments, the OPCML polypeptide or fragment or variant thereof may be PEGylated, or may comprise a fusion protein with an Fc fragment.

In various embodiments, oligomerization may offer certain functional advantages to a fusion protein, including, but not limited to, multivalency, increased binding strength, and the combined function of different domains. Accordingly, in certain embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains, and certain immunoglobulin domains. Certain exemplary coiled-coil polypeptide fusion partners include the tetranectin coiled-coil domain; the coiled-coil domain of cartilage oligomeric matrix protein; angiopoietin coiled-coil domains; and leucine zipper domains. Certain exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

In certain embodiments, the fusion partner may be an albumin. Certain exemplary albumins include, but are not limited to, human serum album (HSA) and fragments of HSA that are capable of increasing the serum half-life and/or bioavailability of the polypeptide to which they are fused. In certain embodiments, a fusion partner is an albumin-binding molecule, such as, for example, a peptide that binds albumin or a molecule that conjugates with a lipid or other molecule that binds albumin. In certain embodiments, a fusion molecule comprising HSA is prepared as described, e.g., in U.S. Pat. No. 6,686,179.

Proteins can be linked to an Fc region of an IgG molecule. The Fc region of an IgG molecule refers to the Fc domain of an immunoglobulin of the isotype IgG, as is well known to those skilled in the art. The Fc region of an IgG molecule is that portion of IgG molecule (IgG1, IgG2, IgG3, and IgG4) that is responsible for increasing the in vivo serum half-life of the IgG molecule, typically by avoiding rapid renal clearance. Proteins may be fused adjacent to the Fc region of the IgG molecule, or attached to the Fc region of the IgG molecule via a linker peptide. Use of such linker peptides is well known in protein biochemistry. The Fc region is typically derived from IgG1 or IgG4. An example of a suitable Fc domain is the Fc domain derived from human IgG1 that is contained in the plasmid pFUSE-hIgGie1-Fc1 (InvivoGen).

Therapeutic proteins produced as an Fc-chimera are known in the art. For example, Etanercept, the extracellular domain of TNFR2 combined with an Fc fragment, is a therapeutic polypeptide used to treat autoimmune diseases, such as rheumatoid arthritis.

Fusion to an Fc domain may also induce the formation of a dimeric species. Since we have shown that recombinant OPCML produced in bacteria forms a dimer, this may be useful in certain embodiments. Fc-fusions may also improve efficacy of a therapeutic polypeptide through enhanced stability and by increasing the molecular weight of the molecule, thus reducing the rate of renal clearance.

When the fusion partner is an Fc immunoglobulin domain, the skilled person can select an appropriate Fc domain fusion partner according to the intended use. An Fc fusion partner may be a wild-type Fc found in a naturally occurring antibody, a variant thereof, or a fragment thereof. Non-limiting exemplary Fc fusion partners include Fcs comprising a hinge and the CH2 and CH3 constant domains of a human IgG, for example, human IgG1, IgG2, IgG3, or IgG4. Certain additional Fc fusion partners include, but are not limited to, human IgA and IgM. In certain embodiments, an Fc fusion partner comprises a C237S mutation. In certain embodiments, an Fc fusion partner comprises a hinge, CH2, and CH3 domains of human IgG2 with a P331S mutation, as described in U.S. Pat. No. 6,900,292.

In certain embodiments, the fusion partner may be a polymer, for example, polyethylene glycol (PEG). PEG may comprise branched and/or linear chains. In certain embodiments, a fusion partner comprises a chemically-derivatized polypeptide having at least one PEG moiety attached.

Pegylation is a process whereby polyethylene glycol (PEG) is attached to a protein in order to extend the half-life of the protein in the body. Pegylation of proteins may decrease the dose or frequency of administration of the proteins needed for an optimal activity. (Reviews of the technique are provided in Bhadra et al (2002) *Pharmazie* 57: 5-29 and in Harris et al (2001) *Clin. Pharmacokinet*, 40: 539-551.)

Pegylation of a polypeptide may be carried out by any method known in the art. One skilled in the art can select an appropriate method of pegylating a particular polypeptide, taking into consideration the intended use of the polypeptide. Certain exemplary PEG attachment methods as described, for example, in Malik et al., (1992) *Exp. Hematol.*, 20: 1028-1035; Francis (1992) *Focus on Growth Factors* 3: 4-10; EP 0 401 384; EP 0 154 316; EP 0 401 384; WO 92/16221; and WO 95/34326. Pegylation may be performed via an acylation reaction or an alkylation reaction, resulting in attachment of one or more PEG moieties via acyl or alkyl groups. In certain embodiments, PEG moieties are attached to a polypeptide through the α- or ε-amino group of one or more amino acids, although any other points of attachment known in the art are also contemplated.

Pegylation by acylation typically involves reacting an activated ester derivative of a PEG moiety with a polypeptide. An example of activated PEG ester is PEG esterified to N-hydroxysuccinimide (NHS). As used herein, acylation is contemplated to include, without limitation, the following types of linkages between a polypeptide and PEG: amide, carbamate, and urethane. See, e.g., Chamow, (1994) *Bioconjugate Chem.*, 5: 133-140.

Pegylation by alkylation typically involves reacting a terminal aldehyde derivative of a PEG moiety with a polypeptide in the presence of a reducing agent. Non-limiting exemplary reactive PEG aldehydes include PEG propionaldehyde, which is water stable, and mono C1-C10 alkoxy or aryloxy derivatives thereof (See U.S. Pat. No. 5,252,714).

In certain embodiments, a pegylation reaction results in poly-pegylated polypeptides. In certain embodiments, a pegylation reaction results in mono-, di-, and/or tri-pegylated polypeptides. One skilled in the art can select appropriate pegylation chemistry and reaction conditions to achieve the desired level of pegylation. Further, desired pegylated species may be separated from a mixture containing other pegylated species and/or unreacted starting materials using various purification techniques known in the art, including among others, dialysis, salting-out, ultrafiltration, ion-exchange chromatography, gel filtration chromatography, and electrophoresis.

The fusion partner may be attached, either covalently or non-covalently, to the amino-terminus or the carboxy-terminus of the OPCML, fragment or variant thereof. The attachment may also occur at a location within the OPCML, fragment or variant thereof other than the amino-terminus or the carboxy-terminus, for example, through an amino acid side chain (such as, for example, the side chain of cysteine, lysine, histidine, serine, or threonine).

In either covalent or non-covalent attachment embodiments, a linker may be included between the fusion partner and the OPCML, fragment or variant thereof. Such linkers may be comprised of amino acids and/or chemical moieties. One skilled in the art can select a suitable linker depending on the attachment method used, the intended use of the OPCML, fragment or variant thereof, and the desired spacing between the OPCML, fragment or variant thereof and the fusion partner.

Exemplary methods of covalently attaching a fusion partner to a polypeptide include, but are not limited to, translation of the polypeptide and the fusion partner as a single amino acid sequence, and chemical attachment of the fusion partner to the polypeptide. When the fusion partner and the polypeptide are translated as single amino acid sequence, additional amino acids may be included between the fusion partner and the polypeptide as a linker. In certain embodiments, the linker is glycine-serine ("GS"). In certain embodiments, the linker is selected based on the polynucleotide sequence that encodes it, to facilitate cloning the fusion partner and the polypeptide into a single expression construct (for example, a polynucleotide containing a particular restriction site may be placed between the polynucleotide encoding the fusion partner and the polynucleotide encoding the OPCML, fragment or variant thereof, wherein the polynucleotide containing the restriction site encodes a short amino acid linker sequence).

When the fusion partner and the OPCML, fragment or variant thereof are covalently coupled by chemical means, linkers of various sizes can typically be included during the coupling reaction. One skilled in the art can select a suitable method of covalently attaching a fusion partner to a polypeptide depending, for example, on the identity of the fusion partner and the particular use intended for the fusion molecule. One skilled in the art can also select a suitable linker type and length, if one is desired.

Exemplary methods of non-covalently attaching a fusion partner to a polypeptide include, but are not limited to, attachment through a binding pair. Exemplary binding pairs include, but are not limited to, biotin and avidin or streptavidin, an antibody and its antigen, etc. Again, one skilled in the art can select a suitable method of non-covalently attaching a fusion partner to a polypeptide depending, for example, on the identity of the fusion partner and the particular use intended for the fusion molecule. The selected non-covalent attachment method should be suitable for the conditions under which the fusion molecule will be used, taking into account, for example, the pH, salt concentrations, and temperature.

It is appreciated that the compound comprising or consisting of the OPCML polypeptide or fragment or variant thereof, of the fusion thereof, or nucleic acid molecule encoding the OPCML polypeptide or fragment or variant, or polypeptide fusion thereof, may be formulated as a nanoparticle. Nanoparticles are a colloidal carrier system that has been shown to improve the efficacy of an encapsulated drug by prolonging the serum half-life. Polyalkylcyanoacrylates (PACAs) nanoparticles are a polymer colloidal drug delivery system that is in clinical development (described, for example, by Stella et at (2000) J. Pharm. Sci., 89: 1452-1464; Brigger et at (2001) Int. J. Pharm 214: 37-42; Calvo et al (2001) Pharm. Res. 18: 1157-1166; and Li et al (2001) Bio. Pharm. Bull. 24: 662-665). Biodegradable poly(hydroxyl acids), such as the copolymers of poly(lactic acid) (PLA) and poly(lactic-co-glycolide) (PLGA) are being extensively used in biomedical applications and have received FDA approval for certain clinical applications. In addition, PEG-PLGA nanoparticles have many desirable carrier features including (i) that the agent to be encapsulated comprises a reasonably high weight fraction (loading) of the total carrier system; (ii) that the amount of agent used in the first step of the encapsulation process is incorporated into the final carrier (entrapment efficiency) at a reasonably high level; (iii) that the carrier has the ability to be freeze-dried and reconstituted in solution without aggregation; (iv) that the carrier be biodegradable; (v) that the carrier system be of small size; and (vi) that the carrier enhances the particles persistence.

Nanoparticles may be synthesized using virtually any biodegradable shell known in the art. In one embodiment, a polymer, such as poly(lactic-acid) (PLA) or poly(lactic-co-glycolic acid) (PLGA) is used. Such polymers are biocompatible and biodegradable, and are subject to modifications that desirably increase the photochemical efficacy and circulation lifetime of the nanoparticle. In one embodiment, the polymer is modified with a terminal carboxylic acid group (COOH) that increases the negative charge of the particle and thus limits the interaction with negatively charged nucleic acids. Nanoparticles may also be modified with polyethylene glycol (PEG), which also increases the half-life and stability of the particles in circulation. Alternatively, the COOH group may be converted to an N-hydroxysuccinimide (NHS) ester for covalent conjugation to amine-modified compounds.

Other protein modifications to stabilize a polypeptide, for example to prevent degradation, as are well known in the art may also be employed. Specific amino acids may be modified to reduce cleavage of the polypeptide in vivo; typically, N- or C-terminal regions are modified to reduce protease activity on the polypeptide. A stabilizing modification is any modification known in the art or described herein capable of stabilizing a protein, enhancing the in vitro half life of a protein, enhancing circulatory half life of a protein and/or reducing proteolytic degradation of a protein. For example, polypeptides may be linked to the serum albumin or a derivative of albumin. Methods for linking polypeptides to albumin or albumin derivatives are well known in the art (e.g., U.S. Pat. No. 5,116,944).

It is appreciated that the compound comprising or consisting of the OPCML polypeptide or fragment or variant thereof, or nucleic acid molecule encoding the OPCML polypeptide or fragment or variant, will typically be formulated for administration to an individual as a pharmaceutical composition, i.e. together with a pharmaceutically acceptable carrier, diluent or excipient.

By "pharmaceutically acceptable" is included that the formulation is sterile and pyrogen free. Suitable pharmaceutical carriers, diluents and excipients are well known in the art of pharmacy. The carrier(s) must be "acceptable" in the sense of being compatible with the compound and not deleterious to the recipients thereof. Typically, the carriers will be water or saline which will be sterile and pyrogen free; however, other acceptable carriers may be used.

In an embodiment, the pharmaceutical compositions or formulations of the invention are formulated for parenteral administration, more particularly for intravenous administration. In a preferred embodiment, the pharmaceutical composition is suitable for intravenous administration to a patient, for example by injection.

Thus, typically and preferably, the compound is administered intravenously or by intraperitoneal administration to the patient.

Suitably and equally preferably, the compound is administered as an infusion or as a bolus injection.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

In an alternative preferred embodiment, the pharmaceutical composition is suitable for topical administration to a patient.

Preferably, the formulation is a unit dosage containing a daily dose or unit, daily sub-dose or an appropriate fraction thereof, of the active ingredient.

The compound may be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

We have tested 0.5, 1, 2, 5 and 10 µM of recombinant full length human OPCML in vitro, and there is a linear dose response which has not yet peaked. We see inhibition of cell growth from 2 µm and frank cell death at 5-10 µM in 6/7 ovarian cancer cell lines and 2/2 breast cancer cell lines (both HER2 positive and HER2 negative). The physician skilled in the art will be able to identify suitable doses based upon this information and their skill in the art.

In human therapy, the compound will generally be administered in admixture with a suitable pharmaceutical excipient, diluent or carrier selected with regard to the intended route of administration and standard pharmaceutical practice.

For example, the compound may be administered orally, buccally or sublingually in the form of tablets, capsules, ovules, elixirs, solutions or suspensions, which may contain flavouring or colouring agents, for immediate-, delayed- or controlled-release applications. The compound may also be administered via intracavernosal injection.

Suitable tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compound can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of a compound will usually be from 1 to 1,000 mg per adult (i.e. from about 0.015 to 15 mg/kg), administered in single or divided doses.

Thus, for example, the tablets or capsules of the compound may contain from 1 mg to 1,000 mg of active agent for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compound can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of an antibody and a suitable powder base such as lactose or starch. Such formulations may be particularly useful for treating solid tumours of the lung.

Aerosol or dry powder formulations are preferably arranged so that each metered dose or "puff" contains at least 1 mg of the compound for delivery to the patient. It will be appreciated that the overall daily dose with an aerosol will vary from patient to patient, and may be administered in a single dose or, more usually, in divided doses throughout the day.

Alternatively, the compound can be administered in the form of a suppository or pessary, particularly for treating or targeting colon, rectal or prostate tumours.

The compound may also be administered by the ocular route. For ophthalmic use, the compound can be formulated as, e.g., micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum. Such formulations may be particularly useful for treating cancers of the eye, such as retinoblastoma.

The compound may be applied topically in the form of a lotion, solution, cream, ointment or dusting powder, or may be transdermally administered, for example, by the use of a skin patch. For application topically to the skin, the compound can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water. Such formulations may be particularly useful for treating skin cancers.

For skin cancers, the compound can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with the compound or can simply act as "bullets" that generate pores in the skin through which the compound can enter.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier. Such formulations may be particularly useful for treating cancers of the mouth and throat.

In an embodiment, when the compound is a polypeptide, it may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

The antibody can be administered by a surgically implanted device that releases the drug directly to the required site, for example, into the eye to treat ocular tumours. Such direct application to the site of disease achieves effective therapy without significant systemic side-effects.

An alternative method for delivery of polypeptides is the ReGel injectable system that is thermo-sensitive. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Polypeptides can also be delivered orally. For example, the process employs a natural process for oral uptake of vitamin $B_{12}$ in the body to co-deliver proteins and peptides. By riding the vitamin $B_{12}$ uptake system, the protein or peptide can move through the intestinal wall. Complexes are synthesised between vitamin $B_{12}$ analogues and the drug that retain both significant affinity for intrinsic factor (IF) in the vitamin $B_{12}$ portion of the complex and significant bioactivity of the drug portion of the complex.

Polynucleotides may be administered by any effective method, for example, parenterally (e.g. intravenously, subcutaneously, intramuscularly) or by oral, nasal or other means which permit the polynucleotides to access and circulate in the patient's bloodstream. Polynucleotides administered systemically preferably are given in addition to locally administered polynucleotides, but also have utility in the absence of local administration. A dosage in the range of from about 0.1 to about 10 grams per administration to an adult human generally will be effective for this purpose.

The polynucleotide may be administered as a suitable genetic construct as is described below and delivered to the patient where it is expressed. Typically, the polynucleotide in the genetic construct is operatively linked to a promoter which can express the compound in the cell. The genetic constructs of the invention can be prepared using methods well known in the art, for example in Sambrook et al (2001).

Although genetic constructs for delivery of polynucleotides can be DNA or RNA, it is preferred if they are DNA.

Preferably, the genetic construct is adapted for delivery to a human cell.

Means and methods of introducing a genetic construct into a cell in an animal body are known in the art. For example, the constructs of the invention may be introduced into cells by any convenient method, for example methods involving retroviruses, so that the construct is inserted into the genome of the cell. For example, in Kuriyama et al (1991, *Cell Struc. and Func.* 16, 503-510), purified retroviruses are administered. Retroviral DNA constructs comprising a polynucleotide as described above may be made using methods well known in the art. To produce active retrovirus from such a construct it is usual to use an ecotropic psi2 packaging cell line grown in Dulbecco's modified Eagle's medium (DMEM) containing 10% foetal calf serum (FCS). Transfection of the cell line is conveniently by calcium phosphate co-precipitation, and stable transformants are selected by addition of G418 to a final concentration of 1 mg/ml (assuming the retroviral construct contains a $neo^R$ gene). Independent colonies are isolated and expanded and the culture supernatant removed, filtered through a 0.45 µm pore-size filter and stored at −70° C. For the introduction of the retrovirus into tumour cells, for example, it is convenient to inject directly retroviral supernatant to which 10 µg/ml Polybrene has been added. For tumours exceeding 10 mm in diameter it is appropriate to inject between 0.1 ml and 1 ml of retroviral supernatant; preferably 0.5 Al.

Alternatively, as described in Culver et al (1992, *Science* 256, 1550-1552), cells which produce retroviruses may be injected. The retrovirus-producing cells so introduced are engineered to actively produce retroviral vector particles so that continuous production of the vector occurs within the tumour mass in situ.

Targeted retroviruses are also available for use in the invention; for example, sequences conferring specific binding affinities may be engineered into pre-existing viral env genes (see Miller & Vile (1995) *Faseb J.* 9, 190-199, for a review of this and other targeted vectors for gene therapy).

Other methods involve simple delivery of the construct into the cell for expression therein either for a limited time or, following integration into the genome, for a longer time. An example of the latter approach includes liposomes (Nassander et al (1992) *Cancer Res.* 52, 646-653).

Other methods of delivery include adenoviruses carrying external DNA via an antibody-polylysine bridge (see Curiel (1993) *Prog. Med. Virol.* 40, 1-18) and transferrin-polycation conjugates as carriers (Wagner et a. (1990) *Proc. Natl. Acad. Sci. USA* 87, 3410-3414). In the first of these methods a polycation-antibody complex is formed with the DNA construct or other genetic construct of the invention, wherein the antibody is specific for either wild-type adenovirus or a variant adenovirus in which a new epitope has been introduced which binds the antibody. The polycation moiety binds the DNA via electrostatic interactions with the phosphate backbone. The adenovirus, because it contains unaltered fibre and penton proteins, is internalised into the cell and carries into the cell with it the DNA construct of the invention. It is preferred if the polycation is polylysine.

In an alternative method, a high-efficiency nucleic acid delivery system that uses receptor-mediated endocytosis to carry DNA macromolecules into cells is employed. This is accomplished by conjugating the iron-transport protein transferrin to polycations that bind nucleic acids. Human transferrin, or the chicken homologue conalbumin, or combinations thereof is covalently linked to the small DNA-binding protein protamine or to polylysines of various sizes through a disulphide linkage. These modified transferrin molecules maintain their ability to bind their cognate receptor and to mediate efficient iron transport into the cell. The transferrin-polycation molecules form electrophoretically stable complexes with DNA constructs or other genetic constructs of the invention independent of nucleic acid size (from short oligonucleotides to DNA of 21 kilobase pairs). When complexes of transferrin-polycation and the DNA constructs or other genetic constructs of the invention are supplied to the tumour cells, a high level of expression from the construct in the cells is expected.

High-efficiency receptor-mediated delivery of the DNA constructs or other genetic constructs of the invention using the endosome-disruption activity of defective or chemically inactivated adenovirus particles produced by the methods of Cotten et a (1992) *Proc. Natl. Acad. Sci. USA* 89, 6094-6098 may also be used. This approach appears to rely on the fact that adenoviruses are adapted to allow release of their DNA from an endosome without passage through the lysosome, and in the presence of, for example transferrin linked to the DNA construct or other genetic construct of the invention, the construct is taken up by the cell by the same route as the adenovirus particle. This approach has the advantages that there is no need to use complex retroviral constructs; there is no permanent modification of the genome as occurs with retroviral infection; and the targeted expression system is coupled with a targeted delivery system, thus reducing toxicity to other cell types.

It will be appreciated that "naked DNA" and DNA complexed with cationic and neutral lipids may also be useful in introducing the DNA of the invention into cells of the individual to be treated. Non-viral approaches to gene therapy are described in Ledley (1995, *Human Gene Therapy* 6, 1129-1144).

For cancers of specific tissues it may be useful to use tissue-specific promoters in the vectors encoding a polynucleotide. This is because the targeted genes are only expressed, or selectively expressed, in the tumour endothelium.

Targeted delivery systems are also known, such as the modified adenovirus system described in WO 94/10323, wherein, typically, the DNA is carried within the adenovirus, or adenovirus-like, particle. Michael et at (1995) *Gene Therapy* 2: 660-668, describes modification of adenovirus to add a cell-selective moiety into a fibre protein. Mutant adenoviruses which replicate selectively in p53-deficient human tumour cells, such as those described in Bischoff et al (1996) *Science* 274: 373-376 are also useful for delivering genetic constructs to a cell. Other suitable viruses, viral vectors or virus-like particles include lentivirus and lentiviral vectors, HSV, adeno-assisted virus (AAV) and AAV-based vectors, vaccinia and parvovirus.

Methods of delivering polynucleotides to a patient are well known to a person of skill in the art and include the use of immunoliposomes, viral vectors (including vaccinia, modified vaccinia, adenovirus and adeno-associated viral (AAV) vectors), and by direct delivery of DNA, e.g. using a gene-gun and electroporation. Furthermore, methods of delivering polynucleotides to a target tissue of a patient for treatment are also well known in the art.

Methods of targeting and delivering therapeutic agents directly to specific regions of the body are well known to a person of skill in the art.

For example, U.S. Pat. No. 6,503,242 describes an implanted catheter apparatus for delivering therapeutic agents directly to the hippocampus. Methods of targeting and delivering agents to the brain can be used for the treatment of solid tumours of the brain. In one embodiment, therapeutic agents including vectors can be distributed throughout a wide region of the CNS by injection into the cerebrospinal fluid, e.g., by lumbar puncture (See e.g., Kapadia et al (1996) *Neurosurg* 10: 585-587). Alternatively, precise delivery of the therapeutic agent into specific sites of the brain can be conducted using stereotactic microinjection techniques. For example, the subject being treated can be placed within a stereotactic frame base (MRI-compatible) and then imaged using high resolution MRI to determine the three-dimensional positioning of the particular region to be treated. The MRI images can then be transferred to a computer having the appropriate stereotactic software, and a number of images are used to determine a target site and trajectory for microinjection of the therapeutic agent. The software translates the trajectory into three-dimensional coordinates that are precisely registered for the stereotactic frame. In the case of intracranial delivery, the skull will be exposed, burr holes will be drilled above the entry site, and the stereotactic apparatus used to position the needle and ensure implantation at a predetermined depth. The therapeutic agent can be delivered to regions of the CNS such as the hippocampus, cells of the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), or combinations, thereof. In another embodiment, the therapeutic agent is delivered using other delivery methods suitable for localised delivery, such as localised permeation of the blood-brain barrier. US 2005/0025746 describes delivery systems for localised delivery of an adeno-associated virus vector (AAV) vector encoding a therapeutic agent to a specific region of the brain.

When a therapeutic agent for the treatment of a solid cancer of, for example, the brain, is encoded by a polynucleotide, it may be preferable for its expression to be under the control of a suitable tissue-specific promoter. Central nervous system (CNS) specific promoters such as, neuron-specific promoters (e.g., the neurofilament promoter (Byrne and Ruddle (1989) *Proc. Natl. Acad. Sci. USA* 86: 5473-5477) and glial specific promoters (Morii et al (1991) *Biochem. Biophys Res. Commun.* 175: 185-191)) are preferably used for directing expression of a polynucleotide preferentially in cells of the CNS. Preferably, the promoter is tissue specific and is essentially not active outside the central nervous system, or the activity of the promoter is higher in the central nervous system than in other cells or tissues. For example, the promoter may be specific for the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), or combinations, thereof. The promoter may be specific for particular cell types, such as neurons or glial cells in the CNS. If it is active in glial cells, it may be specific for astrocytes, oligodendrocytes, ependymal cells, Schwann cells, or microglia. If it is active in neurons, it may be specific for particular types of neurons, e.g., motor neurons, sensory neurons, or interneurons. The promoter may be specific for cells in particular regions of the brain, for example, the cortex, stratium, nigra and hippocampus.

Suitable neuronal specific promoters include, but are not limited to, neuron specific enolase (NSE; Olivia et al (1991) *Genomics* 10: 157-165; GenBank Accession No: X51956), and human neurofilament light chain promoter (NEFL; Rogaev et al (1992) *Hum. Mol. Genet.* 1: 781; GenBank Accession No: L04147). Glial specific promoters include, but are not limited to, glial fibrillary acidic protein (GFAP) promoter (Morii et al (1991); GenBank Accession No: M65210), S100 promoter (Morii et al (1991); GenBank Accession No: M65210) and glutamine synthase promoter (Van den et al (1991) *Biochem. Biophys. Acta.* 2: 249-251; GenBank Accession No: X59834). In a preferred embodiment, the gene is flanked upstream (i.e., 5') by the neuron specific enolase (NSE) promoter. In another preferred embodiment, the gene of interest is flanked upstream (i.e., 5') by the elongation factor 1 alpha (EF) promoter. A hippocampus specific promoter that might be used is the hippocampus specific glucocorticoid receptor (GR) gene promoter.

Alternatively, for treatment of cancer of the heart, Svensson et at (1999) describes the delivery of recombinant genes to cardiomyocytes by intramyocardial injection or intracoronary infusion of cardiotropic vectors, such as recombinant adeno-associated virus vectors, resulting in transgene expression in murine cardiomyocytes in vivo (Svensson et al (1999) "Efficient and stable transduction of cardiomyocytes after intramyocardial injection or intracoronary perfusion with recombinant adeno-associated virus vectors." *Circulation.* 99: 201-5). Melo et al review gene and cell-based therapies for heart disease (Melo et al (2004) "Gene and cell-based therapies for heart disease." *FASEB J.* 18(6): 648-63). An alternative preferred route of administration is via a catheter or stent. Stents represent an attractive alternative for localized gene delivery, as they provide a platform for prolonged gene elution and efficient transduction of opposed arterial walls. This gene delivery strategy has the potential to decrease the systemic spread of the viral vectors and hence a reduced host immune response. Both synthetic and naturally occurring stent coatings have shown potential to allow prolonged gene elution with no significant adverse reaction (Sharif et al (2004) "Current status of catheter- and stent-based gene therapy." *Cardiovasc Res.* 64(2): 208-16).

It may also be desirable to be able to temporally regulate expression of the polynucleotide in the cell. Thus, it may be desirable that expression of the polynucleotide is directly or indirectly (see below) under the control of a promoter that may be regulated, for example by the concentration of a small molecule that may be administered to the patient when it is desired to activate or, more likely, repress (depending upon whether the small molecule effects activation or repression of the said promoter) expression of the antibody from the polynucleotide. This may be of particular benefit if the expression construct is stable, i.e., capable of expressing the compound (in the presence of any necessary regulatory molecules), in the cell for a period of at least one week, one, two, three, four, five, six, eight months or one or more years. Thus the polynucleotide may be operatively linked to a regulatable promoter. Examples of regulatable promoters include those referred to in the following papers: Rivera et al (1999) *Proc Natl Acad Sci USA* 96(15), 8657-62 (control by rapamycin, an orally bioavailable drug, using two separate adenovirus or adeno-associated virus (AAV) vectors, one encoding an inducible human growth hormone (hGH) target gene, and the other a bipartite rapamycin-regulated transcription factor); Magari et al (1997) *J Clin Invest* 100(11), 2865-72 (control by rapamycin); Bueler (1999) *Biol Chem* 380(6), 613-22 (review of adeno-associated viral vectors); Bohl et al (1998) *Blood* 92(5), 1512-7 (control by doxycycline in adeno-associated vector); Abruzzese et at (1996) *J Mol Med* 74(7), 379-92 (review of induction factors, e.g. hormones, growth factors, cytokines, cytostatics, irradiation, heat shock and associated responsive elements).

It is preferred that the patient to be treated is a human patient. For veterinary use, however, the compound is typically administered as a suitably acceptable formulation in accordance with normal veterinary practice and the veterinary surgeon will determine the dosing regimen and route of administration which will be most appropriate for a particular animal.

The cancer to be treated may be selected from ovarian cancer, breast cancer, renal cancer, gastrointestinal cancer, brain cancer, lung cancer, nasopharyngeal cancer, esophageal cancer, gastric cancer, colon cancer, liver cancer, cervical cancer, prostate cancer, non-Hodgkin lymphoma, Hodgkin lymphoma, and nasal NK/T-cell lymphoma.

It is preferred, however, that the cancer to be treated is ovarian cancer or breast cancer, most preferably ovarian cancer.

In an embodiment, the invention further comprises administering to the patient at least one additional anticancer agent. The method may comprise administering to the individual a pharmaceutical composition containing the compound comprising or consisting of the OPCML polypeptide or fragment or variant thereof, or nucleic acid molecule which encodes the OPCML polypeptide or fragment or variant, and the further anticancer agent. However, it is appreciated that the compound and the further anticancer agent may be administered separately, for instance by separate routes of administration. Thus it is appreciated that the compound and the at least one further anticancer agent can be administered sequentially or (substantially) simultaneously. They may be administered within the same pharmaceutical formulation or medicament or they may be formulated and administered separately.

In an embodiment of the medical uses, the medicament containing the compound may also comprise the at least one further anticancer agent.

In another embodiment of the medical uses, the individual to be treated may be one who is administered at least one further anticancer agent. It is appreciated that the individual may be administered the further anticancer agent at the same time as the medicament containing the compound comprising or consisting of the OPCML polypeptide or fragment or variant thereof, or nucleic acid molecule which encodes the OPCML polypeptide or fragment or variant, although the individual may have been (or will be) administered the further anticancer agent before (or after) receiving the medicament containing the compound.

The further anticancer agent may be selected from alkylating agents including nitrogen mustards such as mechlorethamine ($HN_2$), cyclophosphamide, ifosfamide, melphalan (L-sarcolysin) and chlorambucil; ethylenimines and methylmelamines such as hexamethylmelamine, thiotepa; alkyl sulphonates such as busulphan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin); natural products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; and biological response modifiers such as interferon alphenomes; miscellaneous agents including platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p'-DDD) and aminoglutethimide; taxol and analogues/derivatives; cell cycle inhibitors; proteosome inhibitors such as Bortezomib (Velcade®); signal transductase (e.g. tyrosine kinase) inhibitors such as Imatinib (Glivec®), COX-2 inhibitors, and hormone agonists/antagonists such as flutamide and tamoxifen.

The clinically used anticancer agents are typically grouped by mechanism of action: Alkylating agents, Topoisomerase I inhibitors, Topoisomerase II inhibitors, RNA/DNA antimetabolites, DNA antimetabolites and Antimitotic agents. The US NIH/National Cancer Institute website lists 122 compounds (http://dtp.nci.nih.gov/docs/cancer/searches/standard_mechanism.html), all of which may be used in conjunction with the compound. They include Alkylating agents including Asaley, AZQ, BCNU, Busulfan, carboxyphthalatoplatinum, CBDCA, CCNU, CHIP, chlorambucil, chlorozotocin, cis-platinum, clomesone, cyanomorpholino-doxorubicin, cyclodisone, dianhydrogalactitol, fluorodopan, hepsulfam, hycanthone, melphalan, methyl CCNU, mitomycin C, mitozolamide, nitrogen mustard, PCNU, piperazine, piperazinedione, pipobroman, porfiromycin, spirohydantoin mustard, teroxirone, tetraplatin, thiotepa, triethylenemeamine, uracil nitrogen mustard, Yoshi-864; anitmitotic agents including allocolchicine, Halichondrin B, colchicine, colchicine derivative, dolastatin 10, maytansine, rhizoxin, taxol, taxol derivative, thiocolchicine, trityl cysteine, vinblastine sulphate, vincristine sulphate; Topoisomerase I Inhibitors including camptothecin, camptothecin, Na salt, aminocamptothecin, 20 camptothecin derivatives, morpholinodoxorubicin; Topoisomerase II Inhibitors including doxorubicin, amonafide, m-AMSA, anthrapyrazole derivative, pyrazoloacridine, bisantrene HCL, daunorubicin, deoxydoxorubicin, mitoxantrone, menogaril, N,N-dibenzyl daunomycin, oxanthrazole, rubidazone, VM-26, VP-16; RNA/DNA antimetabolites including L-alanosine, 5-azacytidine, 5-fluorouracil, acivicin, 3 aminopterin derivatives, an antifol, Baker's soluble antifol, dichlorallyl lawsone, brequinar, ftorafur (pro-drug), 5,6-dihydro-5-azacytidine, methotrexate, methotrexate derivative, N-(phosphonoacetyl)-L-aspartate (PALA), pyrazofurin, trimetrexate; DNA antimetabolites including, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole, hydroxyurea, inosine glycodialdehyde, macbecin II, pyrazoloimidazole, thioguanine and thiopurine.

It is, however, preferred that the at least one further anticancer agent is selected from cisplatin, carboplatin, 5-flurouracil, paclitaxel, mitomycin C, doxorubicin, gemcitabine, tomudex, pemetrexed, methotrexate, irinotecan, oxaliplatin, or combinations thereof.

When the further anticancer agent or combination of agents has been shown to be particularly effective for a specific tumour type, it may be preferred that the compound is used in combination with that further anticancer agent(s) to treat that specific tumour type.

In one preferred embodiment, if the cancer is one in which HER2 is upregulated and/or in which HER2 mediated-signaling is upregulated, the additional anticancer agent may be a HER2 inhibitor.

In another embodiment, if the cancer is one in which FGFR1 is upregulated and/or in which FGFR1 mediated-signaling is upregulated, the additional anticancer agent is an FGFR1 inhibitor.

In yet another embodiment, if the cancer is one in which HER4 is upregulated and/or in which HER4 mediated-signaling is upregulated, the additional anticancer agent is a HER4 inhibitor.

In a still further embodiment, if the cancer is one in which FGFR3 is upregulated and/or in which FGFR3 mediated-signaling is upregulated, the additional anticancer agent is an FGFR3 inhibitor.

In a still yet further embodiment, if the cancer is one in which EPHA2 is upregulated and/or in which EPHA2 mediated-signaling is upregulated, the additional anticancer agent is an EPHA2 inhibitor.

Suitable inhibitors of HER2, HER4, FGFR1, EPHA2 and FGFR3 include antibodies that specifically or selectively bind to HER2, HER4, FGFR1, EPHA2 and FGFR3, respectively. Other inhibitors of HER2, HER4, FGFR1, EPHA2 and FGFR3 include siRNA, antisense polynucleotides and ribozyme molecules that are specific for polynucleotides encoding the respective HER2, HER4, FGFR1, EPHA2 and FGFR3 polypeptide, and which prevent their expression. Other inhibitors include small molecule inhibitors of the tyrosine kinase receptors, such as lapatinib, which typically act on the C-terminal kinase domain, inhibiting autophosphorylation and activation of the receptor.

It is appreciated that polynucleotide inhibitors of HER2, HER4, FGFR1, EPHA2 and FGFR3 may be administered directly, or may be administered in the form of a polynucleotide that encodes the inhibitor. Thus, as used herein, unless the context demands otherwise, by administering to the individual an inhibitor of HER2, HER4, FGFR1, EPHA2 and FGFR3 which is a polynucleotide, we include the meanings of administering the inhibitor directly, or administering a polynucleotide that encodes the inhibitor, typically in the form of a vector. Similarly, as used herein, unless the context demands otherwise, by a medicament or a composition comprising an inhibitor of HER2, HER4, FGFR1, EPHA2 and/or FGFR3 which is a polynucleotide, we include the meanings that the medicament or composition comprises the inhibitor itself, or comprises a polynucleotide that encodes the inhibitor.

Antibodies that specifically or selectively bind to HER2, HER4, FGFR1, EPHA2 or FGFR3 are also referred to as anti-HER2, anti-HER4, anti-FGFR1, anti-EPHA2 and anti-FGFR3 antibodies. Such antibodies will bind their target with a greater affinity than for an irrelevant polypeptide, such as human serum albumin (HSA). Preferably, the antibody binds the HER2, HER4, FGFR1, EPHA2 or FGFR3 with at least 5, or at least 10 or at least 50 times greater affinity than for the irrelevant polypeptide. More preferably, the antibody molecule binds the HER2, HER4, FGFR1, EPHA2 or FGFR3 with at least 100, or at least 1,000, or at least 10,000 times greater affinity than for the irrelevant polypeptide. Such binding may be determined by methods well known in the art, such as one of the Biacore® systems.

It is preferred if the antibodies have an affinity for HER2, HER4, FGFR1, EPHA2 or FGFR3 of at least $10^{-7}$ M and more preferably $10^{-8}$ M, although antibodies with higher affinities, e.g. $10^{-9}$ M, or higher, may be even more preferred.

Typically, the antibody that selectively binds HER2, HER4, FGFR1, EPHA2 or FGFR3 polypeptide binds to the extracellular region of the polypeptide.

Preferably, when the antibody is administered to an individual, the antibody binds to the target HER2, HER4, FGFR1, EPHA2 or FGFR3 or to the specified portion thereof with a greater affinity than for any other molecule in the individual. Preferably, the antibody binds to (a specified portion of) the HER2, HER4, FGFR1, EPHA2 or FGFR3 with at least 2, or at least 5, or at least 10 or at least 50 times greater affinity than for any other molecule in the individual. More preferably, the agent binds the HER2, HER4, FGFR1, EPHA2 or FGFR3 (at the specific domain) with at least 100, or at least 1,000, or at least 10,000 times greater affinity than any other molecule in the individual. Preferably, the antibody molecule selectively binds the HER2, HER4, FGFR1, EPHA2 or FGFR3 without significantly binding other polypeptides in the body, such as for example other RTKs, although in practice there may be some cross reactivity, especially between HER2 and HER4, and FGFR1, EPHA2 and FGFR3.

The term "antibody" or "antibody molecule" as used herein includes but is not limited to polyclonal, monoclonal, chimeric, single chain, Fab fragments and fragments produced by a Fab expression library. Such fragments include fragments of whole antibodies which retain their binding activity for a target substance, Fv, F(ab') and F(ab')2 fragments, as well as single chain antibodies (scFv), fusion proteins and other synthetic proteins which comprise the antigen-binding site of the antibody. The term also includes antibody-like molecules which may be produced using phage-display techniques or other random selection techniques for molecules which bind to the specified polypeptide or to particular regions of it. Thus, the term antibody includes all molecules which contain a structure, preferably a peptide structure, which is part of the recognition site (i.e. the part of the antibody that binds or combines with the epitope or antigen) of a natural antibody. Furthermore, the antibodies and fragments thereof may be humanised antibodies, which are now well known in the art.

By antibodies we also include Nanobodies® (Ablynx) which are antibody-derived therapeutic proteins that contain the structural and functional properties of naturally-occurring heavy-chain antibodies. The Nanobody® technology was developed following the discovery that camelidae (camels and llamas) possess fully functional antibodies that lack light chains. These heavy-chain antibodies contain a single variable domain (VHH) and two constant domains ($C_H2$ and $C_H3$). The cloned and isolated VHH domain is a perfectly stable polypeptide harbouring the full antigen-binding capacity of the original heavy-chain antibody. These VHH domains with their unique structural and functional properties form the basis of Nanobodies®. They combine the advantages of conventional antibodies (high target specificity, high target affinity and low inherent toxicity) with important features of small molecule drugs (the ability to inhibit enzymes and access receptor clefts). Furthermore, they are stable, have the potential to be administered by means other than injection, are easier to manufacture, and can be humanised. (See, for example U.S. Pat. Nos. 5,840, 526; 5,874,541; 6,005,079, 6,765,087; EP 1 589 107; WO 97/34103; WO97/49805; U.S. Pat. Nos. 5,800,988; 5,874, 541 and 6,015,695).

By "ScFv molecules" we mean molecules wherein the $V_H$ and $V_L$ partner domains are linked via a flexible oligopeptide. Engineered antibodies, such as ScFv antibodies, can be made using the techniques and approaches long known in the art. The advantages of using antibody fragments, rather than whole antibodies, are several-fold. The smaller size of the fragments may lead to improved pharmacological properties, such as better penetration to the target site. Effector functions of whole antibodies, such as complement binding, are removed. Fab, Fv, ScFv and dAb antibody fragments can all be expressed in and secreted from *E. coli*, thus allowing the facile production of large amounts of the fragments. Whole antibodies, and F(ab')$_2$ fragments are "bivalent". By "bivalent" we mean that the antibodies and F(ab')$_2$ fragments have two antigen combining sites. In contrast, Fab, Fv, ScFv and dAb fragments are monovalent, having only one antigen combining site.

If polyclonal antibodies are desired, a selected mammal (e.g., mouse, rabbit, goat, horse, etc) is immunised with an immunogenic polypeptide bearing a desired epitope(s), optionally haptenised to another polypeptide. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. Serum from the immunised animal is collected and treated according to known procedures. If serum containing polyclonal antibodies to the desired epitope contains antibodies to other antigens, the polyclonal antibodies can be purified by immunoaffinity chromatography. Techniques for producing and processing polyclonal antisera are well known in the art.

Monoclonal antibodies directed against entire polypeptides or particular epitopes thereof can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against the polypeptides listed above can be screened for various properties; i.e., for isotype and epitope affinity. Monoclonal antibodies may be prepared using any of the well known techniques which provides for the production of antibody molecules by continuous cell lines in culture.

It is preferred if the antibody is a monoclonal antibody. In some circumstance, particularly if the antibody is going to be administered repeatedly to a human patient, it is preferred if the monoclonal antibody is a human monoclonal antibody or a humanised monoclonal antibody, which are suitable for administration to humans without engendering an immune response by the human against the administered immunoglobulin. Suitably prepared non-human antibodies can be "humanised" in known ways, for example by inserting the CDR regions of mouse antibodies into the framework of human antibodies. Humanised antibodies can be made using the techniques and approaches described in Verhoeyen et al (1988) *Science*, 239, 1534-1536, and in Kettleborough et al, (1991) *Protein Engineering*, 14(7), 773-783. In some instances, Fv framework residues of the human immunoglobulin are replaced by corresponding non-human residues. In general, the humanised antibody will contain variable domains in which all or most of the CDR regions correspond to those of a non-human immunoglobulin, and framework regions which are substantially or completely those of a human immunoglobulin consensus sequence.

Completely human antibodies may be produced using recombinant technologies. Typically large libraries comprising billions of different antibodies are used. In contrast to the previous technologies employing chimerisation or humanisation of e.g. murine antibodies this technology does not rely on immunisation of animals to generate the specific antibody. Instead the recombinant libraries comprise a huge number of pre-made antibody variants wherein it is likely that the library will have at least one antibody specific for any antigen. Thus, using such libraries, an existing antibody having the desired binding characteristics can be identified. In order to find the good binder in a library in an efficient manner, various systems where phenotype i.e. the antibody or antibody fragment is linked to its genotype i.e. the encoding gene have been devised. The most commonly used such system is the so called phage display system where antibody fragments are expressed, displayed, as fusions with phage coat proteins on the surface of filamentous phage particles, while simultaneously carrying the genetic information encoding the displayed molecule (McCafferty et al, 1990, *Nature* 348: 552-554). Phage displaying antibody fragments specific for a particular antigen may be selected through binding to the antigen in question. Isolated phage may then be amplified and the gene encoding the selected antibody variable domains may optionally be transferred to other antibody formats, such as e.g. full-length immunoglobulin, and expressed in high amounts using appropriate vectors and host cells well known in the art. Alternatively, the "human" antibodies can be made by immunising transgenic mice which contain, in essence, human immunoglobulin genes (Vaughan et al (1998) *Nature Biotechnol*. 16, 535-539).

It is appreciated that when the antibody is for administration to a non-human individual, the antibody may have been specifically designed/produced for the intended recipient species.

The format of displayed antibody specificities on phage particles may differ. The most commonly used formats are Fab (Griffiths et al, 1994. *EMBO J*. 13: 3245-3260) and single chain (scFv) (Hoogenboom et al, 1992, *J Mol Biol*. 227: 381-388) both comprising the variable antigen binding domains of antibodies. The single chain format is composed of a variable heavy domain ($V_H$) linked to a variable light domain ($V_L$) via a flexible linker (U.S. Pat. No. 4,946,778). Before use as a therapeutic agent, the antibody may be transferred to a soluble format e.g. Fab or scFv and analysed as such. In later steps the antibody fragment identified to have desirable characteristics may be transferred into yet other formats such as full-length antibodies.

WO 98/32845 and Soderlind et al (2000) *Nature BioTechnol*. 18: 852-856 describe technology for the generation of variability in antibody libraries. Antibody fragments derived from this library all have the same framework regions and only differ in their CDRs. Since the framework regions are of germline sequence the immunogenicity of antibodies derived from the library, or similar libraries produced using the same technology, are expected to be particularly low (Soderlind et al, 2000). This property is of great value for therapeutic antibodies, reducing the risk that the patient forms antibodies to the administered antibody, thereby reducing risks for allergic reactions, the occurrence of blocking antibodies, and allowing a long plasma half-life of the antibody. Thus, when developing therapeutic antibodies to be used in humans, modern recombinant library technology (Soderlind et al, 2001, *Comb. Chem. & High Throughput Screen*. 4: 409-416) is now used in preference to the earlier hybridoma technology.

In another embodiment, the HER2, HER4, FGFR1, EPHA2 or FGFR3 inhibitor may be a small interfering RNA (siRNA) (described by Hannon et al. *Nature*, 418 (6894): 244-51 (2002); Brummelkamp et al, *Science* 21, 21 (2002); and Sui et al., *Proc. Natl Acad. Sci. USA* 99, 5515-5520 (2002)). RNA interference (RNAi) is the process of sequence-specific post-transcriptional gene silencing in animals initiated by double-stranded (dsRNA) that is homologous in sequence to the silenced gene. The mediators of sequence-specific mRNA degradation are typically 21- and 22-nucleotide small interfering RNAs (siRNAs) which, in vivo, may be generated by ribonuclease III cleavage from longer dsRNAs. 21-nucleotide siRNA duplexes have been shown to specifically suppress expression of both endogenous and heterologous genes (Elbashir et al (2001) *Nature* 411: 494-498). In mammalian cells it is considered that the siRNA has to be comprised of two complementary 21mers as described below since longer double-stranded (ds) RNAs will activate PKR (dsRNA-dependent protein kinase) and inhibit overall protein synthesis.

Duplex siRNA molecules selective for a polynucleotide encoding the HER2, HER4, FGFR1, EPHA2 or FGFR3 polypeptide can readily be designed by reference to its cDNA sequence. For example, they can be designed by reference to the HER2, HER4, FGFR1, EPHA2 or FGFR3 cDNA sequences in the Genbank Accession Nos listed above.

Typically, the first 21-mer sequence that begins with an AA dinucleotide which is at least 120 nucleotides downstream from the initiator methionine codon is selected. The RNA sequence perfectly complementary to this becomes the first RNA oligonucleotide. The second RNA sequence should be perfectly complementary to the first 19 residues of the first, with an additional UU dinucleotide at its 3' end. Once designed, the synthetic RNA molecules can be synthesized using methods well known in the art.

A number of suitable anti-HER2, HER4, FGFR1, EPHA2 and FGFR3 siRNAs are commercially available, for example, from Sigma-Aldrich in the form of MISSION® Lentiviral transduction particles.

siRNAs may be introduced into cells in the patient using any suitable method, such as those described herein. Typically, the RNA is protected from the extracellular environment, for example by being contained within a suitable carrier or vehicle. Liposome-mediated transfer, e.g. the oligofectamine method, may be used.

In another embodiment, the HER2, HER4, FGFR1, EPHA2 or FGFR3 inhibitor may be an antisense polynucleotide.

Antisense nucleic acid molecules selective for a polynucleotide encoding the HER2, HER4, FGFR1, EPHA2 or FGFR3 polypeptide can readily be designed by reference to its cDNA or gene sequence, as is known in the art. Antisense nucleic acids, such as oligonucleotides, are single-stranded nucleic acids, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognize sequences in the major groove of the DNA double helix. A triple helix was formed thereby. This suggests that it is possible to synthesize a sequence-specific molecule which specifically binds double-stranded DNA via recognition of major groove hydrogen binding sites. By binding to the target nucleic acid, the above oligonucleotides can inhibit the function of the target nucleic acid. This could, for example, be a result of blocking the transcription, processing, poly(A) addition, replication, translation, or promoting inhibitory mechanisms of the cells, such as promoting RNA degradations.

Antisense oligonucleotides are prepared in the laboratory and then introduced into cells, for example by microinjection or uptake from the cell culture medium into the cells, or they are expressed in cells after transfection with plasmids or retroviruses or other vectors carrying an antisense gene. Antisense oligonucleotides were first discovered to inhibit viral replication or expression in cell culture for Rous sarcoma virus, vesicular stomatitis virus, herpes simplex virus type 1, simian virus and influenza virus. Since then, inhibition of mRNA translation by antisense oligonucleotides has been studied extensively in cell-free systems including rabbit reticulocyte lysates and wheat germ extracts. Inhibition of viral function by antisense oligonucleotides has been demonstrated ex vivo using oligonucleotides which were complementary to the AIDS HIV retrovirus RNA (Goodchild (1988) "Inhibition of Human Immunodeficiency Virus Replication by Antisense Oligodeoxynucleotides", *Proc. Natl. Acad. Sci.* (USA) 85(15): 5507-11). The Goodchild study showed that oligonucleotides that were most effective were complementary to the poly(A) signal; also effective were those targeted at the 5' end of the RNA, particularly the cap and 5N untranslated region, next to the primer binding site and at the primer binding site. The cap, 5' untranslated region, and poly(A) signal lie within the sequence repeated at the ends of retrovirus RNA (R region) and the oligonucleotides complementary to these may bind twice to the RNA.

Typically, antisense oligonucleotides are 15 to 35 bases in length. For example, 20-mer oligonucleotides have been shown to inhibit the expression of the epidermal growth factor receptor mRNA (Witters et al., *Breast Cancer Res Treat* 53:41-50 (1999)) and 25-mer oligonucleotides have been shown to decrease the expression of adrenocorticotropic hormone by greater than 90% (Frankel et al., *J Neurosurg* 91:261-7 (1999)). However, it is appreciated that it may be desirable to use oligonucleotides with lengths outside this range, for example 10, 11, 12, 13, or 14 bases, or 36, 37, 38, 39 or 40 bases.

Antisense polynucleotides may be administered systemically. Alternatively, and preferably, the inherent binding specificity of polynucleotides characteristic of base pairing is enhanced by limiting the availability of the polynucleotide to its intended locus in vivo, permitting lower dosages to be used and minimizing systemic effects. Thus, polynucleotides may be applied locally to the solid tumor to achieve the desired effect. The concentration of the polynucleotides at the desired locus is much higher than if the polynucleotides were administered systemically, and the therapeutic effect can be achieved using a significantly lower total amount. The local high concentration of polynucleotides enhances penetration of the targeted cells and effectively blocks translation of the target nucleic acid sequences.

It will be appreciated that antisense agents may also include larger molecules which bind to polynucleotides (mRNA or genes) encoding the HER2, HER4, FGFR1 or FGFR3 polypeptide and substantially prevent expression of the protein. Thus, antisense molecules which are substantially complementary to the respective mRNA are also envisaged.

The molecules may be expressed from any suitable genetic construct and delivered to the patient. Typically, the genetic construct which expresses the antisense molecule comprises at least a portion of the HER2, HER4, FGFR1, EPHA2 or FGFR3 cDNA or gene operatively linked to a promoter which can express the antisense molecule in the cell. Preferably, the genetic construct is adapted for delivery to a human cell.

In another embodiment, the HER2, HER4, FGFR1, EPHA2 or FGFR3 inhibitor may be a ribozyme. Ribozymes are RNA or RNA-protein complexes that cleave nucleic acids in a site-specific fashion. Ribozymes have specific catalytic domains that possess endonuclease activity. For example, a large number of ribozymes accelerate phosphoester transfer reactions with a high degree of specificity, often cleaving only one of several phosphoesters in an oligonucleotide substrate. This specificity has been attributed to the requirement that the substrate binds via specific base-pairing interactions to the internal guide sequence ("IGS") of the ribozyme prior to chemical reaction.

Ribozyme catalysis has primarily been observed as part of sequence-specific cleavage/ligation reactions involving nucleic acids. For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications, and ribozymes specific for a polynucleotide encoding the HER2, HER4, FGFR1, EPHA2 or FGFR3 polypeptide may be designed by reference to the HER2, HER4, FGFR1, EPHA2 or FGFR3 cDNA sequence, respectively.

Methods and routes of administering polynucleotide inhibitors, such as siRNA molecules, antisense molecules and ribozymes, to a patient, are described in more detail below.

Typically, the HER2 inhibitor is an anti-HER2 antibody. Preferred anti-HER2 antibodies include trastuzumab and pertuzumab.

Trastuzumab (Herceptin®) is presented as a white to pale yellow lyophilized powder concentrate for solution for infusion. It is currently approved for the treatment of patients with metastatic breast cancer whose tumors overexpress HER2: (a) as monotherapy for the treatment of those patients who have received at least two chemotherapy regimens for their metastatic disease in which the prior chemotherapy has included at least an anthracycline and a taxane unless patients are unsuitable for these treatments, and hormone receptor positive patients have failed hormonal therapy unless patients are unsuitable for these treatments; and (b) in combination with paclitaxel for the treatment of those patients who have not received chemotherapy for their metastatic disease and for whom an anthracycline is not suitable. Trastuzumab is preferably used in patients whose tumors have HER2 overexpression at a 3+ level as determined by immunohistochemistry.

The recommended dosage scheme consists of trastuzumab loading (4 mg/kg body weight) and subsequent weekly doses of 2 mg/kg body weight. It is typically administered until progression of the disease.

Other preferred HER2 inhibitors include lapatinib, neratinib and BIBW 2992.

Lapatinib (Tykerb®) is a small molecule and a member of the 4-anilinoquinazoline class of kinase inhibitors. It is present as the monohydrate of the ditosylate salt, with chemical name N-(3 chloro-4-{[(3-fluorophenyl)methyl]oxy}phenyl)-6-[5-({[2 (methylsulfonyl)ethyl]amino}methyl)-2-furanyl]-4-quinazolinamine bis(4 methylbenzenesulfonate) monohydrate. It has the molecular formula $C_{29}H_{26}ClFN_4O_4S(C_7H_8O_3S)_2 \cdot H_2O$ and a molecular weight of 943.5. Lapatinib is a yellow solid, and its solubility in water is 0.007 mg/ml and in 0.1N HCl is 0.001 mg/mL at 25° C. Each 250 mg tablet of Tykerb® contains 405 mg of lapatinib ditosylate monohydrate, equivalent to 398 mg of lapatinib ditosylate or 250 mg lapatinib free base. The recommended dose of Tykerb® is 1,250 mg (5 tablets) given orally once daily on Days 1-21 continuously, usually in combination with capecitabine 2,000 mg/m²/day (administered orally in 2 doses approximately 12 hours apart) on Days 1-14 in a repeating 21 day cycle. Lapatinib is preferably taken at least one hour before or one hour after a meal. The dose of Lapatinib is preferably taken once daily; dividing the daily dose is not recommended Preferably, the FGFR1 inhibitor is selected from the group consisting of PD173074, SU5402 and Indirubin-3'-monoxime.

Such agents can be used in combination with the compounds described above to sensitize cancers with upregulated FGFR1, or with upregulated FGFR1-signalling, thus providing additional efficacy. —Further suitable agents include AKT inhibitors, DNA damaging agents such as platinum, and also radiotherapy.

The HER4 inhibitor may be lapatinib, which is also a HER2 inhibitor; PF-00299804 (Pfizer) which is a pan-HER inhibitor that inhibits HER1, HER2 and HER4; AEE-788 (Novartis), which is also a HER2 inhibitor; and CI-1033 (Pfizer), which is a pan-HER and an EGFR inhibitor.

The FGFR3 inhibitor may be PKC 412; PD173074, which is also an FGFR1 inhibitor; or an anti-FGFR3 monoclonal antibody such as those described by Qing et al in which R3Mab was the most effective antagonist of FGFR3 activity and was shown to have antitumor activity (Qing et al (2009) "Antibody-based targeting of FGFR3 in bladder carcinoma and t(4; 14)-positive multiple myeloma in mice" *J. Clin. Invest.* 119(5): 1216-1229).

The EPHA2 inhibitor may be a soluble EphA2 receptor, which has been shown to inhibit tumor angiogenesis and progression in vivo (Brantley et al (2002) "Soluble Eph A receptors inhibit tumor angiogenesis and progression in vivo." *Oncogene* 21(46): 7011-26. The EPHA2 inhibitor may also be a catechol derivative described by Stroylov et a (2010) "Novel fragment-like inhibitors of EphA2 obtained by experimental screening and modeling" *Mendeleev Communications* 20(5): 263-265.

We have observed that administration of recombinant human OPCML to cancer cells inhibits phospho S473 AKT, suggesting a potential synergy with platinum based chemotherapy and ionizing radiation.

Thus, in one preferred embodiment, the further anticancer agent may be a platinum-based chemotherapeutic agent. Clinically approved platinum-based chemotherapeutic agents include carboplatin (cis-diammine(cyclobutane-1,1-dicarboxylate-O,O')platinum(II); CAS Registry Number 41575-94-4), cisplatin ((SP-4-2)-diamminedichloridoplatinum; CAS Registry number 15663-271), and oxaliplatin ([(1R,2R)-cyclohexane-1,2-diamine](ethanedioato-O,O')platinum(II); CAS Registry Number 63121-00-6). Oxaliplatin may also be typically administered with fluorouracil and leucovorin in a combination known as FOLFOX. These platinum-based chemotherapeutic agents are typically administered intravenously as a short-term infusion in physiological saline, as is well known in the art.

Additionally or alternatively, the method may further comprise administering an AKT inhibitor to the patient. Many suitable AKT inhibitors are known in the art and include A-443654 by Abbott Laboratories (Han et al (2007) *Oncogene* 26: 5655-5661); GSK690693 by GlaxoSmithKline (Levy et al (2009) *Blood* 113(8): 1723-29); GSK2110183; GSK2141795; triciribine (Merck); KP372-1 (Mandal et al (2006) *Oral Oncol.* 42(4): 430-439); VQD-002 by VioQuest Pharmaceuticals; and perifosine (Gills et al (2009) *Current Oncology Reports* 11: 102-110).

In another embodiment, the patient may be one who is being, or who has been, treated with radiotherapy.

We have shown that the Ig2 domain of OPCML binds to and interacts with FGFR1. Thus, in a specific embodiment of this aspect of the invention, the cancer is one in which FGFR1 is upregulated and/or in which FGFR1 mediated-signaling is upregulated, and the fragment of the OPCML polypeptide comprises or consists of the Ig2 domain of OPCML (SEQ ID NO: 2).

Thus this aspect of the invention includes a method of treating a patient having a cancer in which FGFR1 is upregulated and/or in which FGFR1 mediated-signaling is upregulated, the method comprising administering to the patient a compound comprising or consisting of a polypeptide comprising the Ig2 domain of OPCML (SEQ ID NO: 2), or a variant thereof having at least 90% sequence identity with SEQ ID NO: 2, or a nucleic acid molecule which encodes the polypeptide or variant thereof.

This aspect of the invention also provides the use of a compound comprising or consisting of a polypeptide comprising the Ig2 domain of OPCML (SEQ ID NO: 2), or a variant thereof having at least 90% sequence identity with SEQ ID NO: 2, or a nucleic acid molecule which encodes the polypeptide or variant thereof, in the preparation of a medicament for treating a patient having a cancer in which FGFR1 is upregulated and/or in which FGFR1 mediated-signaling is upregulated.

This aspect of the invention also provides a compound comprising or consisting of a polypeptide comprising the Ig2 domain of OPCML (SEQ ID NO: 2), or a variant thereof having at least 90% sequence identity with SEQ ID NO: 2, or a nucleic acid molecule which encodes the polypeptide or variant thereof, for use in treating a patient having a cancer in which FGFR1 is upregulated and/or in which FGFR1 mediated-signaling is upregulated.

It is, therefore, appreciated that the invention includes a pharmaceutical composition comprising a fragment of OPCML that comprises or consists of the Ig2 domain of OPCML (residues 136-219 of human OPCML); such a fragment of OPCML for use as a medicament; the use of such a fragment of OPCML in the preparation of a medicament for treating cancer; a method of treating cancer by administering such a fragment of OPCML to a patient; and such a fragment of OPCML for use in treating cancer.

We have also shown that the Ig3 domain of OPCML binds to and interacts with HER2. Thus, in another specific embodiment of this aspect of the invention, the cancer is one in which HER2 is upregulated and/or in which HER2 mediated-signaling is upregulated, and the fragment of the OPCML polypeptide comprises or consists of the Ig3 domain of OPCML (SEQ ID NO: 3).

Thus this aspect of the invention includes a method of treating a patient having a cancer in which HER2 is upregulated and/or in which HER2 mediated-signaling is upregulated, the method comprising administering to the patient a compound comprising or consisting of a polypeptide comprising the Ig3 domain of OPCML (SEQ ID NO: 3), or a variant thereof having at least 90% sequence identity with SEQ ID NO: 3, or a nucleic acid molecule which encodes the polypeptide or variant thereof.

This aspect of the invention also provides the use of a compound comprising or consisting of a polypeptide comprising the Ig3 domain of OPCML (SEQ ID NO: 3), or a variant thereof having at least 90% sequence identity with SEQ ID NO: 3, or a nucleic acid molecule which encodes the polypeptide or variant thereof, in the preparation of a medicament for treating a patient having a cancer in which HER2 is upregulated and/or in which HER2 mediated-signaling is upregulated.

This aspect of the invention also provides a compound comprising or consisting of a polypeptide comprising the Ig3 domain of OPCML (SEQ ID NO: 3), or a variant thereof having at least 90% sequence identity with SEQ ID NO: 3, or a nucleic acid molecule which encodes the polypeptide or variant thereof, for use in treating a patient having a cancer in which HER2 is upregulated and/or in which HER2 mediated-signaling is upregulated.

It is, therefore, appreciated that the invention includes a pharmaceutical composition comprising a fragment of OPCML that comprises or consists of the Ig3 domain of OPCML (residues 223-310 of human OPCML); such a fragment of OPCML for use as a medicament; the use of such a fragment of OPCML in the preparation of a medicament for treating cancer; a method of treating cancer by administering such a fragment of OPCML to a patient; and such a fragment of OPCML for use in treating cancer.

The Ig1 domain of OPCML is required for dimerization of OPCML. Thus, optionally, especially if dimerization is required, the fragment of the OPCML polypeptide further comprises the Ig1 domain of OPCML (SEQ ID NO: 4). Thus the compound may comprise a fusion of the Ig1 and Ig2 domains, or a fusion of the Ig1 and Ig3 domains of OPCML.

Alternatively, the fragment of the OPCML polypeptide may be fused to an antibody Fc fragment. This would also allow dimerization if required. Thus the compound may comprise an Ig1-Fc fusion of an Ig2-Fc fusion, or an Ig1-Fc fusion of an Ig3-Fc fusion.

It is appreciated that a compound comprising or consisting of the Ig2 domain, but not the Ig3 domain of OPCML, can be used to target FGFR1 whilst not targeting HER2. Conversely, a compound comprising or consisting of the Ig3 domain, but not the Ig2 domain of OPCML, can be used to target HER2 but not FGFR1.

In a related embodiment, the invention provides a method of treating a patient having HER2-positive (HER2+) cancer, the method comprising administering to the patient a compound comprising or consisting of an OPCML polypeptide (SEQ ID NO: 1), or a fragment thereof which comprises the Ig3 domain of OPCML (SEQ ID NO: 3), or a variant thereof having at least 90% sequence identity with the OPCML polypeptide or the fragment thereof, or a nucleic acid molecule which encodes the OPCML polypeptide or fragment or variant thereof; and a HER2 inhibitor.

This embodiment of the invention also provides a compound comprising or consisting of an OPCML polypeptide (SEQ ID NO: 1), or a fragment thereof which comprises the Ig3 domain of OPCML (SEQ ID NO: 3), or a variant thereof having at least 90% sequence identity with the OPCML polypeptide or the fragment thereof, or a nucleic acid molecule which encodes the OPCML polypeptide or fragment or variant thereof, and a HER2 inhibitor, for use in treating a patient having HER2-positive (HER2+) cancer.

In an embodiment, for the combination for use in treating a patient having HER2+ cancer, the compound and the HER2 inhibitor may be administered separately, whether temporally separated, or administered substantially simultaneously.

In an alternative embodiment, for the combination for use in treating a patient having HER2+ cancer, the compound and the HER2 inhibitor may be administered within the same formulation.

The invention further provides the use of a compound comprising or consisting of an OPCML polypeptide (SEQ ID NO: 1), or a fragment thereof which comprises the Ig3 domain of OPCML (SEQ ID NO: 3), or a variant thereof having at least 90% sequence identity with the OPCML polypeptide or the fragment thereof, or a nucleic acid molecule which encodes the OPCML polypeptide or fragment or variant thereof, and a HER2 inhibitor, in the preparation of a medicament treating a patient having HER2-positive (HER2+) cancer.

In an embodiment, the variant of the fragment of OPCML which comprises the Ig3 domain of OPCML has at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity, with the equivalent region of the human OPCML polypeptide fragment. Such fragments and variants, and nucleic acid molecules encoding them, may be made, for example, using the methods of recombinant DNA technology, protein engineering and site-directed mutagenesis, which are well known in the art.

It is preferred that the fragment of OPCML which comprises the Ig3 domain of OPCML, or the variant thereof possesses at least 50% of the activity of full length human OPCML in inhibiting the proliferation of HER2+ cancer cells in vitro. It is more preferred if the fragment of OPCML, or the variant of the OPCML or fragment thereof possesses at least 50%, or at least 60%, or at least 70%, or at least 80%, or at least 90%, or at least 100% or more of the activity of full length human OPCML in inhibiting the proliferation of HER2+ cancer cells in vitro. This can be determined using methods well known in the art and described in the Examples below.

As discussed above, it is appreciated that the fragment of the OPCML polypeptide or variant thereof further comprises the Ig1 domain of OPCML (SEQ ID NO: 4) or may be fused to an antibody Fc fragment.

Preferences for the formulation and routes of administration of the compound are as described above.

Preferences for the HER2 inhibitor are as defined above, with anti-HER2 antibody such as trastuzumab or pertuzumab, or lapatinib, neratinib and BIBW 2992, being most preferred.

By a HER2+ cancer we mean a cancer that is HercepTest™ positive or FISH positive.

HER2 immunohistochemistry (IHC) may be performed using the Dako HercepTest™ kit, which is a semi-quantitative immunohistochemical assay for determination of HER2 protein (c-erbB-2 oncoprotein) overexpression in breast cancer tissues routinely processed for histological evaluation. HercepTest™ is intended as an aid in the assessment of patients for whom treatment with humanized monoclonal antibody to HER2 protein, Herceptin™ (trastuzumab), is being considered. HercepTest™ specifically demonstrates overexpression of HER2 protein. Positive or negative results aid in the classification of abnormal cells/tissues and provide a basis for treatment selection. The kit includes reagents required for the immunohistochemical staining (except wash buffer), control slides representing different expression levels of HER2 protein, and detailed instructions. A result of 3+ in using the Dako HercepTest™ kit is indicative of a HER+ cancer.

A HER2+ positive cancer is one in which the HER2 gene copy number is found to be greater than two by FISH analysis.

The HER2+ cancer may be ovarian cancer, breast cancer, renal cancer, gastrointestinal cancer, brain cancer, lung cancer, nasopharyngeal cancer, esophageal cancer, gastric cancer, colon cancer, liver cancer, cervical cancer, prostate cancer, non-Hodgkin lymphoma, Hodgkin lymphoma, and nasal NK/T-cell lymphoma.

Most preferably, the cancer is ovarian cancer or breast cancer or gastric cancer.

Typically, the compound comprising or consisting of the OPCML or fragment or variant or nucleic acid will be administered separately from the HER2 inhibitor. Typically, the compound will be administered given as a separate infusion, either substantially simultaneously with, or before or after the inhibitor. It is possible that when both the inhibitor, e.g., trastuzumab, and the compound are to be administered in the same way, e.g. by infusion, they may be administered together. Lapatinib is a tablet so will usually be administered separately from the compound.

A second aspect of the invention provides a method of treating a patient having OPCML-positive (OPCML+) and HER2 positive (HER2+) cancer, the method comprising administering a HER2 inhibitor to the patient.

This aspect of the invention provides the use of a HER2 inhibitor in the preparation of a medicament for treating a patient having OPCML+ and HER2+ cancer. This aspect of the invention also provides a HER2 inhibitor for use in treating a patient having OPCML+ and HER2+ cancer.

Preferences for the HER2 inhibitor are as defined above, with anti-HER2 antibody such as trastuzumab or pertuzumab, or lapatinib, neratinib and BIBW 2992, being most preferred.

In an embodiment, the invention further comprises the prior step of identifying a patient having OPCML+ and HER2+ cancer. In an alternative embodiment, the invention further comprises the prior step of determining whether the patient has OPCML+ and HER2+ cancer The OPCML+ cancer may be identified by IHC. A cancer that shows 2+ or 3+ positive cytoplasmic expression of OPCML by IHC in comparison to non-cancerous adjacent tissue may be considered to be OPCML+. In an embodiment, by quantitative RT-PCR, OPCML+ cancer is one that has at least 2×, or at least 3×, or at least 4×, or at least 5×, or at least 10×, or at least 50×, or at least 10×, or at least 1000× above control levels. Typically, the OPCML+ cancer has above-median, and preferably upper-quartile, expression of OPCML.

In an embodiment, the control levels for OPCML in the cancer of a specific tissue or organ may be the average (mean, or preferably median) level of OPCML found in the same tissue or organ in a population of individuals who do not have cancer in that tissue or organ, and typically do not have cancer at all.

In an alternative embodiment, the control levels for OPCML in the cancer of a specific tissue or organ may be the average (mean, or preferably median) level of OPCML found in a population of patients with the same cancer.

Typically, the population of control individuals is matched for gender, age, and ethnic origin. Preferably, the population of control individuals comprises at least 5, 10, 50, 100, 200, 300, 400 or 500 individuals and more preferably at least 1000, 5000 or 10000 individuals.

Suitable methods for determining whether a cancer is HER2+ are known in the art and are discussed above. For example, a HER2+ positive cancer is one in which the HER2 gene copy number is found to be greater than two by FISH analysis.

The OPCML+ and HER2+ cancer may be ovarian cancer, breast cancer, renal cancer, gastrointestinal cancer, brain cancer, lung cancer, nasopharyngeal cancer, esophageal cancer, gastric cancer, colon cancer, liver cancer, cervical cancer, prostate cancer, non-Hodgkin lymphoma, Hodgkin lymphoma, and nasal NK/T-cell lymphoma.

Most preferably, the cancer is ovarian cancer or breast cancer.

In an embodiment, the method further comprises administering a platinum-based chemotherapeutic agent to the patient. Preferences for the platinum-based chemotherapeutic agents are as described above. Carboplatin, oxaliplatin and cisplatin are most preferred.

We have found that AKT s473 phosphorylation is a key event associated with platinum resistance, and targeting this reverses platinum resistance by altering AKT mediated cell survival. This has been demonstrated in the context of using an AKT inhibitor. We have also found that administration of recombinant human OPCML inhibits AKT s473 phosphorylation which suggests that OPCML reverses platinum resistance in this in vitro system. Thus, a third aspect of the invention provides a method of treating a patient having OPCML-positive (OPCML+) cancer, the method comprising administering a platinum-based chemotherapeutic agent to the patient.

This aspect of the invention provides the use of a platinum-based chemotherapeutic agent in the preparation of a medicament for treating a patient having OPCML+ cancer. This aspect of the invention also provides a platinum-based chemotherapeutic agent for use in treating a patient having OPCML+ cancer.

Preferences for the platinum-based chemotherapeutic agents are as described above. Carboplatin, oxaliplatin and cisplatin are most preferred.

In an embodiment, the invention further comprises the prior step of identifying a patient having OPCML+ cancer. In an alternative embodiment, the invention further comprises the prior step of determining whether the patient has OPCML+ cancer. Suitable methods for determining whether a cancer is OPCML+ are known in the art and are discussed above.

The OPCML+ cancer may be ovarian cancer, breast cancer, renal cancer, gastrointestinal cancer, brain cancer, lung cancer, nasopharyngeal cancer, esophageal cancer, gastric cancer, colon cancer, liver cancer, cervical cancer, prostate cancer, non-Hodgkin lymphoma, Hodgkin lymphoma, and nasal NK/T-cell lymphoma.

Most preferably, the cancer is ovarian cancer or breast cancer.

A fourth aspect of the invention provides a method of treating a patient having OPCML-negative cancer, the method comprising administering a compound comprising or consisting of an OPCML polypeptide (SEQ ID NO: 1), or a fragment thereof which comprises at least one Ig domain of OPCML, or a variant thereof having at least 90% sequence identity with the OPCML polypeptide or the fragment thereof, or a nucleic acid molecule which encodes the OPCML polypeptide or fragment or variant thereof, and a platinum-based chemotherapeutic agent, or ionizing radiation, or both, to the patient.

This aspect of the invention includes the use of the compound comprising or consisting of the OPCML polypeptide or fragment or variant thereof, or the nucleic acid molecule which encodes the OPCML polypeptide or fragment or variant, and a platinum-based chemotherapeutic agent, in the preparation of a medicament for treating a patient having OPCML-negative cancer. The patient may be one who is being administered ionizing radiation (i.e., radiotherapy).

This aspect of the invention also includes a compound comprising or consisting of the OPCML polypeptide or fragment thereof or variant thereof, or the nucleic acid molecule which encodes the OPCML polypeptide or fragment or variant, and a platinum-based chemotherapeutic agent, for use in treating a patient having OPCML-negative cancer. The patient may be one who is undergoing radiotherapy.

The OPCML-negative cancer may be identified by IHC. A cancer that shows 0 or 1+ positive cytoplasmic expression of OPCML by IHC in comparison to non-cancerous adjacent tissue may be considered to be OPCML-negative.

In an embodiment, by quantitative RT-PCR, OPCML-negative cancer is one that has at least below control levels, e.g., below 50%, or below 25%, or below 10%, or below 5%, or below 1%, or below 0.1%, of OPCML control levels for cancer of that specific tissue or organ as discussed above. Typically, the OPCML-negative cancer has below-median, and preferably lowest-quartile, expression of OPCML.

In an embodiment, in an OPCML-negative cancer, OPCML is not expressed or its expression is not at a detectable level.

Preferences for the compound comprising or consisting of the OPCML polypeptide or fragment thereof or variant thereof or the nucleic acid molecule which encodes the OPCML polypeptide or fragment or variant, for the platinum-based chemotherapeutic agents, and for formulations and routes of administration etc, are as described above in the first aspect of the invention.

In an embodiment, the invention further comprises the prior step of identifying a patient having OPCML-negative cancer. In an alternative embodiment, the invention further comprises the prior step of determining whether the patient has OPCML-negative cancer. Suitable methods for determining whether a cancer is OPCML-negative are known in the art and are discussed herein.

The OPCML-negative cancer may be ovarian cancer, breast cancer, renal cancer, gastrointestinal cancer, brain cancer, lung cancer, nasopharyngeal cancer, esophageal cancer, gastric cancer, colon cancer, liver cancer, cervical cancer, prostate cancer, non-Hodgkin lymphoma, Hodgkin lymphoma, and nasal NK/T-cell lymphoma.

Most preferably, the cancer is ovarian cancer or breast cancer.

A fifth aspect of the invention provides a method for selecting a treatment regime for a cancer patient, the method comprising:

identifying a patient having a cancer in which HER2, HER4, FGFR1, EPHA2 and/or FGFR3 is upregulated and/or in which HER2, HER4, FGFR1, EPHA2 and/or FGFR3 mediated-signaling is upregulated; and selecting a treatment regime that includes administering to the patient a compound comprising or consisting of an OPCML polypeptide (SEQ ID NO: 1), or a fragment thereof which comprises at least one Ig domain of OPCML, or a variant thereof having at least 90% sequence identity with the OPCML polypeptide or the fragment thereof, or a nucleic acid molecule which encodes the OPCML polypeptide or fragment or variant thereof.

This aspect of the invention provides a method for selecting a treatment regime for a cancer patient, the method comprising:

determining whether the patient has a cancer in which HER2, HER4, FGFR1, EPHA2 and/or FGFR3 is upregulated and/or in which HER2, HER4, FGFR1, EPHA2 and/or FGFR3 mediated-signaling is upregulated; and selecting a treatment regime that includes administering to the patient a compound comprising or consisting of an OPCML polypeptide (SEQ ID NO: 1), or a fragment thereof which comprises at least one Ig domain of OPCML, or a variant thereof having at least 90% sequence identity with the OPCML polypeptide or the fragment thereof, or a nucleic acid molecule which encodes the OPCML polypeptide or fragment or variant thereof.

This aspect of the invention provides a method for identifying a treatment regime for a cancer patient, the method comprising:

identifying a patient having a cancer in which HER2, HER4, FGFR1, EPHA2 and/or FGFR3 is upregulated and/or in which HER2, HER4, FGFR1, EPHA2 and/or FGFR3 mediated-signaling is upregulated; or determining whether the patient has a cancer in which HER2, HER4, FGFR1, EPHA2 and/or FGFR3 is upregulated and/or in which HER2, HER4, FGFR1, EPHA2 and/or FGFR3 mediated-signaling is upregulated, wherein an upregulated level of HER2, HER4, FGFR1, EPHA2 and/or FGFR3, and/or an upregulated level of HER2, HER4, FGFR1, EPHA2 and/or FGFR3 mediated-signaling, indicates that a treatment regime that includes administering a compound comprising or consisting of an OPCML polypeptide (SEQ ID NO: 1), or a fragment thereof which comprises at least one Ig domain of OPCML, or a variant thereof having at least 90% sequence identity with the OPCML polypeptide or the fragment thereof, or a nucleic acid molecule which encodes the OPCML polypeptide or fragment or variant thereof, will be more effective than a treatment regime that does not include administering the OPCML polypeptide or fragment or variant or nucleic acid molecule.

The upregulation of HER2, HER4, FGFR1, EPHA2 and/or FGFR3 can be determined by assessing HER2, HER4, FGFR1, EPHA2 and/or FGFR3 mRNA levels, polypeptide levels or gene copy number as described above and as is well known in the art.

Typically, the mRNA levels, polypeptide levels or gene copy number are assessed in a biopsy sample of the cancer. Alternatively, the mRNA levels or polypeptide levels may be assessed in ascites malignant cells from the patient.

For example, the level of HER2, HER4, FGFR1, EPHA2 and/or FGFR3 that is indicative of upregulation may be a level of HER2, HER4, FGFR1, EPHA2 and/or FGFR3 in the tissue or organ with the cancer that is equal to or greater than the mean +2 standard deviations (SD) of the level of HER2, HER4, FGFR1, EPHA2 and/or FGFR3 found in the same tissue or organ in a population of control individuals who do not have cancer in that tissue or organ.

Preferably, however, the level of HER2, HER4, FGFR1, EPHA2 and/or FGFR3 that is indicative of upregulation is an above-median level, or upper quartile level, of HER2, HER4, FGFR1, EPHA2 and/or FGFR3 in the tissue or organ with the cancer in comparison to a population of individuals having cancer in the tissue or organ.

Preferences for the compound comprising or consisting of an OPCML polypeptide, or the fragment or variant thereof, or the nucleic acid molecule which encodes the polypeptide or fragment or variant, and for formulations and routes of administration, are as described above in the first aspect of the invention.

Thus, for example, if the cancer is one in which FGFR1 is upregulated and/or in which FGFR1 mediated-signaling is upregulated, the fragment of the OPCML polypeptide comprises or consists of the Ig2 domain of OPCML (SEQ ID NO: 2), as discussed above.

In another embodiment, if the cancer is one in which HER2 is upregulated and/or in which HER2 mediated-signaling is upregulated, the fragment of the OPCML polypeptide comprises or consists of the Ig3 domain of OPCML (SEQ ID NO: 3), as discussed above.

The cancer for which the treatment regime is selected or identified may be ovarian cancer, breast cancer, renal cancer, gastrointestinal cancer, brain cancer, lung cancer, nasopharyngeal cancer, esophageal cancer, gastric cancer, colon cancer, liver cancer, cervical cancer, prostate cancer, non-Hodgkin lymphoma, Hodgkin lymphoma, and nasal NK/T-cell lymphoma. Preferably, the cancer is ovarian cancer or breast cancer.

A sixth aspect of the invention provides a method for selecting a treatment regime for a cancer patient, the method comprising:
  identifying a patient having a cancer which is HER2+; and
  selecting a treatment regime that includes administering to the patient a compound comprising or consisting of an OPCML polypeptide (SEQ ID NO: 1), or a fragment thereof which comprises the Ig3 domain of OPCML (SEQ ID NO: 3), or a variant thereof having at least 90% sequence identity with the OPCML polypeptide or the fragment thereof, or a nucleic acid molecule which encodes the OPCML polypeptide or fragment or variant thereof, and a HER2 inhibitor.

This aspect of the invention provides a method for selecting a treatment regime for a cancer patient, the method comprising:
  determining whether the cancer is HER2+; and
  selecting a treatment regime that includes administering to the patient a compound comprising or consisting of an OPCML polypeptide (SEQ ID NO: 1), or a fragment thereof which comprises the Ig3 domain of OPCML (SEQ ID NO: 3), or a variant thereof having at least 90% sequence identity with the OPCML polypeptide or the fragment thereof, or a nucleic acid molecule which encodes the OPCML polypeptide or fragment or variant thereof, and a HER2 inhibitor.

Thus, this aspect of the invention provides a method for identifying a treatment regime for a cancer patient, the method comprising:
  identifying a patient having a cancer which is HER2+ or determining whether the cancer is HER2+;
  wherein a HER2+ cancer indicates that a treatment regime that includes administering a compound comprising or consisting of an OPCML polypeptide (SEQ ID NO: 1), or a fragment thereof which comprises the Ig3 domain of OPCML (SEQ ID NO: 3), or a variant thereof having at least 90% sequence identity with the OPCML polypeptide or the fragment thereof, or a nucleic acid molecule which encodes the OPCML polypeptide or fragment or variant thereof, and a HER2 inhibitor, will be more effective than a treatment regime that does not include administering the OPCML polypeptide or fragment or variant or nucleic acid molecule.

Determining whether or not a cancer is HER2+ can be carried out using methods well known in the art and described herein.

Preferences for the compound comprising or consisting of an OPCML polypeptide, or the fragment or variant thereof, or the nucleic acid molecule which encodes the polypeptide or fragment or variant, for the HER2 inhibitor, and for formulations and routes of administration, are as described above in the first aspect of the invention.

The HER2+ cancer for which the treatment regime is selected or identified may be ovarian cancer, breast cancer, renal cancer, gastrointestinal cancer, brain cancer, lung cancer, nasopharyngeal cancer, esophageal cancer, gastric cancer, colon cancer, liver cancer, cervical cancer, prostate cancer, non-Hodgkin lymphoma, Hodgkin lymphoma, and nasal NK/T-cell lymphoma. Preferably, the cancer is ovarian cancer or breast cancer.

A seventh aspect of the invention provides a method for selecting a treatment regime for a cancer patient, the method comprising:
  identifying a patient having a cancer which is OPCML+ and HER2+; and
  selecting a treatment regime that includes administering to the patient a HER2 inhibitor.

This aspect of the invention provides a method for selecting a treatment regime for a cancer patient, the method comprising:
  determining whether the cancer is OPCML+ and HER2+; and
  selecting a treatment regime that includes administering to the patient a HER2 inhibitor.

Thus, this aspect of the invention provides a method for identifying a treatment regime for a cancer patient, the method comprising:
  identifying a patient having a cancer which is OPCML+ and HER2+, or determining whether the cancer is OPCML+ and HER2+;

wherein a OPCML+ and HER2+ cancer indicates that a treatment regime that includes administering a HER2 inhibitor will be more effective than for a patient who has a cancer that is HER2+ and OPCML negative.

Determining whether or not a cancer is OPCML+ and HER2+ can be carried out using methods well known in the art and described herein.

Preferences for the HER2 inhibitor, and for formulations and routes of administration, are as described above in the first aspect of the invention.

The OPCML+ and HER2+ cancer for which the treatment regime is selected or identified may be ovarian cancer, breast cancer, renal cancer, gastrointestinal cancer, brain cancer, lung cancer, nasopharyngeal cancer, esophageal cancer, gastric cancer, colon cancer, liver cancer, cervical cancer, prostate cancer, non-Hodgkin lymphoma, Hodgkin lymphoma, and nasal NK/T-cell lymphoma. Preferably, the cancer is ovarian cancer or breast cancer.

In an embodiment, the selected treatment further comprises administering to the patient compound comprising or consisting of an OPCML polypeptide (SEQ ID NO: 1), or a fragment thereof which comprises the Ig3 domain of OPCML (SEQ ID NO: 3), or a variant thereof having at least 90% sequence identity with the OPCML polypeptide or the fragment thereof, or a nucleic acid molecule which encodes the OPCML polypeptide or fragment or variant thereof. Preferences for the compound are as described above in the first aspect of the invention.

An eighth aspect of the invention provides a method for selecting a treatment regime for a cancer patient, the method comprising:
identifying a patient having a cancer which is OPCML+ and FGFR1+; and
selecting a treatment regime that includes administering to the patient an FGFR1 inhibitor.

This aspect of the invention provides a method for selecting a treatment regime for a cancer patient, the method comprising:
determining whether the cancer is OPCML+ and FGFR1+; and
selecting a treatment regime that includes administering to the patient an FGFR1 inhibitor.

Thus, this aspect of the invention provides a method for identifying a treatment regime for a cancer patient, the method comprising:
identifying a patient having a cancer which is OPCML+ and FGFR1+, or determining whether the cancer is OPCML+ and FGFR1+;
wherein a OPCML+ and FGFR1+ cancer indicates that a treatment regime that includes administering an FGFR1 inhibitor will be more effective than for a patient who has a cancer that is FGFR1+ and OPCML negative.

Determining whether or not a cancer is OPCML+ and FGFR1+ can be carried out using methods well known in the art and described herein.

Preferences for the FGFR1 inhibitor, and for formulations and routes of administration, are as described above in the first aspect of the invention.

The OPCML+ and FGFR1+ cancer for which the treatment regime is selected or identified may be ovarian cancer, breast cancer, renal cancer, gastrointestinal cancer, brain cancer, lung cancer, nasopharyngeal cancer, esophageal cancer, gastric cancer, colon cancer, liver cancer, cervical cancer, prostate cancer, non-Hodgkin lymphoma, Hodgkin lymphoma, and nasal NK/T-cell lymphoma. Preferably, the cancer is ovarian cancer or breast cancer.

In an embodiment, the selected treatment further comprises administering to the patient compound comprising or consisting of an OPCML polypeptide (SEQ ID NO: 1), or a fragment thereof which comprises the Ig2 domain of OPCML (SEQ ID NO: 2), or a variant thereof having at least 90% sequence identity with the OPCML polypeptide or the fragment thereof, or a nucleic acid molecule which encodes the OPCML polypeptide or fragment or variant thereof. Preferences for the compound are as described above in the first aspect of the invention.

We have also shown that the OPCML status of a cancer, alone or in combination with other genetic markers, can be used to classify and stratify the cancer, and to predict the progression free survival (PFS) of cancer patients. We have shown that patients with ovarian, breast, lung and brain cancers that have relatively high levels of OPCML (i.e., above-median levels) have an increased PFS compared to those patients with relatively low levels of OPCML (i.e., below median levels).

Accordingly, the invention provides for the use of means for determining the level of OPCML in a method of predicting PFS of the cancer patient. Many suitable means are described herein. The invention also includes methods of predicting PFS of the cancer patient characterized in that OPCML levels in the cancer are determined.

A ninth aspect of the invention provides a method of predicting an increased progression free survival (PFS) in a patient with ovarian cancer, the method comprising:
determining, from a suitable sample obtained from the patient, the level of OPCML and HER2 in the cancer, wherein an above-median level of OPCML and an upper-quartile HER2 level is indicative of an increased PFS.

This aspect of the invention provides for the use of means for determining the level of OPCML and HER2 in a method of predicting PFS of an ovarian cancer patient. Many suitable means are described herein. The invention also includes methods of predicting PFS of an ovarian cancer patient characterized in that OPCML and HER2 levels in the cancer are determined.

A tenth aspect of the invention provides a method of predicting an increased PFS in a patient with lung cancer, the method comprising:
determining, from a suitable sample obtained from the patient, the level of OPCML and the presence of EGFR mutations in the cancer,
wherein an above-median OPCML level and the presence of EGFR mutations is indicative of an increased PFS.

Suitable EGFR mutations include those described, for example, in Kosaka et al (2004) "Mutations of the epidermal growth factor receptor gene in lung cancer: biological and clinical implications" *Cancer Res.* 64(24): 8919-23.

This aspect of the invention provides for the use of means for determining the level of OPCML and means for identifying EGFR mutations in a method of predicting PFS of a lung cancer patient. Many suitable means are described herein and known in the art. The invention also includes methods of predicting PFS of a lung cancer patient characterized in that OPCML levels and EGFR mutations in the cancer are determined.

An eleventh aspect of the invention provides a method of predicting an increased PFS in a patient with breast cancer, the method comprising:
determining, from a suitable sample obtained from the patient, the level of OPCML, HER2 and EGFR in the cancer, wherein an above median-level of OPCML, and HER2 and EGFR levels within the 3 uppermost quartiles (i.e., excluding the lowermost quartile), is indicative of an increased PFS.

This aspect of the invention provides for the use of means for determining the level of OPCML, HER2 and EGFR in a method of predicting PFS of a breast cancer patient. Many suitable means are described herein. The invention also includes methods of predicting PFS of a breast cancer patient characterized in that OPCML, HER2 and EGFR levels in the cancer are determined.

A twelfth aspect of the invention provides a method of predicting an increased PFS in a patient having glioma, the method comprising:
determining, from a suitable sample obtained from the patient, the level of OPCML in the cancer,
wherein an above-median level of OPCML in the cancer is indicative of an increased PFS.

In an embodiment, an upper-quartile level of OPCML is indicative of an increased PFS in a patient having glioma.

This aspect of the invention provides for the use of means for determining the level of OPCML in a method of predicting PFS of a patient with glioma. Many suitable means are described herein. The invention also includes methods of predicting PFS of a patient having glioma characterized in that OPCML levels in the cancer are determined.

A thirteenth aspect of the invention provides a method of predicting an increased PFS in a patient having HER2+ cancer, the method comprising:
determining, from a suitable sample obtained from the patient, the level of OPCML in the cancer,
wherein an upper-quartile level of OPCML in the patient sample is indicative of an increased PFS.

Typically, the HER2+ cancer is selected from ovarian cancer, breast cancer, lung cancer and gastric cancer. Most preferably, the cancer is ovarian cancer.

This aspect of the invention provides for the use of means for determining the level of OPCML in a method of predicting PFS of a patient with HER2+ cancer. Many suitable means are described herein. The invention also includes methods of predicting PFS of a patient having HER2+ cancer characterized in that OPCML levels in the cancer are determined.

Typically, in the ninth to thirteenth aspects of the invention, the suitable sample may be a cancer sample from the patient. In an embodiment of these aspects of the invention, the method may further comprise the prior step of obtaining the suitable sample from the patient.

In those aspects where OPCML, HER2 and/or EGFR levels are determined, it is appreciated that the polypeptide levels may be determined. This may be measured using methods such as IHC, or by newer methods such as reverse phase protein array (RPPA) which is a high-throughput proteomics technology (see, for example, Sheehan et al (2005) "Use of Reverse Phase Protein Microarrays and Reference Standard Development for Molecular Network Analysis of Metastatic Ovarian Carcinoma" *Molecular & Cellular Proteomics* 4: 346-355).

Additionally or alternatively, in those aspects where OPCML, HER2 and/or EGFR levels are determined, it is appreciated mRNA levels may be determined (either directly or via cDNA). This can be carried out by methods such as qRT-PCR, or microarray expression.

Typically, the level of OPCML, HER2 and/or EGFR is determined in comparison to a population of individuals having cancer in the same tissue or organ as the patient.

In another embodiment of the ninth to thirteenth aspects of the invention, the OPCML levels can be measured by determining loss of heterozygosity (LOH), or gene methylation. As is now well known, methylation of OPCML lowers the expression and activity of OPCML. Thus, increased methylation correlates with decreased OPCML mRNA expression and protein activity.

We have demonstrated correlations and interactions between OPCML and HER2, HER4, FGFR1 and FGFR3, and have identified new and useful combinations of agents that have utility in cancer research, analysis and treatment.

Accordingly, a fourteenth aspect of the invention provides a kit of parts comprising reagents for measuring OPCML levels and reagents for measuring HER2 and/or FGFR1 levels.

The kit may comprise oligonucleotides for the amplification of OPCML polynucleotides and oligonucleotides for the amplification of HER2 and/or FGFR1 polynucleotides. In this embodiment, the kit may further comprise reagents for the preparation of RNA from a tissue sample, and/or reagents for transcribing cDNA from mRNA, which are well known in the art.

The kit may comprise nucleic acid molecules that specifically hybridize to the OPCML gene and which are suitable for use as an in situ hybridization probe and nucleic acid molecules that specifically hybridize to the HER2 and/or FGFR1 gene and which are suitable for use as an in situ hybridization probe. In this embodiment, the kit may further comprise reagents for individually labeling the nucleic acid molecules and/or reagents for individually detecting the nucleic acid molecules, which are well known in the art.

The kit may comprise antibodies that specifically bind to OPCML polypeptide and antibodies that specifically bind to HER2 and/or FGFR1 polypeptide. In this embodiment, the kit may further comprise reagents for individually labeling the antibodies and/or reagents for individually detecting the antibodies, which are well known in the art.

In these kit embodiments and aspects of the invention, the kit typically also comprises a sterile container which contains the various components; such containers can be boxes, ampoules, bottles, vials, tubes, bags, pouches, blister-packs, or other suitable container forms known in the art. Such containers can be made of plastic, glass, laminated paper, metal foil, or other materials suitable for holding research reagents and medicaments.

A fifteenth aspect of the invention provides a kit of parts, comprising reagents for detecting upregulation, e.g., the presence or expression, of HER2, HER4, FGFR1, EPHA2 and/or FGFR3; and a compound comprising or consisting of an OPCML polypeptide (SEQ ID NO: 1), or a fragment thereof comprising at least one Ig domain of OPCML, or a variant thereof having at least 90% sequence identity with the OPCML polypeptide or the fragment thereof, or a nucleic acid molecule which encodes the OPCML polypeptide or fragment or variant thereof.

The reagents for detecting upregulation of HER2, HER4, FGFR1, EPHA2 and/or FGFR3 may comprise antibodies that specifically bind to HER2, HER4, FGFR1, EPHA2 and/or FGFR3 polypeptide, or oligonucleotides for the amplification of HER2, HER4, FGFR1, EPHA2 and/or FGFR3 polynucleotides, or nucleic acid molecules that specifically hybridize to the HER2, HER4, FGFR1, EPHA2 and/or FGFR3 gene and which are suitable for use as an in situ hybridization probe. Many suitable reagents are well known in the art and are commercially available.

The kits may further comprise reagents for the preparation of RNA from a tissue sample and/or reagents for transcribing cDNA from mRNA, reagents for individually labeling the nucleic acid molecules for use as hybridization probes and/or reagents for individually detecting the nucleic acid molecules, or reagents for individually labeling the antibodies and/or reagents for individually detecting the antibodies.

In a specific embodiment, the kit comprises reagents for detecting upregulation, e.g., the presence or expression, of HER2, and a compound comprising or consisting of an OPCML polypeptide (SEQ ID NO: 1), or a fragment thereof comprising at least the Ig3 domain of OPCML (SEQ ID No: 3), or a variant thereof having at least 90% sequence identity with the OPCML polypeptide or the fragment thereof, or a nucleic acid molecule which encodes the OPCML polypeptide or fragment or variant thereof.

In another specific embodiment, the kit comprises reagents for detecting upregulation, e.g., the presence or expression, of FGFR1; and a compound comprising or consisting of an OPCML polypeptide (SEQ ID NO: 1), or a fragment thereof comprising at least the Ig2 domain of OPCML (SEQ ID No: 2), or a variant thereof having at least 90% sequence identity with the OPCML polypeptide or the fragment thereof, or a nucleic acid molecule which encodes the OPCML polypeptide or fragment or variant thereof.

Optionally, the fragments of the OPCML polypeptide or variant thereof further comprises the Ig1 domain of OPCML (SEQ ID NO: 4) or may be fused to an antibody Fc fragment.

All further preferences for the compound comprising or consisting of an OPCML polypeptide, or the fragment or variant thereof, or the nucleic acid molecule which encodes the polypeptide or fragment or variant, and for suitable formulations thereof, are as described above in the first aspect of the invention.

A sixteenth aspect of the invention provides a kit of parts, comprising a compound comprising or consisting of an OPCML polypeptide (SEQ ID NO: 1), or a fragment thereof which comprises the Ig3 domain of OPCML (SEQ ID No: 3), or a variant thereof having at least 90% sequence identity with the OPCML polypeptide or the fragment thereof, or a nucleic acid molecule which encodes the OPCML polypeptide or fragment or variant thereof; and a HER2 inhibitor.

Optionally, the fragments of the OPCML polypeptide or the variant thereof further comprises the Ig1 domain of OPCML (SEQ ID NO: 4) or may be fused to an antibody Fc fragment.

Optionally, the kit further comprises reagents for detecting the presence or expression of HER2 as described above. Additionally or alternatively, the kit may further comprise reagents for measuring OPCML levels as described above.

Preferences for the compound comprising or consisting of an OPCML polypeptide, or the fragment or variant thereof, or the nucleic acid molecule which encodes the polypeptide or fragment or variant, and for the HER2 inhibitor, as well as suitable formulations thereof, are as described above in the first aspect of the invention.

A seventeenth aspect of the invention provides a kit of parts, comprising a compound comprising or consisting of an OPCML polypeptide (SEQ ID NO: 1), or a fragment thereof which comprises the Ig2 domain of OPCML (SEQ ID No: 2), or a variant thereof having at least 90% sequence identity with the OPCML polypeptide or the fragment thereof, or a nucleic acid molecule which encodes the OPCML polypeptide or fragment or variant thereof; and an FGFR1 inhibitor.

Optionally, the fragments of the OPCML polypeptide or the variant thereof further comprise the Ig1 domain of OPCML (SEQ ID NO: 4) or may be fused to an antibody Fc fragment.

Optionally, the kit further comprises reagents for detecting the presence or expression of FGFR1 as described above. Additionally or alternatively, the kit may further comprise reagents for measuring OPCML levels as described above.

Preferences for the compound comprising or consisting of an OPCML polypeptide, or the fragment or variant thereof, or the nucleic acid molecule which encodes the polypeptide or fragment or variant, and for the FGFR1 inhibitor, as well as suitable formulations thereof, are as described above in the first aspect of the invention.

An eighteenth aspect of the invention provides a kit of parts, comprising a compound comprising or consisting of an OPCML polypeptide (SEQ ID NO: 1), or a fragment thereof which comprises at least one Ig domain of OPCML, or a variant thereof having at least 90% sequence identity with the OPCML polypeptide or the fragment thereof, or a nucleic acid molecule which encodes the OPCML polypeptide or fragment or variant thereof; and a platinum based chemotherapeutic agent.

Optionally, the fragments of the OPCML polypeptide of the variant thereof further comprises the Ig1 domain of OPCML (SEQ ID NO: 4) or may be fused to an antibody Fc fragment.

Optionally, the kit may further comprise reagents for measuring OPCML levels as described above.

Preferences for the compound comprising or consisting of an OPCML polypeptide, or the fragment or variant thereof, or the nucleic acid molecule which encodes the poypeptide or fragment or variant, and for the platinum based chemotherapeutic agent, as well as suitable formulations thereof, are as described above in the first aspect of the invention.

A nineteenth aspect of the invention provides a pharmaceutical composition comprising a compound comprising or consisting of an OPCML poypeptide (SEQ ID NO: 1), or a fragment thereof which comprises the Ig3 domain of OPCML (SEQ ID No: 3), or a variant thereof having at least 90% sequence identity with the OPCML poypeptide or the fragment thereof, or a nucleic acid molecule which encodes the OPCML poypeptide or fragment or variant thereof, and a HER2 inhibitor.

The invention also includes the combination of a compound comprising or consisting of an OPCML polypeptide (SEQ ID NO: 1), or a fragment thereof which comprises the Ig3 domain of OPCML (SEQ ID No: 3), or a variant thereof having at least 90% sequence identity with the OPCML poypeptide or the fragment thereof, or a nucleic acid molecule which encodes the OPCML polypeptide or fragment or variant thereof, and a HER2 inhibitor, for use in medicine.

Preferences for the compound comprising or consisting of an OPCML polypeptide, or the fragment or variant thereof, or the nucleic acid molecule which encodes the poypeptide or fragment or variant, and for the HER2 inhibitor, as well as suitable formulations thereof, are as described above in the first aspect of the invention.

A twentieth aspect of the invention provides a pharmaceutical composition comprising a compound comprising or consisting of an OPCML poypeptide (SEQ ID NO: 1), or a fragment thereof which comprises the Ig2 domain of OPCML (SEQ ID No: 2), or a variant thereof having at least 90% sequence identity with the OPCML polypeptide or the fragment thereof, or a nucleic acid molecule which encodes the OPCML polypeptide or fragment or variant thereof, and an FGFR1 inhibitor.

The invention also includes the combination of a compound comprising or consisting of an OPCML polypeptide (SEQ ID NO: 1), or a fragment thereof which comprises the Ig2 domain of OPCML (SEQ ID No: 2), or a variant thereof having at least 90% sequence identity with the OPCML polypeptide or the fragment thereof, or a nucleic acid molecule which encodes the OPCML polypeptide or fragment or variant thereof, and an FGFR1 inhibitor, for use in medicine.

Preferences for the compound comprising or consisting of an OPCML polypeptide, or the fragment or variant thereof, or the nucleic acid molecule which encodes the polypeptide or fragment or variant, and for the FGFR1 inhibitor, as well as suitable formulations thereof, are as described above in the first aspect of the invention.

A twenty-first aspect of the invention provides a pharmaceutical composition comprising a compound comprising or consisting of an OPCML polypeptide (SEQ ID NO: 1), or a fragment thereof which comprises at least one Ig domain of OPCML, or a variant thereof having at least 90% sequence identity with the OPCML polypeptide or the fragment thereof, or a nucleic acid molecule which encodes the OPCML polypeptide or fragment or variant thereof, and a platinum based chemotherapeutic agent.

The invention also includes the combination of a compound comprising or consisting of an OPCML polypeptide (SEQ ID NO: 1), or a fragment thereof which comprises at least one Ig domain of OPCML, or a variant thereof having at least 90% sequence identity with the OPCML polypeptide or the fragment thereof, or a nucleic acid molecule which encodes the OPCML polypeptide or fragment or variant thereof, and a platinum based chemotherapeutic agent, for use in medicine.

Preferences for the compound comprising or consisting of an OPCML polypeptide, or the fragment or variant thereof, or the nucleic acid molecule which encodes the polypeptide or fragment or variant, and for the platinum based chemotherapeutic agent, as well as suitable formulations thereof, are as described above in the first aspect of the invention.

A twenty-second aspect of the invention provides a method of testing a treatment regime for efficacy in treating cancer, the method comprising:
  providing a first group of individuals with cancer;
  administering a test treatment regime to the first group of individuals, wherein the test treatment regime comprises administering a compound comprising or consisting of OPCML polypeptide (SEQ ID NO: 1), or a fragment thereof comprising at least one Ig domain of OPCML, or a variant thereof having at least 70% sequence identity with the OPCML polypeptide or the fragment thereof, or a nucleic acid molecule which encodes the OPCML polypeptide or fragment or variant thereof;
  comparing the first group of individuals to a control group of individuals; and
  assessing whether the treatment regime has contributed to treating the cancer in the a first group of individuals.

A related aspect of the invention provides a method of comparing treatment regimes for the treatment of cancer, the method comprising:
  providing first and second groups of individuals with cancer;
  administering a test treatment regime to the first group of individuals, wherein the test treatment regime comprises administering a compound comprising or consisting of OPCML polypeptide (SEQ ID NO: 1), or a fragment thereof comprising at least one Ig domain of OPCML, or a variant thereof having at least 70% sequence identity with the OPCML polypeptide or the fragment thereof, or a nucleic acid molecule which encodes the OPCML polypeptide or fragment or variant thereof;
  administering a second treatment regime to the second group of individuals;
  comparing the first and second groups of individuals; and
  assessing whether the test treatment regime has improved the treatment of the cancer in the first group of individuals compared to the treatment of the cancer second group of individuals.

As is well known in the art, to control for the 'placebo effect', it may be desirable to substitute the test treatment regime for a placebo in a proportion of the first and/or second group of individuals undergoing the assessment.

Preferences for the compound comprising or consisting of an OPCML polypeptide, or the fragment or variant thereof, or the nucleic acid molecule which encodes the polypeptide or fragment or variant, as well as suitable formulations thereof, are as described above in the first aspect of the invention.

In the embodiment where the method is conducted in the context of a clinical trial, the individuals with cancer may be human patients with cancer: The human patient may have a cancer selected from ovarian cancer, breast cancer, renal cancer, gastrointestinal cancer, brain cancer, lung cancer, nasopharyngeal cancer, esophageal cancer, gastric cancer, colon cancer, liver cancer, cervical cancer, prostate cancer, non-Hodgkin lymphoma, Hodgkin lymphoma, and nasal NKT-cell lymphoma. It is preferred that the cancer is ovarian cancer or breast cancer.

In another embodiment, the individuals with cancer may be non-human animal models of cancer. The animal model of cancer may be a model of ovarian, lung, breast, colorectal, pancreatic, gastric, esophageal, renal, biliary, hepatic, cervical, uterine or prostate cancer. The animal model of cancer may be a xenograph model of cancer. Typically, the animal model of cancer is a mouse model of cancer, which may be nude mouse, scid mouse or oncomouse model of cancer.

In an embodiment, the test treatment regime is administered by intravenous or intraperitoneal administration.

Assessment of the test treatment regime may be carried out multiple times, for example at regular intervals such as weekly, monthly, every six months or every year in order to monitor efficacy of the test treatment over time.

Assessment of the test treatment regime may suitably comprise PK and/or PD analysis of the first group of individuals or in vivo molecular imaging of the first group of individuals using FLT, FDG, aposense or PET tracers.

In an embodiment, assessment of the individuals may include assessing, in a suitable sample obtained from the individuals, the level of DNA methylation of the OPCML gene and/or OPCML loss of heterozygosity.

In an additional or alternative embodiment, assessment of the individuals may include assessing, in a suitable sample obtained from the individuals, mRNA or protein expression levels and/or gene copy number of FGFR1, FGFR3, HER2, HER4 and/or EGFR.

Typically, the compound comprising or consisting of the OPCML polypeptide or the fragment or variant thereof is detectably labeled for in vivo imaging.

In an embodiment, the test treatment regime further comprises administration of an FGFR1 inhibitor, an FGFR3 inhibitor, an HER2 inhibitor, an HER4 inhibitor, an EPHA2 inhibitor and/or an EGFR inhibitor to the first group of individuals. Suitable inhibitors are well known in the art and described herein. Preferably, the HER2 inhibitor is an anti-HER2 antibody such as trastuzumab or pertuzumab, or is selected from the group consisting of lapatinib, neratinib and BIBW 2992. Also preferably, the FGFR1 inhibitor is selected from the group consisting of PD 173074, SU5402 and Indirubin-3'-monoxime.

Additionally or alternatively, the test treatment regime may further comprise administration of a platinum based chemotherapeutic agent to the first group of individuals.

Preferences for the FGFR1, FGFR3, HER2, HER4, EPHA2 and/or EGFR inhibitors, and for the platinum based chemotherapeutic agents, as well as suitable formulations thereof, are as described above in the first aspect of the invention.

Additionally or alternatively, the test treatment regime may yet further comprise radiotherapy of the first group of individuals.

A twenty-third aspect of the invention provides a method of identifying an agent that may be useful in the treatment of cancer, or a lead compound for the identification of an agent that may be useful in the treatment of cancer, the method comprising:

providing a test agent comprising or consisting of OPCML polypeptide (SEQ ID NO: 1), or a fragment thereof comprising at least one Ig domain of OPCML, or a variant thereof having at least 70% sequence identity with the OPCML polypeptide or the fragment thereof, or a nucleic acid molecule which encodes the OPCML polypeptide or fragment or variant thereof; and testing the candidate agent in an in vitro anti-cancer assay, wherein a candidate agent that shows efficacy in the anti-cancer assay may be a compound that is useful in the treatment of cancer, or may be a lead compound for the identification of an agent that is useful in the treatment of cancer.

Preferences for the compound comprising or consisting of an OPCML polypeptide, or the fragment or variant thereof, or the nucleic acid molecule which encodes the polypeptide or fragment or variant, as well as suitable formulations thereof, are as described above in the first aspect of the invention. Thus, for example, the OPCML polypeptide may be recombinant human OPCML (SEQ ID No: 1); the OPCML polypeptide fragment may comprise or consist of the Ig2 domain of human OPCML (SEQ ID No: 2); the OPCML polypeptide fragment comprises may comprise or consist of the Ig3 domain of human OPCML (SEQ ID No: 3); and the fragment of the OPCML polypeptide may further comprises the Ig1 domain of human OPCML (SEQ ID NO: 4) or may be fused to an antibody Fc fragment.

The variant of the OPCML polypeptide or of the fragment thereof typically has at least 80% sequence identity, or at least 85%, or at least 90%, or at least 91%, or at least 92%, or at least 93%, or at least 94%, or at least 95% or at least 96%, or at least 97%, or at least 98%, or at least 99% sequence identity, with the human OPCML polypeptide (SEQ ID No: 1) or the fragment thereof.

The in vitro anti-cancer assay may be a cellular proliferation assay of primary cancer cells or cancer cell lines in vitro, such as described in the examples and well known in the art. Other suitable assays include assays for RTK downregulation, and downregulation of phosphoERK/Phospho-AKT as are known in the art.

In an embodiment, the identified compound is modified, and the modified compound is tested for efficacy in an in vitro anti-cancer assay. Further, the identified compound or the modified compound is tested for efficacy in an animal model, typically a mouse model, of cancer.

The method may further comprise the step of synthesising, purifying and/or formulating the identified compound or the modified compound.

The invention will now be described in more detail with respect to the following Figures and Examples.

FIG. 1: Expression of OPCML is induced by EGF and FGF1/2. (A) OPCML induction by EGF and FGF1/2 in SK-OV-3: (i) induction of OPCML expression upon EGF stimulation (50 ng/ml) determined by qRT-PCR; (ii) induction of OPCML protein under same conditions. (B) (i) Induction of OPCML expression by FGF1 and FGF2 stimulation (black and grey lines respectively) at 10 ng/ml; (ii) induction of the OPCML protein under the same FGF2 conditions.

FIG. 2: OPCML interacts with the ECD of HER2 and FGFR1 but not EGFR. (A) (i): Co-IP was performed using protein extracts from SKOBS-V1.2, SKOBS-3.5 and BKS2.1 (SKOBS-3.5 and BKS2.1 express 3 and 20-fold more OPCML protein than normal physiological levels seen in OSE-C2). The goat polyclonal anti-OPCML (R & D Systems) was used in initial IP and products were detected on Western blots employing respective Abs for EGFR and HER2. The reciprocal IP with a monoclonal to ECD of HER2 (Calbiochem) is shown with successful immunoblotting for OPCML in the BKS2.1 stable line (expressing 20-fold more OPCML); (ii) Co-IP using the OPCML Ab in SKOBS-V1.2 and BKS2.1 lines were immunoblotted with anti-FGFR1αECD Ab. (B) A structural representation of GST-OPCML 1+2 and GST-OPCML 1+2+3 constructs with subsequent Western blot analysis of the fusion proteins. (C)(i) GST pull-down assay with SK-OV-3 cell lysate showing binding of HER2 to GST-OPCML 1+2+3 only (lane 2), and no binding of EGFR to any GST-OPCML protein (top panel). FGFR1 was also shown to bind GST-OPCML 1+2+3 and GST-OPCML 1+2 from the same pull-down with lysate from SK-OV-3 cells transiently transfected with FGFR1 cDNA. The presence of the OPCML fusion proteins in these assays was verified by immunoblotting (bottom panel); (ii) In vitro interactions were undertaken verifying binding of HER2 and FGFR1 extracellular domain protein generated from in vitro transcription and translation kit (TnT) to GST-OPCML fusion proteins. HER2 ECD is seen to bind to GST-OPCML 1+2+3 only suggesting that domain 3 is critical whereas FGFR1 binds to GST OPCML 1+2 suggesting binding outwith domain 3.

FIG. 3: Expression of OPCML in ovarian cancer cells downregulates HER2 and FGFR1 but not EGFR or FGFR2, abrogates HER2, EGFR and FGFR1 tyrosine phosphorylation, and reduces growth. (A) (i) Stable OPCML results in the abrogation of HER2 protein expression, but not EGFR protein expression; (ii) Similarly, OPCML stable expression leads to downregulated FGFR1 but not FGFR2. (B) (i) Immunofluorescence microscopy showing HER2 expression in control SKOBS-V1.2 and OPCML expressing BKS2.1 cells. Abundant HER2 expression seen in SKOBS-V1.2 is reduced in BKS2.1 line associated with expression of OPCML. Note co-localisation of OPCML and HER2; (ii) chart illustrating the mean pixel intensity of receptor tyrosine kinases HER2, EGFR, FGFR1 FGFR2 in the context of minimal (SKOBS 2.1) or high (BKS2.1) OPCML expression showing significant downregulation of HER2 and FGFR1. (C) (i) Phosphorylation of specific key tyrosines was analysed by western blotting in BKS2.1 compared to the SKOBS-V1.2 line using phospho-antibodies. Phospho-EGFR Y1173, phospho-HER2 Y1248 and phospho-FGFR1 Y766 were all profoundly abrogated with expression of OPCML; (ii) Similar analysis of downstream signaling adaptor and substrates also exhibited strong downregulation of phospho signal at PLCγ, Grb2 and ERKp42/p44 in response to OPCML expression/EGF Stimulation; (iii) Western analysis of phosphorylated Akt (Ser 473 and Thr 308) as well as total Akt protein in SKOBS-V1.2 and BKS2.1 expressing high levels of OPCML; (iv) proliferation curves of OPCML stable clones (BKS2.1 and SKOBS-3.5), and OSE-C2 cells compared to the SK-OV-3 empty vector control line (SKOBS-V1.2) on 0.25% FCS-supplemented medium with 50 ng/ml EGF as measured by MTT assay. (D) (i) Expression of OPCML downregulates HER2, FGFR1 and FGFR3 expression; (ii) Complete protein knockdown of physiological OPCML in OSE-C2 cells with no loss in the non-silencing control (NS) results in an increase in total HER2 and FGFR1 compared with controls. (E) Examples of Immunofluorescent microscopy images used in the relative abundance measurement in (B), showing the relative signal intensity of EGFR and FGFR2 remaining constant, but FGFR1 levels drastically reduced in BKS2.1.

FIG. 4: OPCML presents HER2/EGFR heterodimer formations. (A) SKOBS-V1.2 and BKS2.1 cell extracts were subjected to Co-IP and immunoblotted with the indicated antibodies, demonstrating loss of heterodimerisation. (B) Monolayers of SKOBS-V1.2, SKOBS3.5 and BKS2.1 were incubated with 0.02 pg/ml [$^{125}$I] EGF for 2 h at 4° C. Levels of radiolabel led EGF binding were determined by detection of gamma emission.

FIG. 5: OPCML localizes in lipid rafts, and enhances HER2 ubiquitination and proteasomal degradation. (A) (i) OPCML localizes to detergent insoluble fraction indicating location in lipid rafts (R—raft; NR—non-raft); (ii) Majority of internalized OPCML colocalizes with caveolin-1 (a marker of the raft-caveolar pathway) compared to EEA-1 (early endosome marker); (iii) Immunofluorescence microscopy of SK-OV-3 and BKS2.1 cells growing on glass slides after being fixed and permeabilised. OPCML and HER2 were detected in (a) SK-OV-3 ovarian cancer line and (b) BKS2.1 using anti-mouse mAb OPCML and rabbit mAb HER2 antibodies and fluorescently labeled secondary antibody to murine (Alexa—594) and rabbit (Alexa—488) immunoglobulins. OPCML and EGFR were detected in (c) SK-OV-3 and (d) BKS2.1 cells using mouse mAb OPCML and goat pAb EGFR antibodies and fluorescently labeled secondary antibody to murine (Alexa-594) and goat (Alexa-488) immunoglobulins. (B) (i) BKS2.1 and SKOBS-V1.2 transfected with HA-tagged-ubiquitin plasmid were serum starved then stimulated with 50 ng/ml EGF before being immunoprecipitated with HER2 and immunoblotted with HA Ab, higher molecular weight shift is seen with HA signifying polyubiquitination of HER2; (ii) Densitometric analysis of HA-ubiquitin WB of HER-IP samples from −/+OPCML expressing cell lines. (C)(i)&(ii) OPCML expression induces a shift in proportion of HER-2. (D) (i)&(ii) SKOBS-V1.2 and BKS2.1 cells were treated with EGF (50 ng/ml) for 60 minutes in the presence or absence of the proteasomal inhibitor MG-132 (1 μm). Cell lysates were subjected to immunoblotting with the indicated antibodies. Ablation of HER2 protein level in the BKS2.1 line is restored in the presence of MG-132 whereas in SKOBS-V1.2 both +/−MG-132 lanes have equal intensity HER2 immunoreactivity. The lysates were also challenged with FGFR1-specific Abs showing similar OPCML-specific upregulation of the 79 kD FGFR1 band in the absence of MG-132; (iii) Disruption of cholesterol using methyl-β-cyclodextrin inhibits degradation of HER2.

FIG. 6: The sensitivity to the dual HER2-EGFR specific TKI lapatinib and HER2-specific trastuzumab. (A) SKOBS-V1.2 and BKS2.1 cells were stimulated with 50 ng/ml EGF for 30 minutes in absence/presence of 1, 2 and 10 nM lapatinib (i) or 5 and 10 μg/ml trastuzumab (ii) and blotted for phospho-ERK and phospho-Akt. The extent of pERK inhibition by lapatinib was confirmed by densitometry (data not shown). (B) The effect of OPCML knockdown on the efficiency of lapatinib-induced pERK attenuation was analysed; densitometry of pERK signal (mean values of 3 independent experiments). Lapatinib reduced the EGF-induced pERK signal by 70% in the presence of non-silencing (non-si) duplex. Knockdown by siRNA to OPCML abrogated the lapatinib mediated inhibition of pERK signal significantly, reducing the extent of inhibition to 47% (P=0.0009). (C) The sensitization of ovarian cancer cell lines (SKOBS-3.5 and BKS2.1) to lapatinib compared to SKOBS-V1.2 illustrates BKS2.1 achieving a >10-fold increase in sensitivity. The extent of pERK inhibition by lapatinib is illustrated in the densitometry bar chart depicting the % intensity of phospho-ERK p42/42 signal after lapatinib treatment compared to the EGF stimulation with no lapatinib administered taken as 100% (not shown). From the densitometry of phospho-ERK signal strength, 1 nM lapatinib reduces the phospho-ERK signal intensity more than 10 nM lapatinib in SKOBS-V1.2.

FIG. 7: Kaplan-Meier curves of ovarian cancer progression-free survival against time. (i) Survival compared between low (N=122) and high (N=129) OPCML expression (N=251 patients, RNA expression data from large Bowtell dataset). (ii) Survival between top quartile (High Her2/High OPCML [N=42] and High Her2/Low OPCML [N=17]) HER2 RNA expression and bottom quartile (Low Her2/High OPCML [N=21] and Low Her2/Low OPCML [N=41]) HER2 dichotomised around OPCML median.

FIG. 8: Purification of recombinant human OPCML expressed in *E. coli*. (A) Schematic diagram of OPCML and the 3 Ig-domains subcloned for recombinant expression. (B) SDS-PAGE analysis of recombinant human OPCML expressed in *E. coli*. Protein expression was induced by the addition of IPTG (1 mM final concentration). Lane M shows protein molecular mass markers; lane 1 shows uninduced whole cell lysate (WC); lanes 2 and 3 show soluble (sol) and insoluble (ins) fraction of induced cell lysate, respectively. Gels were stained with Coomassie Brilliant Blue. (C) SDS-PAGE analysis of inclusion body purification and refolding. Lane 1 shows purified inclusion bodies (IB) and lane 2 shows inclusion bodies denatured in 8 M Urea and refolded by dialysis into PBS. Insoluble proteins were removed by centrifugation and a sample of the supernatant retained for analysis (RF). Gels were stained with Coomassie Brilliant Blue. (D) Image of OPCML crystals obtained by hanging drop at a protein concentration of 10 mg/ml.

FIG. 9: Cellular uptake of recombinant OPCML. SKOV-3 cells were incubated with vehicle alone or vehicle including 2 μM OPCML for 24 h. Cells were then washed 3× with PBS and fixed with 4% PFA. Cells were then prepared for IFM using rabbit α-HER2 mAb and mouse α-OPCML mAb. Goat α-rabbit alexa-488 and α-mouse alexa-555 secondary antibodies were used. Slides were imaged using a Leica SP5 confocal microscope.

FIG. 10: Exogenous OPCML administration inhibits RTK signaling in vitro. (A) Western Blot analysis of pHER, tHER2, tEGFR, pEGFR, tFGFR, pFGFR proteins from SKOV-3 cells untreated, treated with vehicle only or OPCML (2 μM) for 48 h. (B) Western blot analysis of pAKT, tAKT, pERK, tERK proteins from SKOV-3 cells untreated, treated with vehicle only or OPCML (2 μM) for 48 h. Protein loading was standardised by BCA-assay and β-tubulin was used as a loading control.

FIG. 11: Exogenous OPCML administration inhibits growth of ovarian and breast cancer cell lines. (A) SKOV-3 cells were subjected to a 48 h in vitro growth assay with varying concentrations of OPCML administration. (B) A 96 h in vitro SKOV-3 growth assay with 2 μM rOPCML administered to growth media. Time points were collected every 24 h and normalised to control cells treated with vehicle only. Cell viability was quantified using MTT and measured at 570 nm. (C) Upper panel-OSE-C2 and SKOV-3 cells were subjected to a 48 h in vitro growth assay with varying OPCML concentrations (0.5, 1, 2, 5 and 10 μM); lower panel—normal ovarian surface epithelial cells (OSE-C2) and a panel of ovarian (SKOV-3, IGROV, OVISE, OVCAR-5, A2780, PEA1 and PEA2) and HER2-positive (MDA-231) and negative (BT-474) breast cancer cells were subjected to an in vitro growth assay with 10 μm OPCML. Time points were collected at 24 h and 48 h and cell growth was monitored to vehicle only controls. Cell viability was quantified in all experiments using an MTT-based assay and measured at 570 nm.

FIG. 12: Kaplan-Meier analysis of overall survival according to OPCML dichotomised survival. Analyses were conducted for (A) breast cancer, (B) lung cancer, and (C&D) high grade gliomas. The Breast Cancer microarray dataset, for the first of the three graphs, was taken from Wang et al (2005) "Gene-expression profiles to predict distant metastasis of lymph-node-negative primary breast cancer" *Lancet* 365(9460): 671-9. The Glioblastoma microarray dataset was taken from Roel et al (2010) "Integrated Genomic Analysis Identifies Clinically Relevant Subtypes of Glioblastoma Characterized by Abnormalities in PDGFRA, IDH1, EGFR, and NF1" *Cancer Cell* 17(1): 98-110. The Lung cancer microarray dataset was taken from Toshiyuki Takeuchi et al (2006) "Expression Profile-Defined Classification of Lung Adenocarcinoma Shows Close Relationship With Underlying Major Genetic Changes and Clinicopathologic Behaviors" *Journal of Clinical Oncology* 24(11): 1679-1688.

FIG. 13: OPCML has functional characteristics of a tumour suppressor gene in vitro and in vivo. (A) Functional in vitro growth assays comparing parent, OPCML wild-type sense-transfected (two independent cell lines) and OPCML antisense-transfected, clonal SKOV-3 cell lines. Cells were counted every third day for 12 d. The values shown are the mean±s.d. of triplicate assays. (B) Comparison of parent OPCML sense-transfected (two independent cell lines) and OPCML antisense-transfected SKOV-3 cell lines in subcutaneous tumor growth assay. Tumor measurements were recorded every 7 d for 28 d.

FIG. 14: OPCML amino acid sequence from GenBank Accession No. NP_002536 (SEQ ID NO: 1).

FIG. 15: Amino acid sequence of OPCML Ig1 (SEQ ID NO: 4) (Q14982|39-126), Ig2 (SEQ ID NO: 2) (Q14982|36-219) and Ig3 (SEQ ID NO: 3) (Q14982|223-310) domains.

FIG. 16: Expression of OPCML in ovarian cancer cells downregulates a specific repertoire of receptor tyrosine kinases. Western blots demonstrating that (A) OPCML-stable transfection in SKOV-3 and (B) transient transfection in PEO1 negatively regulates EphA2, FGFR1, FGFR3, HER2, and HER4, but not EphA10, FGFR2, EGFR, HER3, VEGFR1 and VEGFR3. (C) siRNA knockdown of OPCML showed a recpirocal increase in expression of OPCML-regulated RTKs previously described in (A). Protein concentration of all cell lysates was quantified by BCA assay and confirmed by western blot analysis of β-tubulin.

FIG. 17: OPCML directly interacts with EphA2, FGFR1 and HER2, but not EGFR. (A) Immuno-precipitation (IP) for OPCML showing positive immunoblots for EphA2, FGFR1 and HER2. Similarly, IP for each of these proteins in turn showed positive immunoblots for OPCML. We were not able to demonstrate co-IP with EGFR and OPCML after numerous attempts. (B) A schematic representation of GST-OPCML domain 1-3 construct. (C). GST-OPCML 1-3 pull-down assay using SKOV-3 cell lysate showing specific binding of HER2 and FGFR1 and no binding of EGFR. The presence of OPCML fusion proteins in these assays was verified by immunoblotting (IB, bottom panel). (D) Confirmatory in vitro interaction studies were undertaken verifying binding of HER2 and FGFR1 extracellular domain protein, generated from in vitro translation kit (TnT) (HER2 ECD) and in *E. coli* (FGFR-ECD) to GST-OPCML 1-3 fusion protein.

FIG. 18: OPCML associated RTK downregulation abrogates downstream signalling. (A) Western blot of total and phospho HER2 and EGFR protein from SKOBS-V1.2 (vector only control) and BKS-2.1 (stable expression of OPCML). Cells were subjected to a 60 min EGF timecourse (50 ng/ml). (B) Western blot of total and phosphor FGFR1 protein from SKOBS-V1.2 (vector only control) and BKS-2.1 (stable expression of OPCML). Cells were subjected to a 60 min FGF1 timecourse (10 ng/ml). (C) Western blot of downstream signaling adaptor and substrates, phosphorylation levels of PLCγ (Y783), ERK 1 & 2 (T202/T204) and Akt at Ser473 in response to OPCML expression. Cells were subjected to a 60 min EGF timecourse (50 ng/ml).

FIG. 19: Mechanism of OPCML mediated RTK down-regulation. (A) OPCML sequesters RTKs in detergent-resistant membrane fraction; SKOBS-V1.2 and BKS2.1 cells were subjected to membrane fractionation to separate detergent resistant membrane fraction (DRMF) or lipid raft fraction from the bulk membrane phase. An equal volume from each fraction was analysed by SDS-PAGE followed by Western blotting with anti-EGFR, anti-HER2, anti-OPCML and anti-Cav-1 antibodies. OPCML was found to be strictly located in the DRMF with Cav-1. Transfection of OPCML was associated with a shift of HER2 and EGFR to the DRMF. (B) Confocal co-immunofluorescence demonstrates co-localisation of rabbit anti-Cav-1/alexa488-conjugated anti-rabbit secondary with mouse anti-OPCML/alexa 555 anti mouse secondary, but not EEA1 suggesting that OPCML is associated with caveolar endocytosis. (C) Quantification of the total number of OPCML pixels colocalised with Cav-1 and EEA-1, demonstrating that OPCML principally co-localises with Cav-1. (D) Ubiquitination status of HER2: SKOBS-V1.2 and BKS-2.1 transiently transfected with an HA-tagged ubiquitin were treated with the MG-132 then EGF or left untreated. Ubiquitylated proteins were detected by immunoblotting (IB) with an anti-HA antibody and samples were run in parallel to probe for HER2 with a mouse anti-HER. These studies demonstrated that OPCML transfection is associated with polyubiquitylation of HER2. (E) Bar chart to show the densitometric quantification of the immunoblotting seen in (D) showing that OPCML expressing BKS2.1 demonstrated increased HA-ubiquitin associated with HER2, not seen in OPCML (–) cells. (F) Confocal co-immunofluorescence of HER2 colocalisation with Cav-1 and EEA-1 with quantification (G) as a percentage of the total number of HER2 pixels detected within the cells. These studies demonstrate that OPCML expressing cells are associated with a switch of HER2 vesicle trafficking from EEA-1 to Cav-1 mediated endocytosis. (H) SKOBS-V1.2 and BKS-2.1 were treated with the lysosomal inhibitor chloroquine (CQ; 0.1 mM) or the proteasomal inhibitor MG-132 (0.1 µM) for 2 h. Immunoblotting for EGFR, HER2, OPCML and β-tubulin was shown. (I) Densitometric analysis of these Western blot data for HER2 (upper chart) and EGFR (lower chart) using β-tubulin as a control. These studies demonstrate that MG132 but not CQ specifically increases HER2 protein level demonstrating that HER2 is degraded preferentially via a proteosomal mechanism via direct binding to OPCML followed by caveolar endocytosis. In contrast, EGFR (that does not bind to OPCML) is not regulated by this mechanism. (J) Cells were incubated in control media or media supplemented with methyl-β-cyclodextrin (M-βCD; 0.2 mM) for 2 h to deplete cholesterol. Western blotting for HER2 and phosphoHER2 (Y1248) demonstrates that cholesterol disruption of lipid rafts also blocks this OPCML mediated HER2 degradation.

FIG. 20: Exogenous rOPCML administration specifically inhibits ovarian, breast and cancer cell growth in vitro. (A) OSE-C2 and SKOV-3 cells were subjected to a 48 h in vitro growth assay with varying concentrations of rOPCML (0.5, 1, 2, 5 and 10 µM). (B) a 96 h in vitro SKOV-3 growth assay with 2 µM rOPCML administered to growth media. Time points were collected every 24 h and normalised to control cells treated with vehicle only. (C) Normal ovarian surface epithelial cells (OSE-C2) and a panel of ovarian (SKOV-3, IGROV, OVISE, OVCAR-5, A2780, PEA1 and PEA2), HER2-positive (MDA-231) and negative (BT-474) breast cancer cells and non-adherant (H69, H501 small-cell) and adherent (A549 carcinoma, HCC95 non-SSLC squamous) lung cancer cells were subjected to an in vitro growth assay with 10 µM of rOPCML. Time points were collected at 24 and 48 h and cell growth was normalised to vehicle only controls. Cell viability was quantified in all experiments using an MTT-based assay and measured at 570 nm. Caspase cleavage-based apoptosis assays using (D) A2780 and (E) SKOV-3 were undertaken with administration of rOPCML (2, 5 and 10 µM) over 24 h. Caspase cleavage was quantified using the GaspaseGlo kit and normalised to cell viability.

FIG. 21: Exogenous rOPCML administration abrogates total RTK levels and inhibits RTK signalling in vitro. (A) Western Blot analysis of pHER, tHER2, tEGFR, pEGFR, tFGFR, pFGFR proteins from SKOV-3 and A2780 cells treated with vehicle only or OPCML (2 µM) for 48 h. (B) Western blot analysis of pAKT, tAKT, pERK, tERK, proteins from SKOV-3 and A2780 cells treated with vehicle only or OPCML (2 µM) for 48 h. Protein loading was standardised by BCA-assay and β-tubulin was used as a loading control.

FIG. 22: Recombinant OPCML treatment reduces tumour growth in vivo. Comparison of r-OPCML and control protein (bovine serum albumen) treated A2780 and SKOV-3 cell lines. (A) Gross anatomical observation of the animals (B) Intraperitoneal tumour growth assay. Tumours were removed, weighed and photographed after 3 weeks of twice-weekly 1 mL intraperitoneal injection of 10 µM r-OPCML or BSA. Representative A2780 and SKOV-3 tumour xenografts from 4 animals are presented. A scale bar is shown. (C) mean tumour weight, (D) number of deposits and (E) volume of ascites removed per mouse from the intraperitoneal assay presented in B. Comparison is shown between tumours and ascites collected from BSA-(−) and r-OPCML-treated (+) mice. (F) Western blot analysis of recovered tumours from control (BSA) and r-OPCML treated animals recapitulates in-vitro findings.

EXAMPLE 1: OPCML TUMOR SUPPRESSOR FUNCTIONS AS A REPRESSOR-ADAPTOR, NEGATIVELY REGULATING RECEPTOR TYROSINE KINASES IN BOTH NORMAL OVARIAN SURFACE EPITHELIUM AND OVARIAN CANCER

Summary

Epithelial ovarian cancer (EOC) is the leading cause of death from gynecologic malignancy. Its molecular basis is poorly understood but involves dysfunction of p53 (Hall et al (2004) "Critical evaluation of p53 as a prognostic marker in ovarian cancer". Expert Reviews in Molecular Medicine 6: 1-20), BRCA1 and −2 (Radice (2002) "Mutations of BRCA genes in hereditary breast and ovarian cancer" *J Exp Clin Cancer Res.* 21(3 Suppl): 9-12), PI3K (Meng et al (2002) "Role of PI3K and AKT specific isoforms in ovarian cancer cell migration, invasion and proliferation through the p70S6K1 pathway" *Cellular Signaling* 18(12): 2262-2271), and growth factor and angiogenic signaling pathways (Maihle et al (2002) "EGF/ErbB receptor family in ovarian cancer" Cancer Treat Res. 107: 247-58; Le Page et al (2006) "Gene expression profiling of primary cultures of ovarian epithelial cells identifies novel molecular classifiers of ovarian cancer" *British Journal of Cancer* 94: 436-445; Birrer et al (2007) "Whole genome oligonucleotide-based array comparative genomic hybridization analysis identified Fibroblast Growth Factor 1 as a prognostic marker for advanced-stage serous ovarian adenocarcinomas" *Journal of Clinical Oncology* 25(16): 2281-2287; Trinh et al (2009) "The VEGF pathway and the AKT/mTOR/p70S6K1 signaling pathway in human epithelial ovarian cancer" *British Journal of Cancer* 100: 971-978; and Lafky et al (2008) "Clinical implications of the ErbB/epidermal growth factor (EGF) receptor family and its ligands in ovarian cancer" *Biochim Biophys Acta.* 1785(2): 232-65).

We previously identified opioid binding protein cell adhesion molecule (OPCML) as epigenetically inactivated in 83% of ovarian cancers and demonstrated that it was a functional tumor suppressor in vitro and in vivo (Sellar et al (2003) "OPCML at 11q25 is epigenetically inactivated and has tumor-suppressor function in epithelial ovarian cancer" *Nat. Genet.* 34(3): 337-43). Here, we show that OPCML interacts with and downregulates HER2 and FGFR1 proteins, leading to inhibition of those signaling pathways, with consequent inhibition of in-vitro growth in SK-OV-3 ovarian cancer cells. siRNA knockdown of physiologically expressed OPCML in OSE-C2 normal ovarian surface epithelial cells strongly upregulated HER2 and FGFR1. OPCML sensitized HER2 positive ovarian cancer cells to lapatinib and trastuzumab in vitro and was a good prognostic indicator in patients with HER2 positive ovarian cancer. The finding that OPCML actively mediates negative regulation of multiple RTK pathways opens novel research avenues in normal cell and cancer biology.

Experimental Procedures

Antibodies

The polyclonal goat and monoclonal mouse anti-OPCML antibodies were purchased from R&D. Anti-HER2 antibodies were purchased from Calbiochem (anti-ErbB2 (Ab-4) and (3B5) mouse MAbs). Anti-EGFR antibody was from R&D Systems. Anti-EGFR goat pAb-cat no AF-231. Phospho-specific EGFR and HER2 antibodies were purchased from AbCam. Anti-HA antibody was from Santa Cruz Biotechnology (Santa Cruz CA) HRP-conjugated secondary antibodies were from Dako. Alexa-Fluor 488 goat anti-rabbit IgG, Alexa-Fluor 555 goat anti-mouse were from Molecular Probes (Eugene, OR).

Cell Culture

The SK-OV-3 derived OPCML expressing lines (SKOBS-3.5, BKS2.1 and empty vector SKOBS-V1.2) were described previously (Sellar et al, 2003). Stimulation time courses were undertaken with 50 ng/ml human recombinant epidermal growth factor (hrEGF-Promega) following serum-starvation overnight.

Plasmid Constructs

The OPCML cDNA expression plasmids in pcDNA3.1zeo previously described (Sellar et al, 2003) were used for transient transfections. The cDNAs encoding all three Ig domains and domains 1 and 2 were generated by PCR and introduced into the bacterial GST-fusion expression vector pGEX-6P-1 (GE-Healthcare) and sequenced to confirm their fidelity. Vector pIRES-AcGFP1 (Clontech) was employed in transient transfections of OPCML complete cDNA. The HA-tagged Ubiquitin pRK5-HA-Ubiquitin-WT was obtained from Dr. Luke Gaughan, Newcastle University, and the EGFR and HER2 cDNA in pcDNA-3.1zeo was provided by Prof. Bill Gullick, University of Kent. FGFR1 cDNA clones was provided by Prof. Graeme Guy, FGFR1 extracellular domain clones provided by Prof. Kyung Hyun Kim.

Expression of Recombinant OPCML and FGFR Ectodomain

Recombinant proteins were produced in the BL21 bacterial cell line (Promega) as described.

Solubilisation and Refolding of Inclusion Bodies

Inclusion bodies were solubilised in denaturation buffer (8 M Urea, 20 mM Tris-HCl, pH 8.0, 150 mM NaCl and 10 mM DTT) to a final concentration of 5 mg/ml. The suspension was centrifuged and filtered through 0.45 μm membrane filter. Refolding of proteins was undertaken by extensive dialysis against cold PBS in 10 kDa MWCO dialysis tubing. The suspension was then centrifuged and filtered to remove insoluble protein precipitates and soluble aggregates. Protein concentrations were monitored throughout the experiment with protein assay reagent (Bio-Rad Laboratories, California) using bovine serum albumen as a standard RNA Extraction and cDNA Synthesis Total RNA was extracted from cell pellets using TriReagent® (Sigma-Aldrich, Dorset, UK) following their protocol. Synthesis of cDNA was from 1 μg of RNA template with OligodT$_{15}$ primers (Promega, UK), by Moloney-Murine Leukaemia Virus Reverse Transcriptase (MMLV-RT) (Promega, UK) and cDNA was stored at −20° C.

qRT-PCR

Primers were designed using PerlPrimer v.1.14 open source software. Custom oligonucleotide synthesis was carried out by Invitrogen, UK. Quantitative reverse-transcription PCR (qRT-PCR) analysis of gene expression was carried out on an Applied Biosystems 7900HT thermal cycler using SYBR green I technology. Premixed qPCR reagent, Platinum® Quantitative PCR SuperMix-UDG with ROX (Invitrogen, UK), was used for amplification. The expression of specific genes was normalized to the expression of the endogenous control gene HPRT1.

Co-Immunoprecipitation and Pull-Down Assays

Cell layers were washed in PBS and incubated for 30 minutes in lysis buffer (1% TritonX-100, 10 mM Tris pH8.0, 150 mM NaCl, 2.5 mM MgCl$_2$, 5 mM EGTA, 1 mM Na$_3$VO$_4$, 50 mM NaF and protein inhibitor cocktail (Roche). Cell Lysates were then cleared by centrifugation at 13,000 rpm for 20 minutes at 4° C. and aliquots containing equal amounts of protein were incubated with the appropriate antibody before addition of secondary antibody conjugated to sepharose resin. Beads were then washed 3× with lysis buffer and eluted by heating for 5 minutes in 50 μl of SDS sample buffer.

Pull-down assays were performed using recombinant GST-OPCML fusion proteins bound to magnetic glutathione beads (Promega). Cell lysates prepared as for immunoprecipitation, proteins produced using TNT in vitro Rabbit reticulocyte lysate expression system (Promega) or expressed in bacteria were used analysed for interactions.

Immunofluorescent Microscopy

Cells grown on glass slides were fixed in 4% paraformaldehyde for 10 minutes at room temperature. Cells were then permeabilized for 20 minutes with PBS containing 0.2% Saponin prior to blocking in PBS containing 10% goat serum, 2% albumen 2% fetal calf serum for 1 h. Slides were incubated with appropriate combinations of mAb OPCML, mAb HER2 and pAb EGFR primary antibodies for 1 h at room temperature, followed by incubation for 1 h with animal anti-mouse Alexa-555 (OPCML), animal anti-rabbit Alexa 488 (HER2) before mounting and imaging on a Zeiss LSM 510 confocal microscope.

siRNA Knockdown

Endogenous OPCML was knocked down in OSE-C2 cells by transient transfection of a specific pool of 3 siRNAs (Stealth knockdown-Invitrogen) using lipofectamine RNAiMAX reagent.

MTT Proliferation Assay

Cell proliferation assays were carried out in quadruplicate using the thiazolyl blue tetrazolium bromide (MTT) assay. Cells were plated out in 96-well plates at a density of 2,000 cells/well and cultured in low serum medium (0.25% FCS) or low serum medium supplemented with 50 ng/ml EGF. At appropriate time points, the medium was removed from cells and replaced with 100 μl PBS and 11 μl of 5 mg/ml MTT (w/v). Cells were incubated in this solution for 2 hours at 37° C. and the purple fomazan product was solubilised in 100 μl DMSO, resuspended and read on plate reader at 540 nm.

Statistical Analyses

Data are expressed as mean±SEM. Differences were analysed by Fishers exact or Student's t test. P<% 0.05 was considered significant. Progression-free survival curves were estimated using the Kaplan-Meier method and analysed by the log-rank test. Correlation between the mRNA expression indices of genes was analysed using Pearson's correlation analysis.

Statistical Analysis and Mining of Tothill Data

Gene expression data on the 251 epithelial ovarian cancers within 285 ovarian tumors (published by Tothill et al (2008) *Clinical Cancer Research* 14: 5198) were obtained from the Gene Expression Omnibus (GEO). OPCML, EGFR and ERBB2 gene expression Pearson correlation coefficients were computed for all probe-sets. For survival analyses included all patients followed up to 5-years, and excluded patients with borderline/low malignant potential histology in view of their distinct natural history compared to invasive tumors. The effect of gene expression (probe: OPCML 206215_at, ERBB2 210930_s_at) on survival was assessed as a continuous variable using Cox-regression, and after transformation to categorical variables by median dichotomization or quartiles using Kaplan-Meier curves and the log-rank test.

Results

OPCML is Rapidly Induced by EGF and FGF 1/2

Serum starved SK-OV-3 cells (low OPCML expression) {Sellar, 2003 #2} were stimulated with 50 ng/ml EGF or 10 ng/ml FGF. EGF induced OPCML rapidly, achieving maximal mRNA expression at 30 min, with return to basal levels of expression by 60 min (FIG. 1A(i)), with maximal OPCML protein at 60 min (FIG. 1A(ii)). Similarly, FGF1/2 also induced OPCML mRNA, by 15 minutes (FIG. 1B(i)) with protein peaking at 90 minutes (FIG. 1B(ii)). These data were replicated for several other cell lines (data not shown). Specifically, induction of OPCML expression in a panel of ovarian cancer cell lines upon EGF stimulation (50 ng/ml) demonstrated consistent induction of OPCML mRNA by 5 to 10-fold, with varied timescale of peak induction.

OPCML Interacts with HER2 and FGFR1 Via Different Binding Sites

To determine if OPCML interacted with RTKs, co-immunoprecipitation (co-IP) using an OPCML polyclonal antibody was performed in a SK-OV-3 cell lines stably transfected with OPCML (BKS2.1) and vector-only controls (SKOBS-V1.2). Other OPCML stable transfected clones have been reported previously and behave identically as BKS2.1 (Sellar et al, 2003). Immunoblotting with anti-HER2 and anti-EGFR demonstrated that both interacted with OPCML, however reciprocal Co-IP using anti-HER2 and anti-EGFR antibodies confirmed the Co-IP only for OPCML with HER2 and not with EGFR (FIG. 2A(i & ii)). We further used GST/OPCML domain fusion proteins in pull-down experiments with either SK-OV-3 cell lysates (expressing HER2 and EGFR) or with purified TnT HER2 ECD fragments (structures shown in FIG. 2B). HER2 interacted with a full length OPCML extracellular domain (ECD) fused to GST (GST-OPCML D1+2+3) but not the truncated OPCML ECD lacking Ig domain 3 (GST-OPCML D1+2) from SK-OV-3 lysates (FIG. 2C(i)), in addition to in vitro translated HER2 ECD (FIG. 2C(ii)), suggesting that the third (juxtamembrane) Ig domain (Ig-Ill) of OPCML is crucial for interaction with HER2. We then explored whether OPCML interacted with the fibroblast growth factor receptors 1 and 2 (FGFR1 & 2). Co-IP of SKOBS-V1.2 and BKS2.1 with OPCML antibody revealed that OPCML bound to FGFR1, confirmed by reciprocal co-IP (FIG. 2A(ii)). We used the GST/OPCML fusion proteins in pull-downs using cell lysates transiently transfected with full length FGFR1 (FIG. 2C(i)) and separately in in vitro studies with His-tagged FGFR1 (FIG. 2C(ii)). These experiments showed that both GST-OPCML D1+2+3 and GST-OPCML D1+2 interacted with FGFR1, therefore domain 3 was not essential for FGFR1 binding, implying that FGFR1 and HER2 bound to different sites on OPCML. Further experiments showed that GST-OPCML D2+3 interacted with FGFR1 but not GST-OPCML D3, showing that domain 2 is essential for FGFR1 binding (data not shown).

OPCML Downregulates HER2 and FGFR1, and Abrogates Phosphorylation of HER and EGFR, Together with Downstream Signaling of the MEK-ERK Cascade We then explored the functional consequences of these OPCML-RTK interactions. OPCML expressing BKS2.1 demonstrated strong downregulation of HER2 but not EGFR protein as compared with SKOBS-V1.2 (FIG. 3A(i)), implying that OPCML specifically regulates HER2 protein. We extended our investigations to the FGF receptor family and demonstrated downregulation of FGFR1 but not FGFR2 in BKS2.1 (FIG. 3A(ii)). Immunofluorescence microscopy (IFM) confirmed that OPCML expression in BKS2.1 dramatically reduced the levels of HER2 and FGFR1 but not EGFR or FGFR2 (FIGS. 3B(i & ii) and 3E).

We explored the impact of OPCML on cellular RTK phospho-activation and signaling in ovarian cancer cells. Phosphorylation of 2 analogous autophosphorylation sites, HER2-Y1248 and EGFR-Y1173 was abrogated in BKS2.1 (FIG. 3C(i)) (an independent OPCML stable transfectant, previously described (Sellar et al (2003)) (data not shown), and OSE-C2 expressing physiological levels of OPCML (data not shown). Similarly, FGF mediated phosphorylation of FGFR1-Y766 (known to transactivate phospho lipase Cγ) was abolished in BKS2.1 cell lines (FIG. 3C(i)). In both EGFR and FGFR signaling systems, we noted inhibition of phospho-PLC. and phospho-ERK 1& 2 (T202 & Y204—FIG. 3C(ii)) but not phospho-Akt S473 or T308 (FIG. 3C(iii)) suggesting that OPCML principally affected the MEK-ERK cascade. These signaling findings were phenotypically confirmed in growth assays; BKS2.1 and SKOBS-3.5 lines and OSE-C2 were profoundly growth-inhibited compared with vector control SKOBS-V1.2 (p<0.0001, student's t-test) (FIG. 3C(iv)).

To explore the physiological role of OPCML, normal epithelial cell line OSE-C2 (OPCML expressing) was transfected with OPCML siRNA, which abolished OPCML protein. This resulted in a strong induction of HER2 and FGFR1 (but not EGFR or FGFR2) and phospho activation of HER2-Y1248 and EGFR-Y1173 levels (FIG. 3D(ii)). Since OPCML expression and physiological function seems to be regulated by growth factor signaling and it is downregulating at least two members of two different families of RTKs, we decided to extend our analysis to other RTKs. SiRNA against OPCML was used to verify whether RTKs appearing downregulated in the OPCML-expressing lines would show reciprocal upregulation if OPCML is knocked down in OSE-C2 cells. From this analysis, in addition to HER2, HER4 also appears downregulated in both SKOBS-3.5 and BKS2.1 cells, whereas FGFR1 and FGFR3 appear downregulated in predominantly the BKS2.1 line expressing five times more OPCML than SKOBS-3.5 (FIG. 3D(i)). The reciprocal analysis of looking at RTK expression after OPCML knockdown revealed HER2, HER4, FGFR1, all showing substantive upregulation in siRNA lane. FGFR3 exhibits a slight increase in expression level with knockdown (FIG. 3D(ii)). In contrast OPCML does not affect EGFR, HER3, FGFR2, FGFR4, EPHA50, VEGFR1 and VEGFR3.

OPCML Prevents HER2/EGFR Hetero Dimer Formation and Reduces EGF Receptor Availability.

SKOBS-V1.2 and BKS2.1 cell extracts were subjected to Co-IP and immunoblotted with antibodies as shown in FIG. 4A, demonstrating loss of hetero-dimerisation in the presence of OPCML. Further, OPCML reduced EGF receptor availability (FIG. 4B).

OPCML is Localized in the Detergent—Resistant (Raft) Membrane Fraction and Co-Localizes with EGFR and HER2 in Ovarian Cancer Cells.

To define the mechanism of OPCML-based RTK degradation, we used HER2 as a paradigm for further study. Initially, we investigated the influence of OPCML expression upon the mode of HER2 degradation linked to immunofluorescent confocal microscopy (IFM) analysis to examine the trafficking of OPCML and HER2 in cells. It has been previously reported that GPI-anchored proteins are sequestered in the detergent insoluble 'lipid-raft' membrane microdomain of cells (Sangiorgio et al (2004) Ital J Biochem 53(2): 98-111). To examine the localisation of OPCML (a GPI anchored protein) within lipid rafts, purified membrane of OPCML negative (SKOBS-V1.2) and positive (BKS-2.1) were subjected to solubilisation in 1% Triton X100 (for detailed method see Materials and Methods) and samples subjected to ultracentrifugation to separate detergent solubilised and insoluble proteins (FIG. 5A(i)). This experiment revealed that the majority of OPCML was localized within the detergent insoluble fraction, along with Caveolin-1 (a marker of caveolae—a distinct form of lipid raft domain). Interestingly, HER2, in the OPCML-expressing line, was reduced as previously shown in FIGS. 3A and 3B but also sequestered in the detergent insoluble fraction when compared to the OPCML negative line, where HER2 was equally distributed. The distribution of EGFR was only marginally effected by the expression of OPCML. IFM was employed to examine the trafficking of OPCML in cells; EEA-1 (a marker of the early endosome) and caveolin-1 (a marker of the raft-caveolar pathway) were used to distinguish between Clathrin-coated pit and caveolar endocytic vesicles. These studies revealed that the majority of the internalized protein co-localized with Caveolin-1 compared to EEA-1 (OPCML+cell line: cav-1 co-localisation=23%, EEA-1=7.5% of total HER2; OPCML-cell line: cav-1 co-localisation=4.5%, EEA-1=32% of total HER2). Furthermore, vesicular staining was seen to be markedly different within the cell, consistent with these representing distinct compartments (FIG. 5A(ii)). IFM also confirmed that OPCML co-localized with EGFR and HER2 in ovarian cancer cells (FIG. 5A(iii)).

We next transfected both OPCML-expressing and non-expressing cell lines with a HA-tagged ubiquitin construct to analyze the levels of receptor ubiquitination +/−OPCML. Twenty four hours post transfection, cells were serum starved and subjected to acute stimulation with EGF (50 ng/ml) for 60 minutes. Consistent with the significant reduction in receptor levels, OPCML expression was associated with enhanced ubiquitination of HER2, which was strongly increased upon EGF stimulation (FIG. 4B(i&ii)). IFM and quantification of co-localisation demonstrated that OPCML expression induced a shift in proportion of the HER2 into caveolin-1 positive vesicles compared to a predominant co-localisation with EEA-1 in the OPCML negative cell line (+OPCML: HER2/CAV-1, 22.863%±1.859; HER2/EEA-1 8.767±1.852.−OPCML: HER2/CAV-1, 4.767%±1.559; HER2/EEA-1 30.667±3.756) (FIG. 5C(i&ii)). Transmembrane proteins in the EEA-1 compartment can enter either the late-endosome-lysosome for degradation, or the Rab11-positive recycling endosome. Whilst Caveolin-1 positive vesicles have been reported to be non-recycling and result in proteasomal degradation of their cargo (Di Guglielmo et al (2003) *Nat Cell Biol* 5: 410-421). Consistent with degradation by the proteasome, chloroquine (CQ), a weak base that alkalinises the lysosome, was ineffective, but MG-132, a potent antagonist of the proteasomal 26S proteinase, inhibited HER2 degradation in the OPCML expressing cell line with no effect on EGFR expression found (FIG. 5D(i&ii)). Furthermore, disruption of cholesterol using methyl-R-cyclodextrin (MP-CD) also inhibited the degradation of HER2 and increased the phosphorylation at Y1248 (FIG. 5D(iii)) suggesting an important role for the lipid-raft in the OPCML-specific regulation and degradation of HER2. In conclusion, OPCML binds specifically to HER2, sequesters the receptor in lipid-rafts, enhancing caveolar-based endocytosis, ubiquitination and subsequent proteasomal degradation of the oncogenic receptor.

OPCML Regulates/Predicts Response to Lapatinib in Ovarian and Breast Cancer.

The finding that OPCML could regulate activity of HER2 and EGFR led us to explore whether OPCML might influence the efficacy of anti-EGFR/HER2 therapeutics. OPCML transfected and control cells were pre-incubated with lapatinib, trastuzumab, cituximab, erlotinib and gefitinib. We then used EGF induced phospho-ERK activation as an assay to define the effectiveness of therapeutic inhibition. The dual inhibitor of EGFR and HER2 tyrosine kinases, lapatinib, exhibited strong OPCML mediated sensitization, reducing the effective concentration of lapatinib required to abolish the phospho-ERK signal by 10-fold for BKS2.1 compared with SKOBS-V1.2 (FIGS. 6A(i) and 6C). We noted enhanced down-regulation of phospho-AKT in OPCML expressing cells. Lesser sensitization than for lapatinib was observed with trastuzumab (FIG. 6A(ii)). Notably, cetuximab, erlotinib and gefitinib, inhibitors of EGFR showed no sensitization in OPCML transfected cells (data not shown) consistent with the hypothesis that OPCML interacts with HER2 and not EGFR.

We then investigated whether siRNA knockdown of physiological OPCML expression in normal OSE-C2 cells could affect sensitivity to lapatinib. We observed that the lapatinib-mediated reduction in phospho-ERK signal strength was significantly reversed by OPCML siRNA knockdown in these normal ovarian surface epithelial cells (FIG. 6B). These data demonstrate that OPCML modulates sensitivity to lapatinib through regulation of the level of HER2, however the mechanism of this finding remains to be clarified.

We next tested whether OPCML could be used to predict response to lapatinib in ovarian and breast cancer. Histology was obtained by new biopsy of recurrent disease and TTP (time in months to progression from start of therapy until progression) assessed. Docetaxel and anthracyclines were administered for a maximum of 6 cycles and capecitabine was administered until disease progression or unacceptable toxicity. HER2 immunohistochemistry (IHC) was performed using the Dako Herceptest kit: 3+ in all cases. The results are shown in Table 1 below.

TABLE 1

| Case number | Histology | Previous treatment chronology (TTP in months)* | Response to lapatinib | OPCML Score |
|---|---|---|---|---|
| 1. | G2 IDC, ER 6/8, PR 0/8, HER2 3+ | Adjuvant: antracyclines and taxanes (23) then adjuvant trastuzumab (12) Metastatic: Hormonal therapy (12) Capecitabine (1) | SD | − |
| 2. | G3 IDC, ER/PR (0/8), HER2 3+, | Adjuvant: anthracyclines (48) Metastatic: Trastuzumab (8) Capecitabine (2) Vinorelbine (8) Taxanes (5) | SD | − |
| 3. | G3 IDC, ER++, PR++, HER2 3+ (metastatic presentation) | Metastatic: Anthracyclines (12) Hormonal therapy (12) Trastuzumab (5) Taxanes (5) Capecitabine (1) | PD | + |

TABLE 1-continued

| Case number | Histology | Previous treatment chronology (TTP in months)* | Response to lapatinib | OPCML Score |
|---|---|---|---|---|
| 4. | G3 IDC, ER (8/8), PR (8/8), HER2 3+ (metastatic presentation) | Metastatic: Capecitabine (14) Trastuzumab (5) Vinorelbine (4) Taxanes (4) Hormonal therapy (4) | PD | + |
| 5. | G3 ILC, ER/PR (0/8), HER2 3+ (metastatic presentation) | Metastatic: Anthracyclines (3) Taxanes (4) Trastuzumab (4) Gemcitabine and vinorelbine (7) Capecitabine (1) | PR | ++ |
| 6. | G2 IDC, ER/PR (0/8), HER2 3+ | Adjuvant: anthracyclines (7) Metastatic: Taxanes (10) Trastuzumab (12) Vinorelbine (9) | PR | ++ |
| 7. | G2 IDC, ER/PR (0/8), HER2 3+ | Adjuvant: anthracyclines (36) Metastatic: Trastuzumab (5) Taxanes (4) Capecitabine (2) Vinorelbine (4) | PR | ++ |
| 8. | G3 IDC, ER/PR (0/8), HER2 3+, inflammatory | Adjuvant: Anthracyclines and taxanes (14), trastuzumab (8) | PR | +++ |

Estrogen receptor (ER) and progesterone receptor (PR) are either scored using H scores (out of 8) or IHC.
IDC = invasive ductal carcinoma, ILC = invasive lobular carcinoma. SD = stable disease, PR = partial response, PD = progressive disease, by RECIST criteria. Examples of OPCML IHC - to +++ are shown.

OPCML is a Prognostic Factor in Strongly HER2 Expressing Ovarian Cancer

In view of the strong tumor suppressor role of OPCML and these findings, we explored whether its expression was related to ovarian cancer prognosis. We used a recently published expression microarray dataset of 251 ovarian cancers (Tothill et al, 2008) with full clinical annotation and follow-up of patients for progression free survival (PFS). The relationship between OPCML mRNA expression and PFS was examined for all 251 ovarian cancer patients with epithelial ovarian cancers in the dataset. Overall high OPCML expression demonstrated a significant association with better survival, as shown by the Kaplan-Meier curve in FIG. 7A(i) (Log-rank p=0.061 Breslow test p=0.034), although the difference was of modest magnitude. However, because the findings described herein suggested that OPCML's tumor suppressor role was related to repression of HER2 and FGFR1 function we specifically analysed the patient cohort according to their HER2 RNA expression and explored the impact of OPCML expression on this group of patients. We found that OPCML mRNA level was strongly prognostic only for patients expressing top quartile HER2 mRNA levels; patients with above median expression of OPCML had 27 months median PFS (FIG. 7A(ii)) and Table 1 & 2) compared with top quartile HER2 and below median OPCML expression with 13 month median PFS (Log-Rank p=0.004). In contrast, bottom quartile HER2 expressing patients showed similar survival regardless of OPCML expression. This validated our hypothesis that OPCML impacts on an intact HER2 pathway. No significant association was observed for EGFR or FGFR1 and OPCML with PFS in this dataset (data not shown).

A possible explanation for this clinical data is that strong OPCML expression (in the context of strong HER2 expression) regulates HER2 protein level/activity and abrogates HER2 pro-oncogenic signaling with consequent better patient prognosis, whereas tumors with weak OPCML expression and strong HER2 expression have unrestrained HER2 pro-oncogenic signaling and consequently poor prognosis.

DISCUSSION

OPCML therefore has repressor-adaptor function, interacting with HER2 and FGFR1, targeting them for degradation and thereby physiologically negatively regulating both the EGF and FGF signaling pathways in normal ovarian surface epithelium, and conversely, by CpG island somatic methylation, activating both these pathways concurrently in epithelial ovarian cancer.

In summary the OPCML tumor suppressor functions by concurrently negatively regulating HER2 and FGFR1 in normal ovarian surface epithelial cells and in ovarian cancer. This finding has general implications for understanding the relationship of IgLONs to the RTK pathways, and their role in both biology of ovarian surface epithelial cells and also in the understanding of how somatic methylation of this tumor suppressor uncovers such strong pro-oncogenic phenotype driven by several RTK pathways.

Table 2a and b: show case processing summary, means and median survival and data comparisons for the at a depicted in Kaplan Meier curves (FIG. 7(i) and (ii)). P

TABLE 2A

Case Processing summary

| B OPCML 215 | Total No | No of Events | Censored No | Percent |
|---|---|---|---|---|
| Low OPCML | 122 | 93 | 29 | 23.80% |
| High OPCML | 129 | 91 | 38 | 29.50% |
| Overall | 251 | 184 | 67 | 26.70% |

Means and Medians for Survival Time

| | Mean (a) | | | | Median | | | |
|---|---|---|---|---|---|---|---|---|
| | | | 95% confidence interval | | | | 95% confidence interval | |
| B OPCML 215 | Estimate | Std. Error | Lower Bound | Upper Bound | Estimate | Std. Error | Lower Bound | Upper Bound |
| Low OPCML | 20.788 | 1.652 | 17.55 | 24.027 | 14 | 0.625 | 12.775 | 15.225 |
| High OPCML | 24.771 | 1.669 | 21.5 | 28.043 | 19 | 1.101 | 16.343 | 21.157 |
| Overall | 22.866 | 1.187 | 20.539 | 25.193 | 15 | 1.138 | 12.77 | 17.23 |

(a) Estimation is limited to the largest survival time if it is censored

Overall Comparisons

| | Chi-Square | df | Sig. |
|---|---|---|---|
| Log Rank (Mantel-Cox) | 3.522 | 1 | 0.061 |
| Breslow (Generalised Wilcoxon) | 4.502 | 1 | 0.034 |
| Tarone-Ware | 4.451 | 1 | 0.035 |

Test of Equality of survival distribution for the different levels of B_OPCML_215

TABLE 2B

Case Processing summary

| Q-HER2-930 | Total No. | No. of Events | Censored No. | percent |
|---|---|---|---|---|
| Low HER2/Low OPCML | 41 | 33 | 3 | 7.30% |
| Low HER2/High OPCML | 21 | 17 | 4 | 19.00% |
| High HER2/Low OPCML | 17 | 13 | 4 | 23.50% |
| High HER2/High OPCML | 42 | 26 | 16 | 38.10% |
| Overall | 121 | 94 | 27 | 22.30% |

Means and Medians for Survival Time

| | Mean (a) | | | | Median | | | |
|---|---|---|---|---|---|---|---|---|
| | | | 95% confidence interval | | | | 95% confidence interval | |
| Q-HER2-930-OPCML-215-10-11-40-41 | Estimate | Std. Error | Lower Bound | Upper Bound | Estimate | Std. Error | Lower Bound | Upper Bound |
| Low HER2/Low OPCML | 16.016 | 1.73 | 12.624 | 19.407 | 13 | 1.232 | 10.586 | 15.414 |
| Low HER2/High OPCML | 17.026 | 2.393 | 12.337 | 21.716 | 12 | 2.511 | 7.079 | 16.921 |
| High HER2/Low OPCML | 16.243 | 2.909 | 10.541 | 21.946 | 13 | 1.159 | 10.728 | 15.272 |
| High HER2/High OPCML | 30.097 | 3.299 | 23.63 | 27 | 27 | 5.753 | 15.725 | 38.275 |
| Overall | 21.479 | 1.614 | 18.315 | 15 | 15 | 1.47 | 12.119 | 17.881 |

(a) Estimation is limited to the largest survival time if it is censored

Overall Comparisons

| | Chi-Square | df | Sig. |
|---|---|---|---|
| Log Rank (Mantel-Cox) | 13.535 | 3 | .004 |
| Breslow (Generalized Wilcoxon) | 9.200 | 3 | .027 |

Test of equality of survival distributions for the different levels of Q_erb_930_Opcm1_215_10_11_40_41.

EXAMPLE 2: EXOGENOUS OPCML INHIBITS RECEPTOR TYROSINE KINASE SIGNALING AND OVARIAN AND BREAST CANCER CELL GROWTH IN VITRO, WHILE SPARING NORMAL OVARIAN SURFACE EPITHELIAL CELLS

To complement the findings described in Example 1, we expressed and purified recombinant human OPCML and assessed its affect on in vitro tyrosine kinase signaling and cell growth. The results are in agreement with those in Example 1.

FIG. 8 shows purification of recombinant human OPCML expressed in *E. coli*. Expressed OPCML was present in inclusion bodies and was successfully refolded by dialysis into PBS. Recombinant OPCML is a 272 amino acid polypeptide whereas physiologically synthesized OPCML is a 345 amino acid polypeptide. Post-translationally modified OPCML (including N-linked glycosylation) is 55 kDa, whereas without glycosylation, the signal peptide region and the GPI anchor region, OPCML is 31 kDa. The protein and polynucleotide sequences of recombinant human OPCML correspond to SEQ ID Nos: 5 and 6 respectively.

Figure 11:
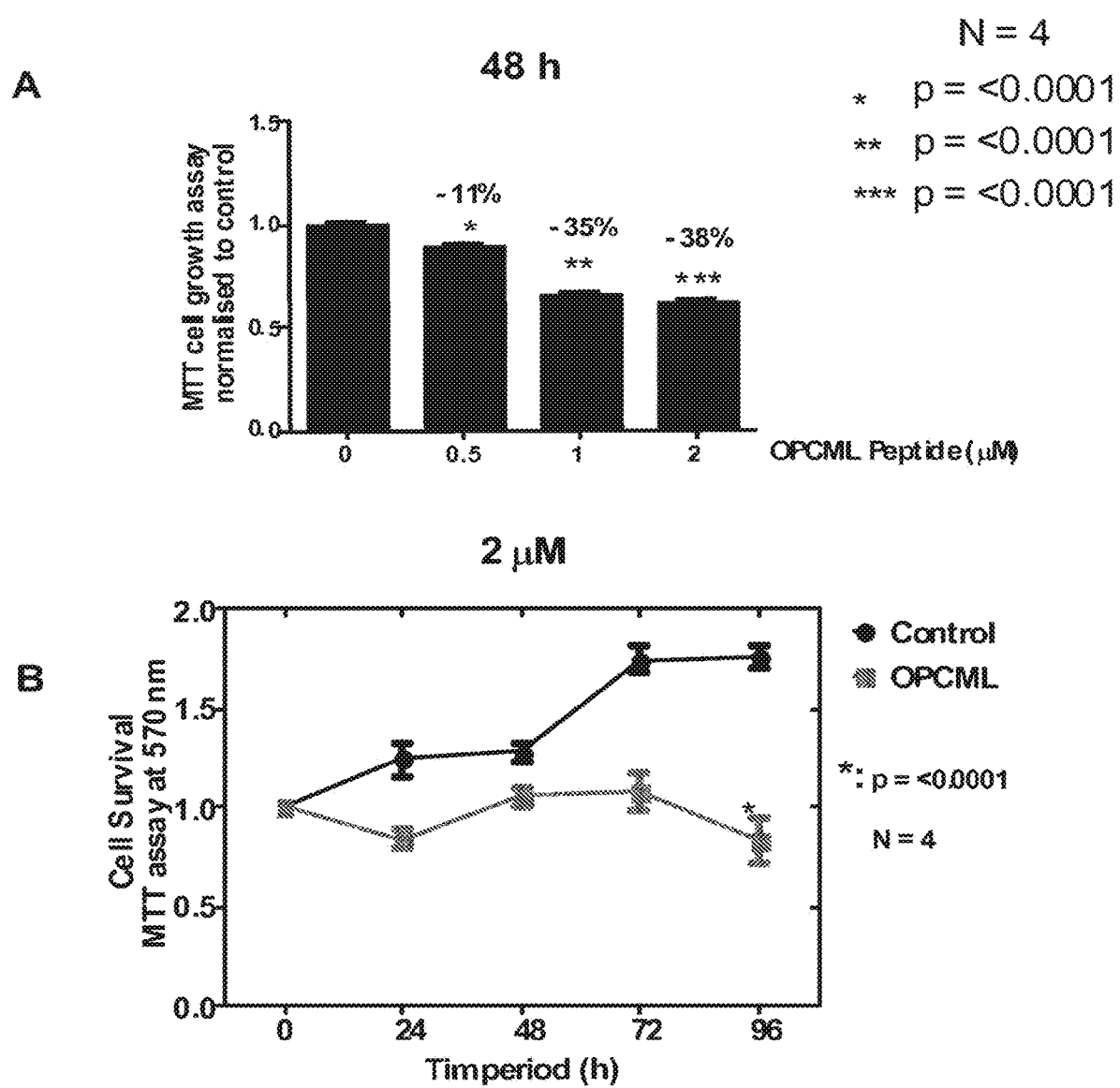
FIGS. 11A and 11B show that administration of exogenous OPCML inhibits SKOV-3 cell growth in vitro, as assessed by a MTT cell growth assay.
Figure 11:
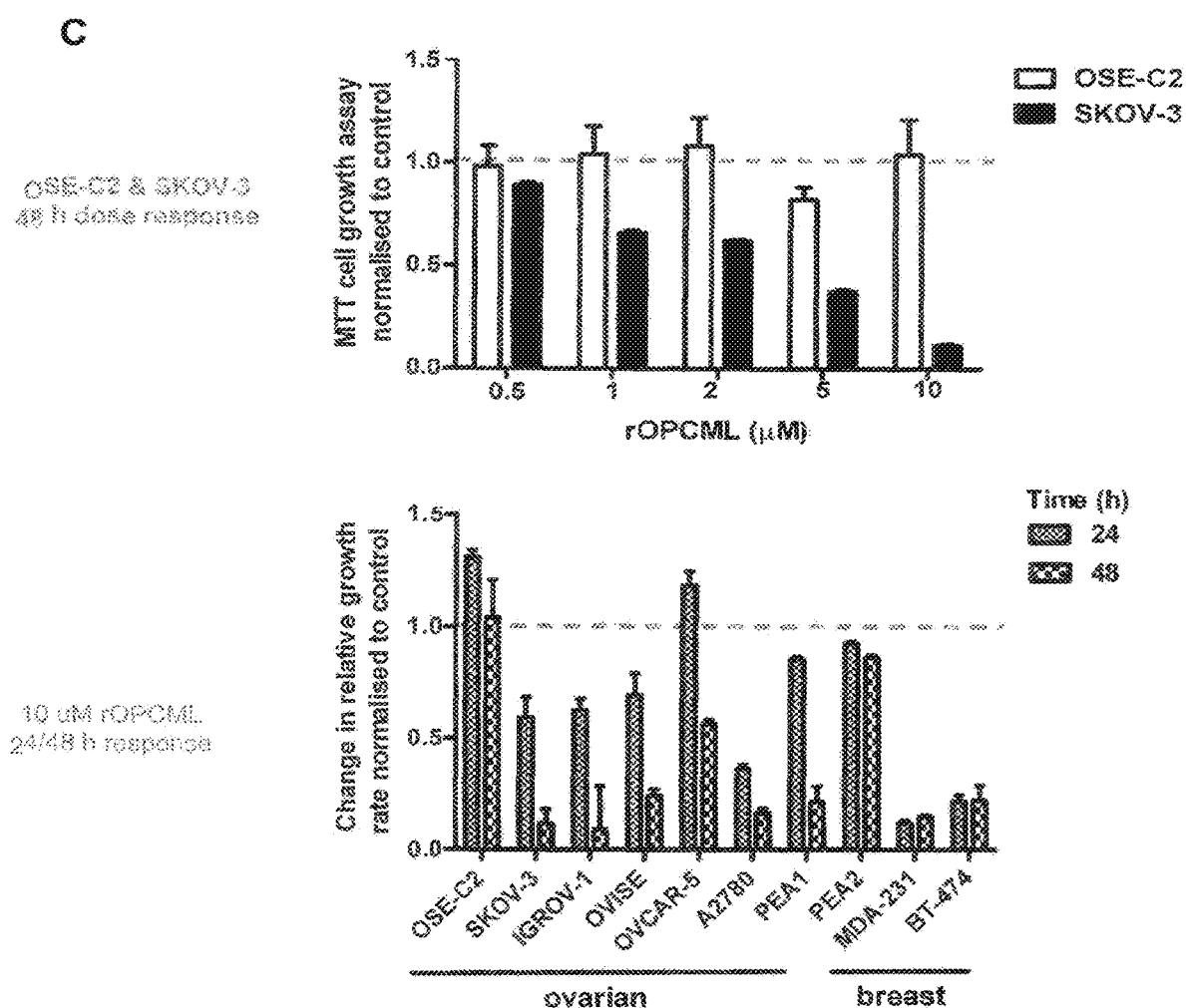

FIG. 11C shows that OPCML inhibits growth of a range of ovarian and breast cancer cell lines, while sparing normal ovarian surface epithelial cells. Interestingly, growth of HER2+ and HER2– breast cancer cell line was profoundly inhibited, suggesting that the mechanism is not solely restricted to HER2+ cells but may be mediated through FGFR pathways or other EGFR components that interact with HER2 and are phospho-inactivated as part of OPCML therapy. Only one cell line showed resistance to OPCML (PEA2).

EXAMPLE 3: OPCML IS A PROGNOSTIC FACTOR IN BREAST, LUNG AND GLIOMA CANCERS

Having established that OPCML is a prognostic factor in strongly HER2 expressing ovarian cancer (see Example 1), we assessed whether its expression was related to the prognosis of other cancers. This was done by a Kaplan Meier analysis of overall survival according to OPCML dichotomized survival.

Figure 12:
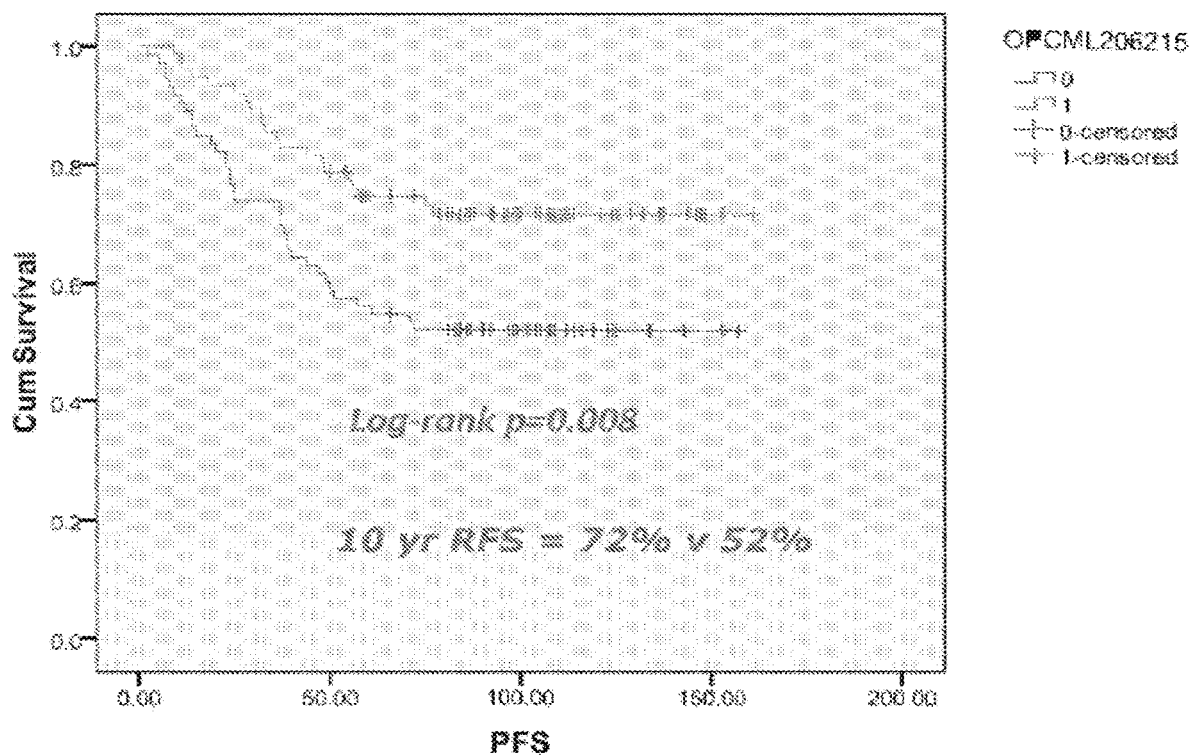
Figure 12:
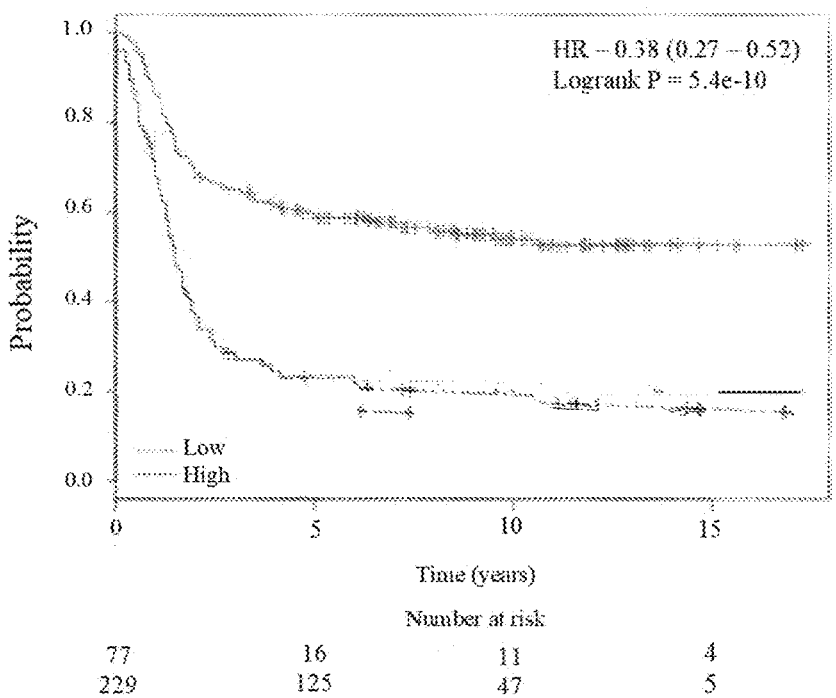
Figure 12:
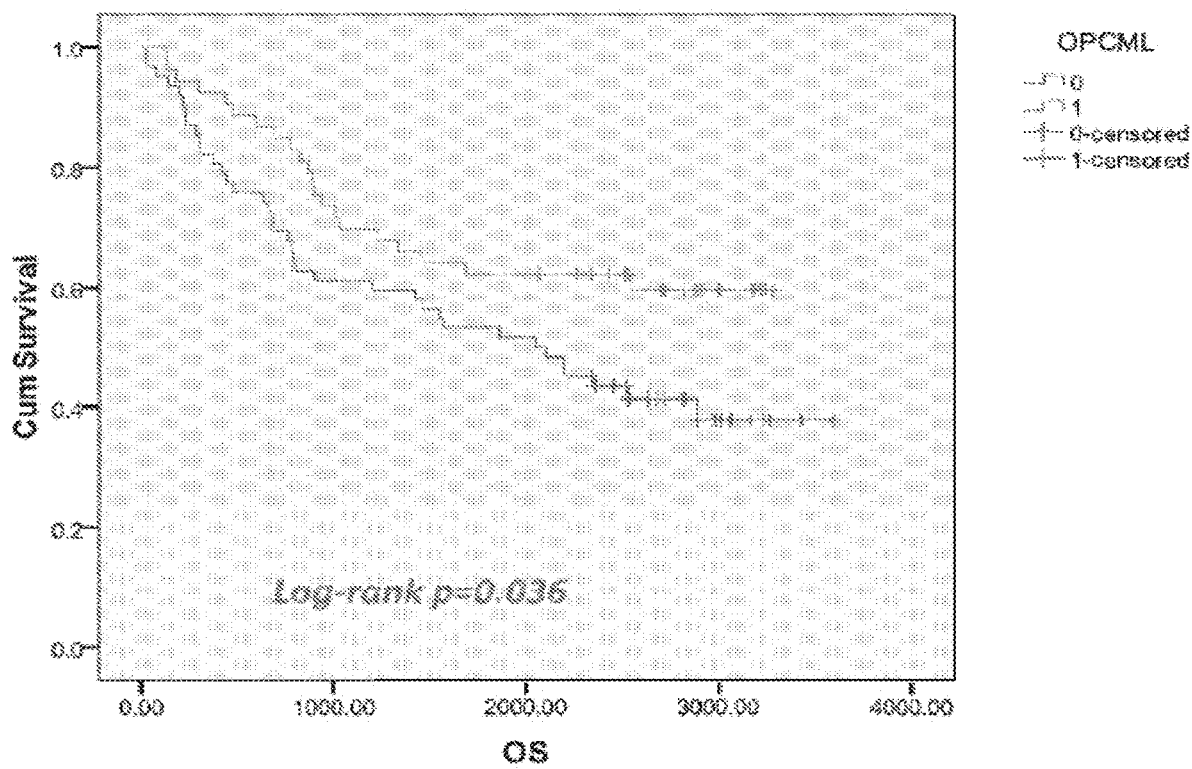
Figure 12:
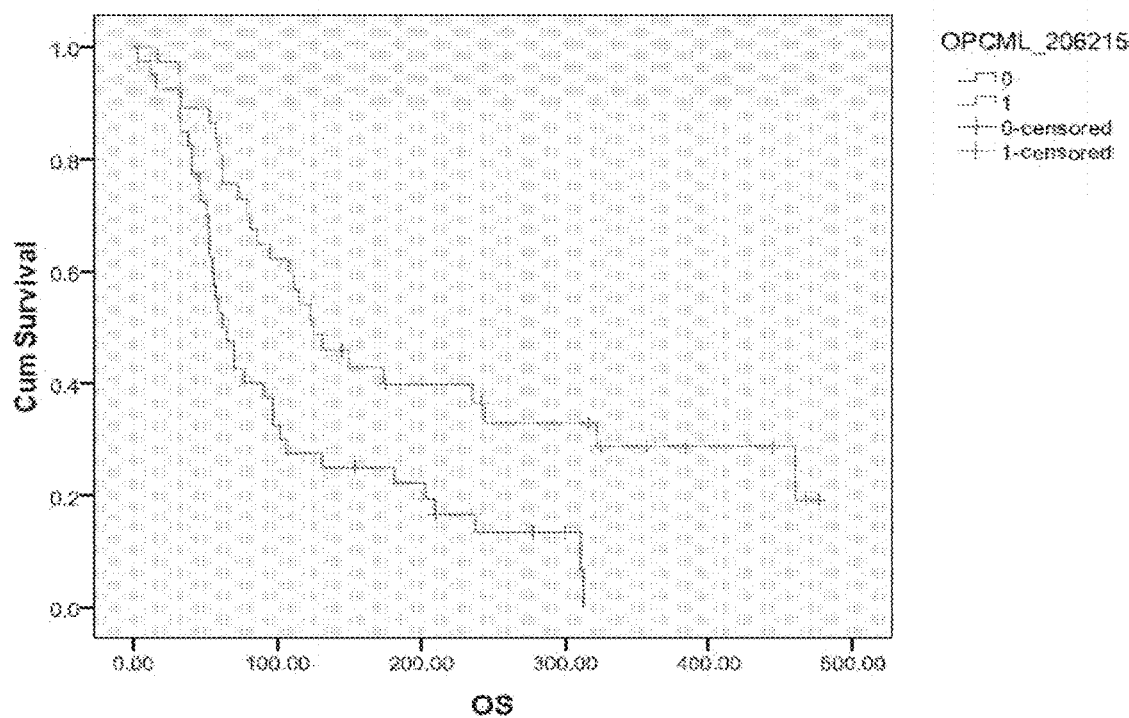
Figure 12:
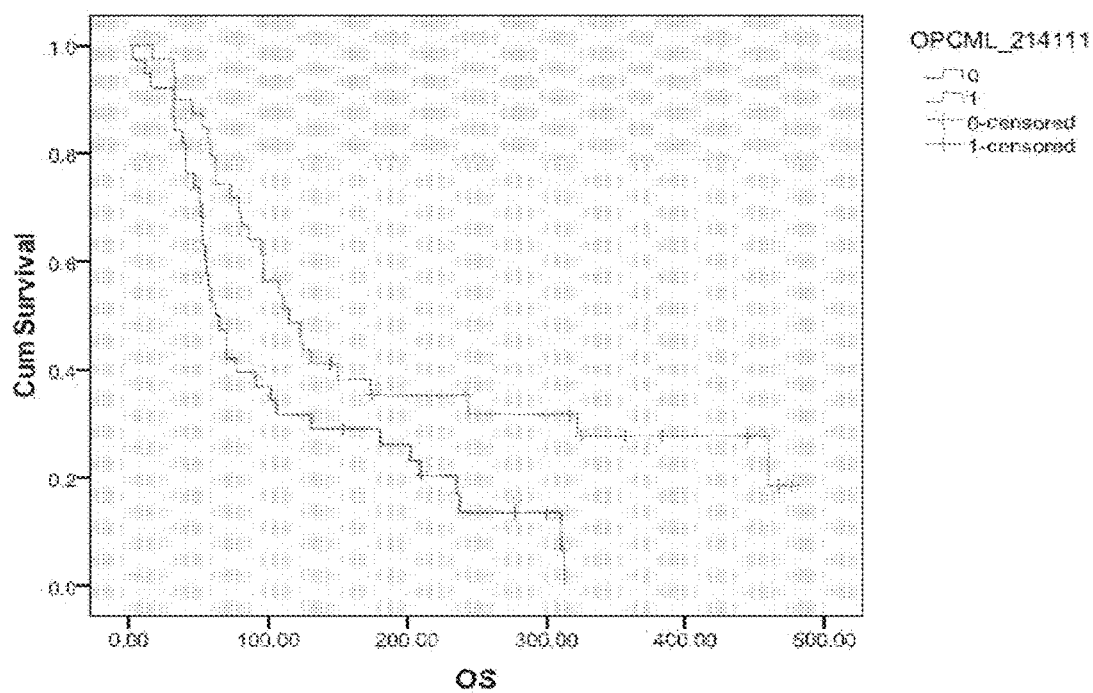

FIG. 12A (first graph—A1) shows that OPCML expression is a good prognostic factor in EGFR/HER2 positive node negative breast cancers in patients receiving no adjuvant systemic therapy. OPCML expressing tumors show better survival, with a 10 year relapse free survival of 72% vs 52%. ('cum survival'=cumulative survival). Analysis was based on a published dataset of 149 node negative breast cancer patients (Wang et al 2005, *Lancet* 365(9460): 671). The second two graphs (A2 and A3) show that OPCML expression is a particularly good prognostic factor in ER- breast cancer.

FIG. 12B shows that OPCML is a prognostic factor in lung cancer. OPCML expressing tumors show better overall survival (OS). Analysis was based on a published dataset of 115 lung cancer patients (Takeuchi et al 2006, *J Clin Oncol* 24(11): 1679-1688).

FIGS. 12C and 12D show that OPCML is a prognostic factor in brain high grade gliomas. OPCML expressing tumors show better overall survival (OS). Analysis was based on a published dataset of high grade glioma patients (Phillips et al 2006 *Cancer Cell* 9(3): 157-73).

EXAMPLE 4: FUNCTIONAL EFFECTS OF OPCML EXPRESSION IN SKOV3 IN VITRO AND IN VIVO

We next investigated the effects of OPCML expression in SKOV3 cells in vivo, using methods described in Sellar et al (2003).

Figure 13:
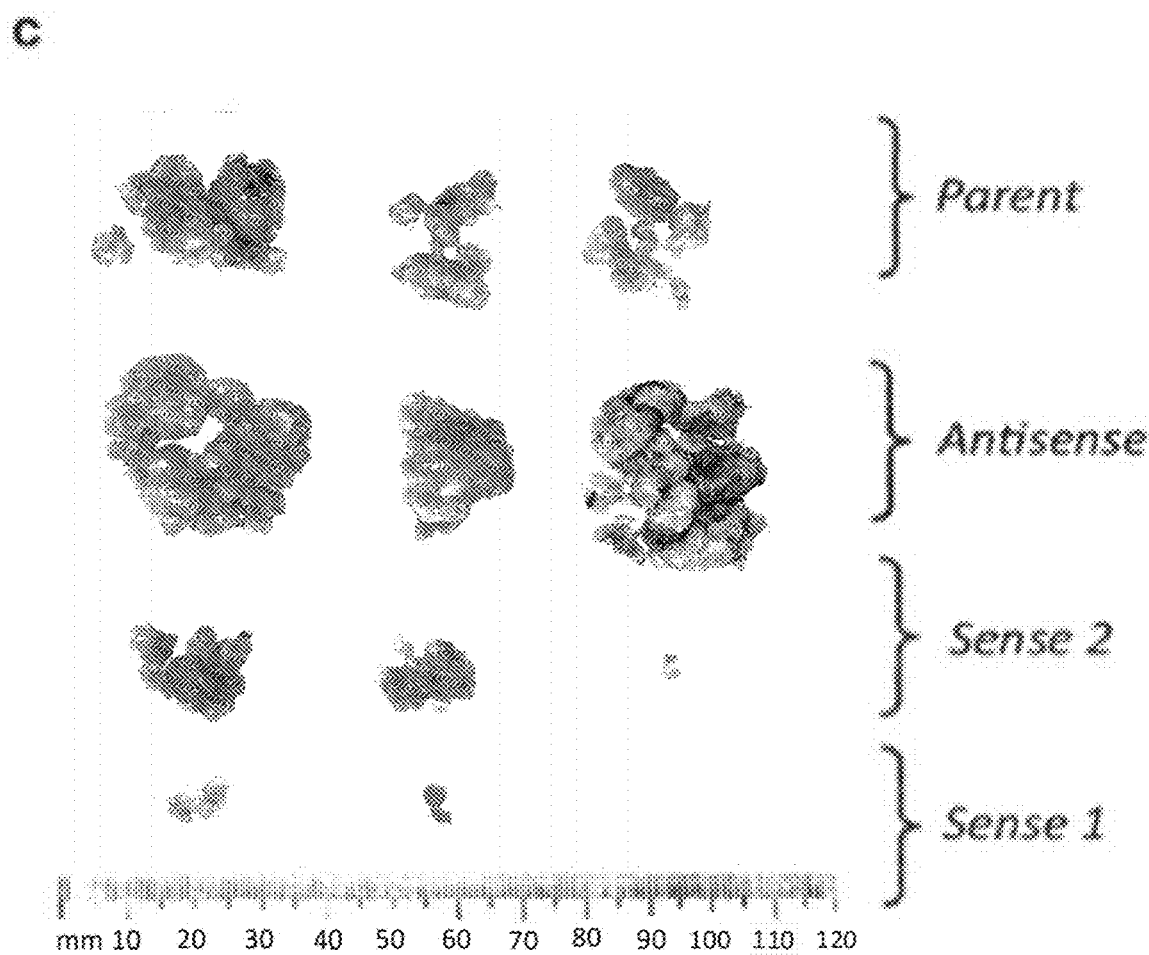

FIG. 13A shows the effect of OPCML expression on in vitro growth of SKOV3 cells, with OPCML expression inhibiting growth relative to normal SKOV3 cells or to SKOV3 cells in which OPCML expression was knocked-down, in agreement with the data described above.

FIGS. 13B and 13C show the effect of OPCML expression on in vivo growth of SKOV3 cells. OPCML expression reduced mean tumor volume relative to normal SKOV3 cells or to SKOV3 cells in which OPCML expression was knocked-down.

EXAMPLE 5: FURTHER STUDIES ON THE ROLE OF OPCML

Summary

OPCML, a GPI anchored tumor suppressor gene is inactivated by somatic methylation in multiple cancers. We previously identified this gene by LOH mapping and demonstrated that it was inactivated by somatic methylation in 80% of ovarian cancers. Restoring OPCML expression by stable transfection suppressed in-vitro growth and in-vivo tumorigenicity. We investigated the role of OPCML in growth signaling pathways. In SKOV-3 and PEO1, ovarian cancer cell lines with no expression of OPCML, we demonstrated that OPCML negatively regulates a specific repertoire of receptor tyrosine kinases (RTKs) EPHA2, FGFR1, FGFR3, HER2 and HER4, and reciprocally, OPCML siRNA knockdown in normal ovarian surface epithelial cells up-regulates these same RTKs. OPCML has no effect on the RTKs EPHA10, FGFR2, FGFR4, EGFR, HER3, VEGFR1 and VEGFR3. Example immunoprecipitation experiments revealed that OPCML binds to EphA2, FGFR1 and HER2 extracellular domains with no such interaction to EGFR, thus OPCML binds directly to RTKS that it negatively regulates. We demonstrate that OPCML is located exclusively in the raft membrane fraction and sequesters RTKs that it binds to the raft fraction, leading to polyubiquitination and proteosomal degradation via a cav-1 endosomal mechanism resulting in systems depletion of this specific RTK repertoire, that does not occur with RTKs that OPCML does not bind. We demonstrate that OPCML abrogates EGF mediated phosphorylation of FGFR1, HER2 and EGFR and the downstream phosphosignaling of pErk and pAKT.

A recombinant modified OPCML-like protein without a GPI anchor, signal peptide or glycosylation was constructed and expressed in *E. coli*. This rOPCML tumor suppressor protein therapeutic caused growth inhibition by apoptosis in 6/7 ovarian cancer cell lines tested, with no effect on OPCML expressing normal ovarian surface epithelium, by an identical mechanism to the transfected normal protein. rOPCML was then injected intraperitoneally twice weekly in two murine intraperitoneal models of ovarian cancer (nude mouse A2780 and SKOV3) and demonstrated profound inhibition of tumour weight, ascites volume and peritoneal dissemination compared with BSA control.

Mechanism of OPCML TSG Function

OPCML is a non-transmembrane, external lipid leaflet GPI-anchored protein, and is frequently lost from cells by somatic inactivation of the gene. We hypothesised that it may mediate its tumour suppressor properties via interactions with transmembrane signalling proteins, and so we analysed the effect of receptor tyrosine kinase (RTK) growth factor stimulation on OPCML gene expression. Treatment of 4/4 ovarian cancer cell lines with EGF or FGF 1/2 resulted in rapid OPCML RNA and concomitant protein expression (data not shown) suggesting that OPCML may be a putative suppressor-type immediate-early negative feedback regulator.

Figure 16:
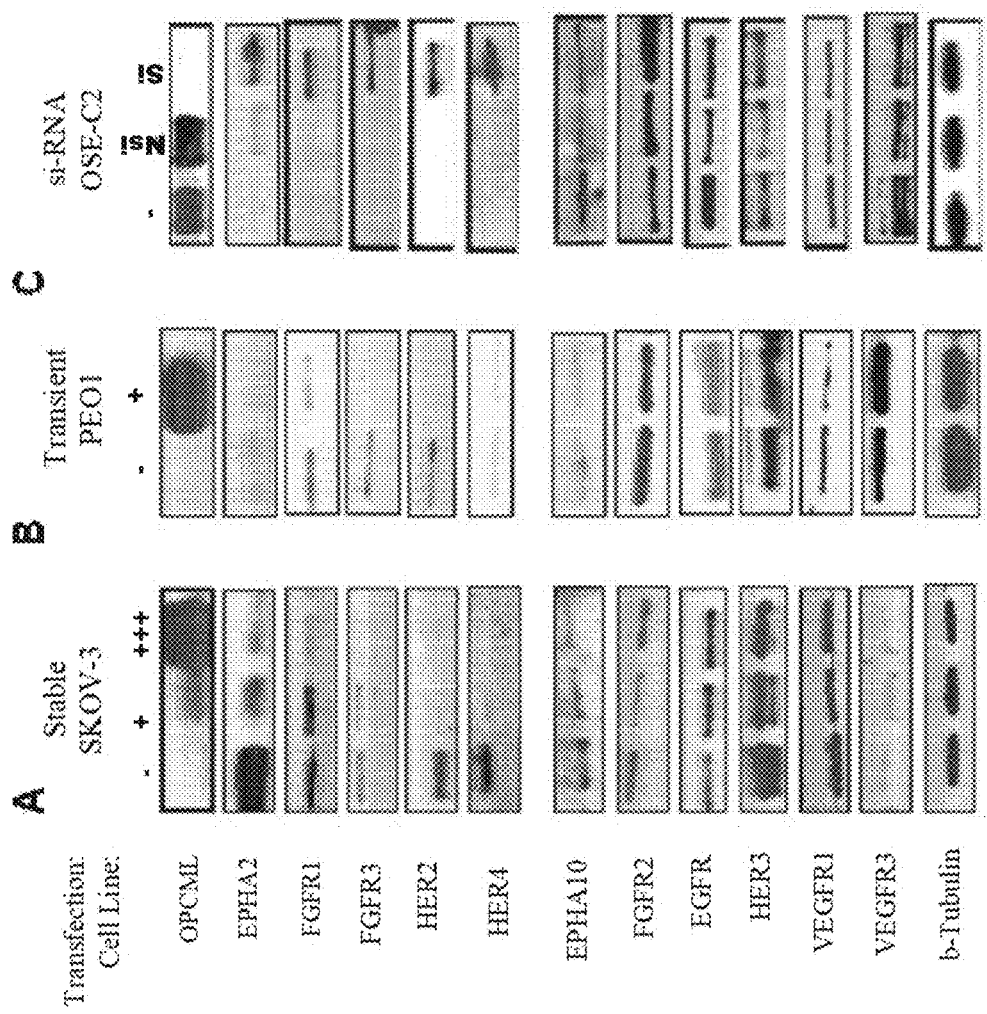

Stable transfection of OPCML in the basal unstimulated or ligand-stimulated SKOV-3 ovarian cancer cells, resulted in the profound protein down-regulation of a specific repertoire of RTKs: EPHA2; FGFR1; FGFR3; HER2 and HER4 (FIG. 16A) and this RTK down-regulation spectrum is reproducible by transient transfection of a different ovarian cancer cell line, PEO1 (FIG. 16B). These same RTKs were also reciprocally up-regulated when physiological OPCML was knocked down by siRNA in OSE-C2, a normal ovarian surface epithelial cell line (Davies et al, (2003) *Experimental Cell Research* 288: 390-402) (FIG. 16C). This specific inactivation by OPCML was not seen for other RTKs we have investigated so far including: EPHA10; FGFR2; FGFR4; EGFR; HER3; VEGFR1 and VEGFR3 (FIG. 16). The phenotypic consequences of these signalling effects were confirmed in growth assays in ligand-supplemented media where OPCML-transfectants were significantly growth-inhibited compared with vector control (data not shown).

Figure 17:
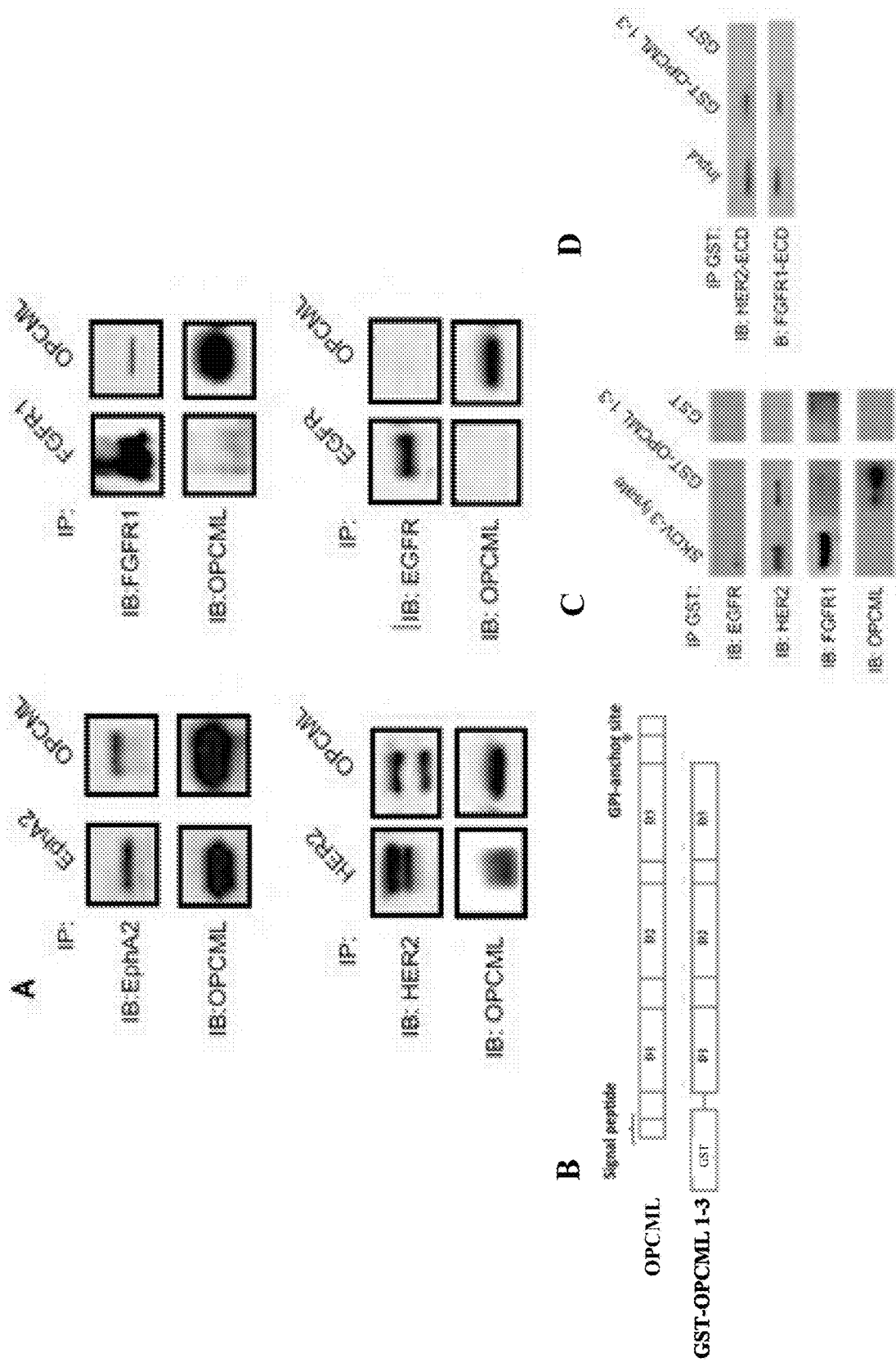

Negative Regulation of Specific RTKs by OPCML is Related to Direct Protein Interaction We further explored as examples EPHA2, FGFR1 and HER2, RTKs that are strongly inactivated at the protein level upon OPCML expression. We also analysed EGFR as an example of a protein that is unaffected by OPCML. Immunoprecipitation (IP) experiments demonstrated protein/protein interactions with EPHA2, FGFR1 and HER2, but no such binding to EGFR (FIG. 17A). These findings were further confirmed using a recombinant OPCML (GST-OPCML D1-3) pull-down assay (FIG. 17B) which was then used to determine that the extracellular domains (ECDs) of the RTKs FGFR1 and HER2 (as examples) were capable of interacting specifically with OPCML (FIGS. 17C&D), showing that the site of interaction lay within the ECD of the RTKs and domain 1-3 of OPCML, defining the site of OPCML action as extracellular.

Downstream Signalling

Figure 18:
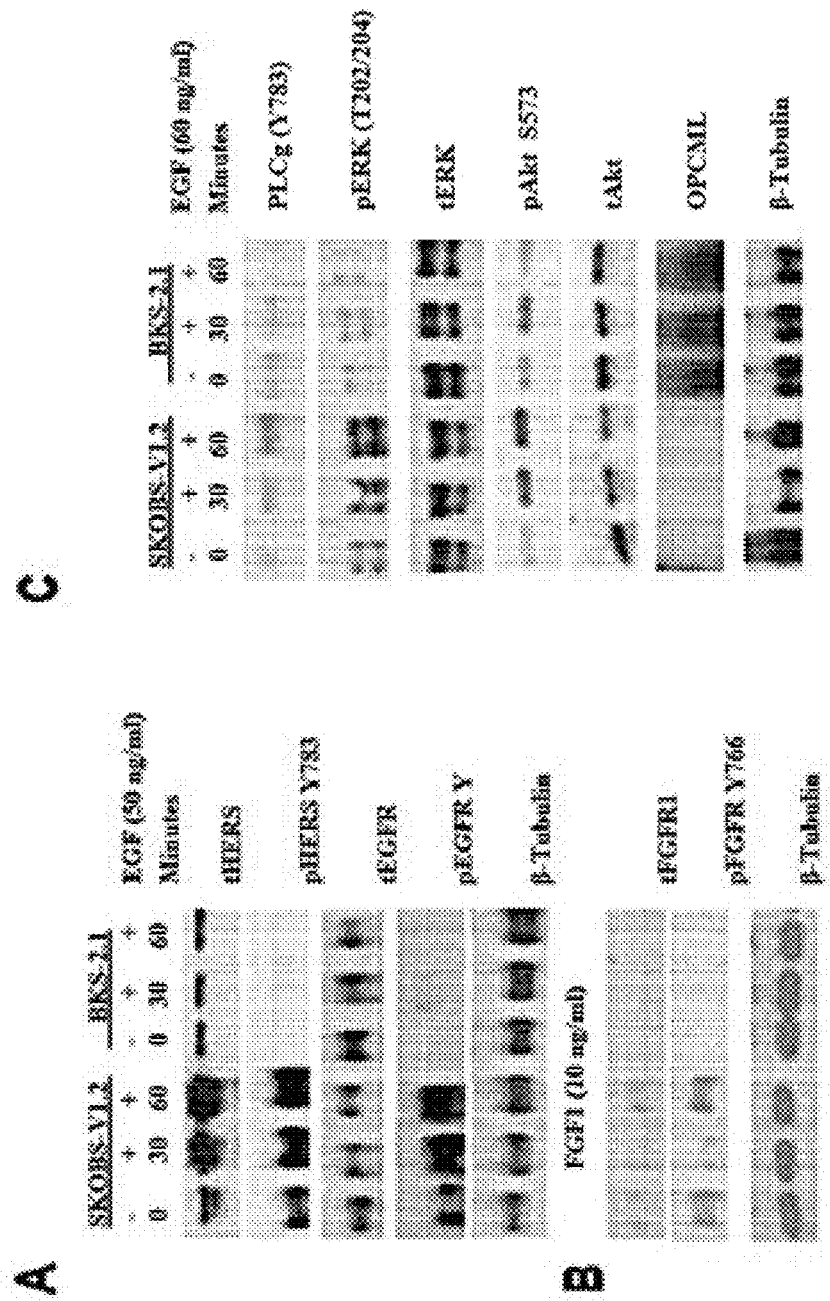

Upon acute ligand stimulation, OPCML expression led to profound abrogation of phospho-FGFR1-Y766, phospho-HER2-Y1248 and, also, phospho-EGFR-Y1173. Whilst EGFR total protein down-regulation is NOT observed, presumably due to the absence of an RTK ECD physical interaction with OPCML, the consequence of OPCML mediated loss of the activating dimerisation partners of EGFR, (HER2 and HER4), coupled with the continuing availability of the HER3 family member (that results in an inhibitory dimerisation with EGFR), explain the down-regulation of EGFR signalling even though total EGFR levels are unaffected (FIG. 18A). Analysis of FGFR1 signalling showed a similar pattern of phospho inhibition relating to protein down-regulation (FIG. 18B).

Analysis of downstream signalling demonstrated abrogation of phospho-ERK 1 & 2 (T202 & T204) and phospho-AKT-S473 (FIG. 18C), suggesting that both pro-growth and pro-survival pathways are inhibited by OPCML re-expression, via a systems level abrogation of this specific RTK spectrum.

OPCML-Mediated RTK Degradation Mechanism

Figure 19:
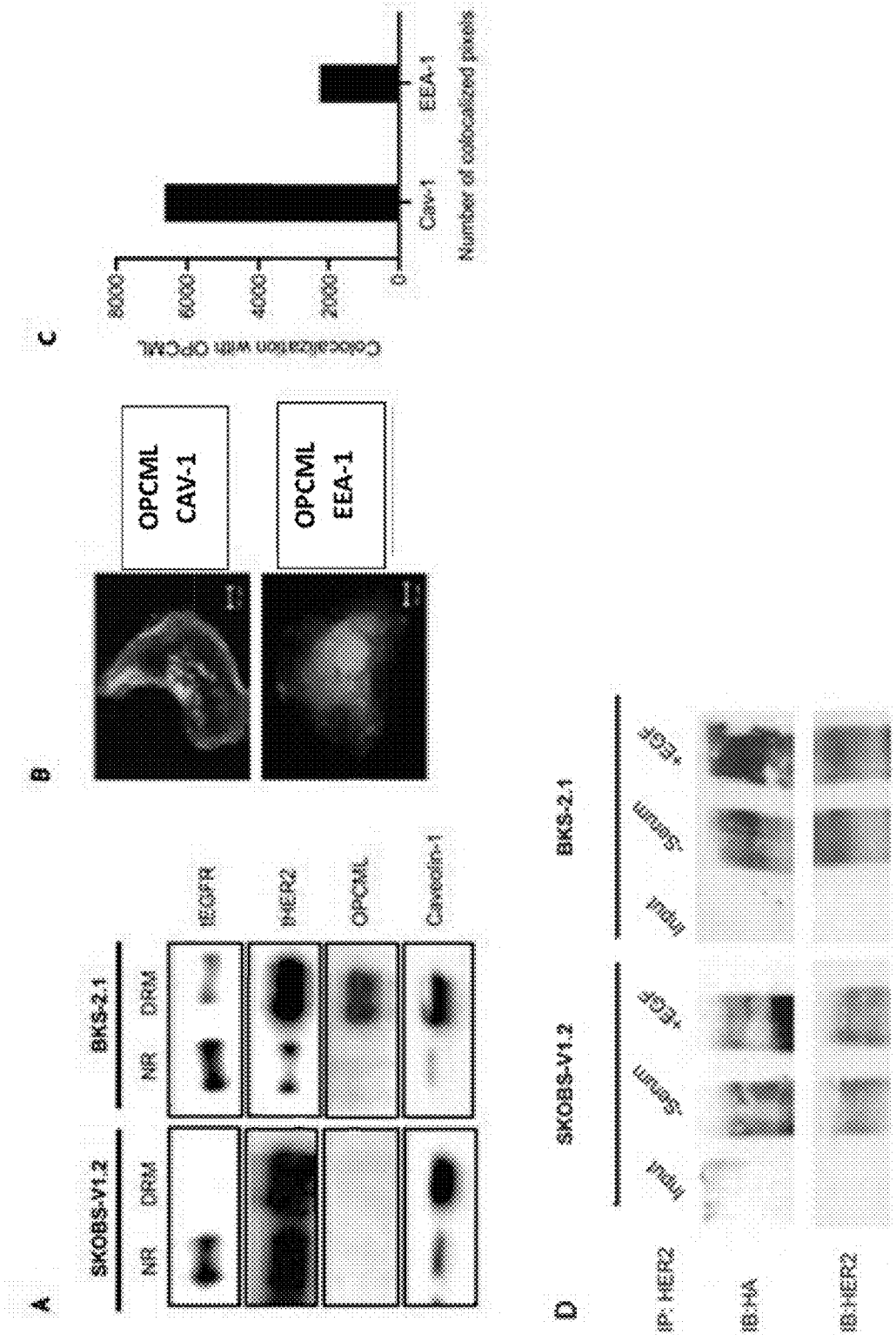
Figure 19:
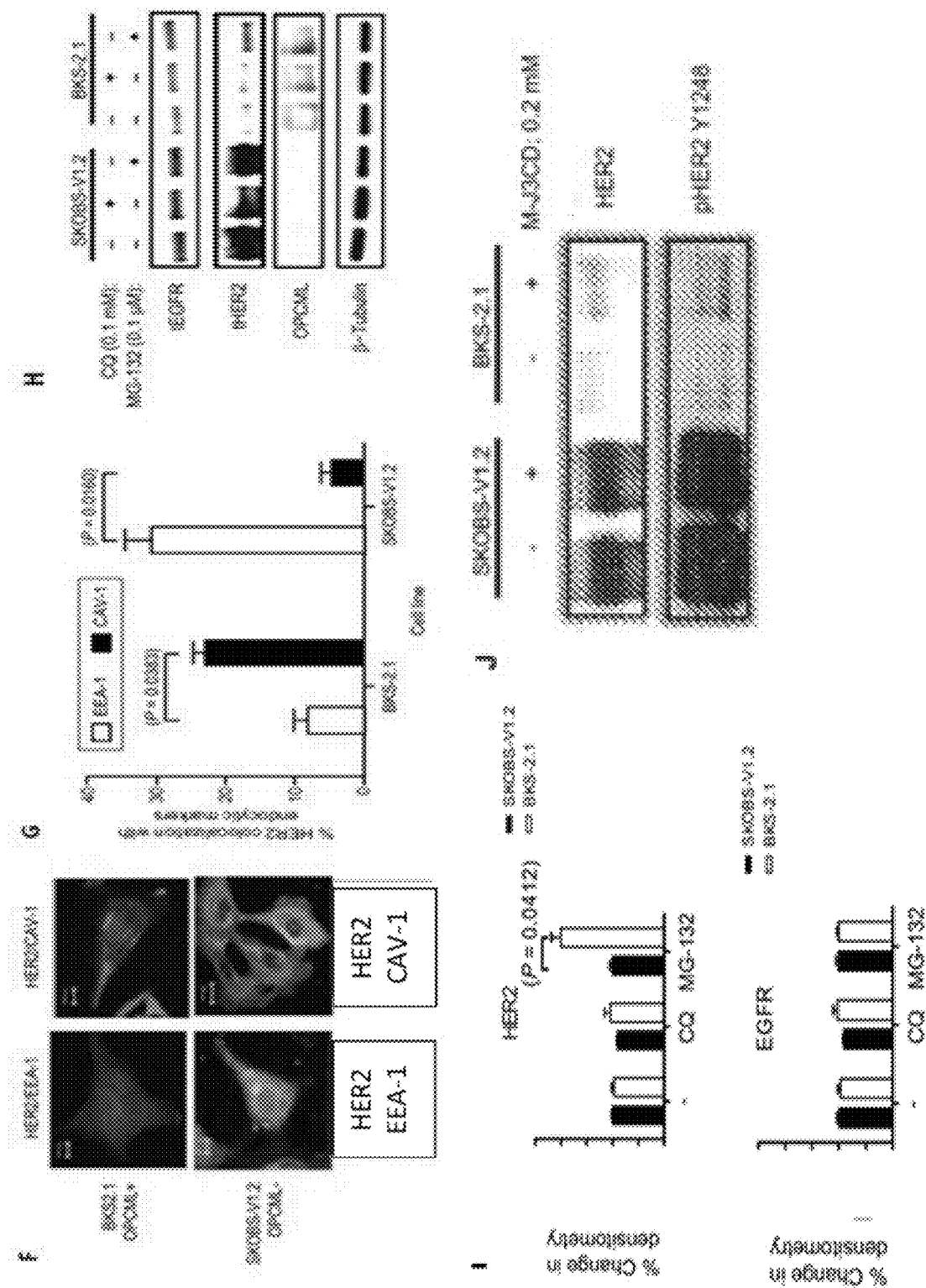

Using HER2 as a paradigm molecule of OPCML-RTK regulation, we found that the available HER2 in OPCML expressing cells was sequestered in the detergent resistant membrane (DRM) fraction. In the OPCML non-expressing line, HER2 was found equally distributed between the DRM and the detergent soluble (non-raft) fractions. The total level of EGFR was not affected by the expression of OPCML and its distribution showed a much less pronounced but discernible shift to the DRM fraction (FIG. 19A). These data indicate that OPCML expression leads to redistribution of HER2 to the DRM fraction in the plasma membrane (that broadly correlates with membrane "rafts"). IFM was employed to examine the trafficking of OPCML in cells; EEA-1 (a marker of the early endosome) and Caveolin-1 (a marker of the raft-caveolar pathway) were used to investigate this apparent redistribution. A decrease in HER2 co-localisation with EEA1 shows that the sequestration of HER2 to the DRM fraction decreases its endocytosis via clathrin-mediated pathways. While an increase in co-localisation with caveolin-1 was observed, the immunofluorescence pattern suggests this is a function of the redistribution of HER2 into the DRM fraction (housing lipid-raft domains) where caveolin is also localised, as HER2 did not appear to be exclusively localised to caveolae in the presence of OPCML expression. Furthermore, in the presence of OPCML the staining was organised into specific sub-cellular particles, suggestive of distinct vesicular compartments (FIGS. 19B&C).

This analysis demonstrated that OPCML expression was associated with increased ubiquitination of HER2 (that binds OPCML), which was strongly increased upon EGF stimulation (FIGS. 19D&E). Exposure to MG-132, a potent inhibitor of the proteasomal 26S proteinase, attenuated HER2 degradation with no such effect on EGFR expression (that does not bind OPCML). In contrast, chloroquine, a weak base that alkalinises the lysosome, showed no inhibition of HER2 degradation (FIGS. 19H&I). This suggested that the proteasomal pathway was preferentially utilised for OPCML-mediated HER2 degradation. Furthermore, disruption of cholesterol (a component of DRM fraction/lipid rafts) using methyl-β-cyclodextrin (Mβ-CD) also inhibited the degradation of HER2 and increased HER2 phosphorylation (FIG. 19J) suggesting that cholesterol-rich lipid-raft structures are important for OPCML-specific internalisation and degradation of HER2.

These findings suggest that OPCML-mediated negative regulation of this specific repertoire of RTKs is the result of direct binding of OPCML to the ECD of that RTK. These multiple but specific binding events result in 'lipid-raft' sequestration, enhanced ubiquitination, and a switch away from clathrin-mediated endocytosis to proteasomal degradation of those specific RTKs negatively regulating their signaling through reducing their protein level. Our data, in the context of very recent publications (Howes et al (2010) *J. Cell Biol.* 190(4): 675-91; Howes et al (2010) *Curr. Opin. Cell Bio.* 22(4): 519-527)), would suggest that CLIC/GEEC bulk internalization route is a strong candidate pathway for OPCML-mediated degradation of HER2 and that this is linked to RTK inactivation and the observable strong tumour suppressor phenotype of OPCML.

Figure 2:
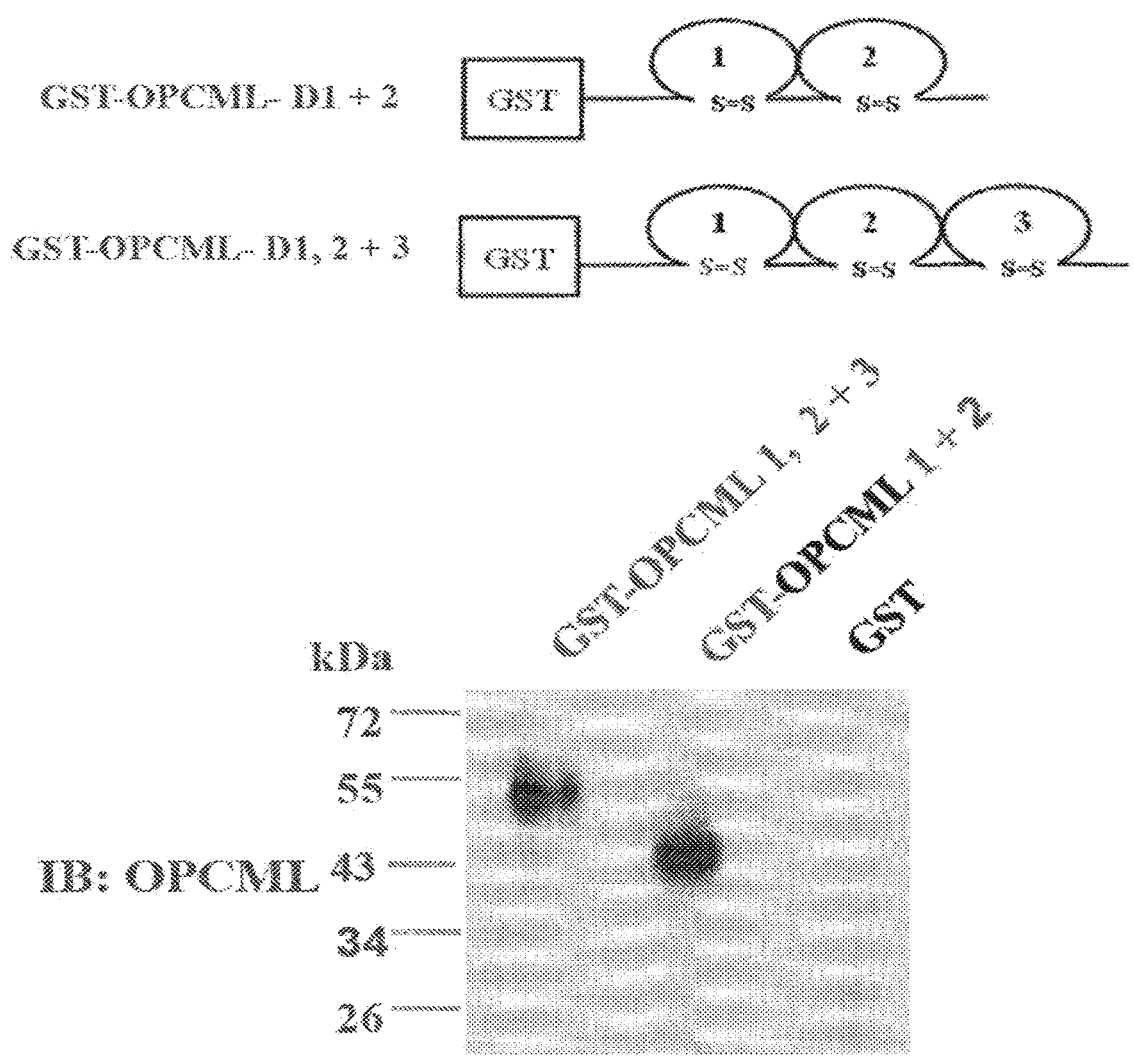
Figure 3:
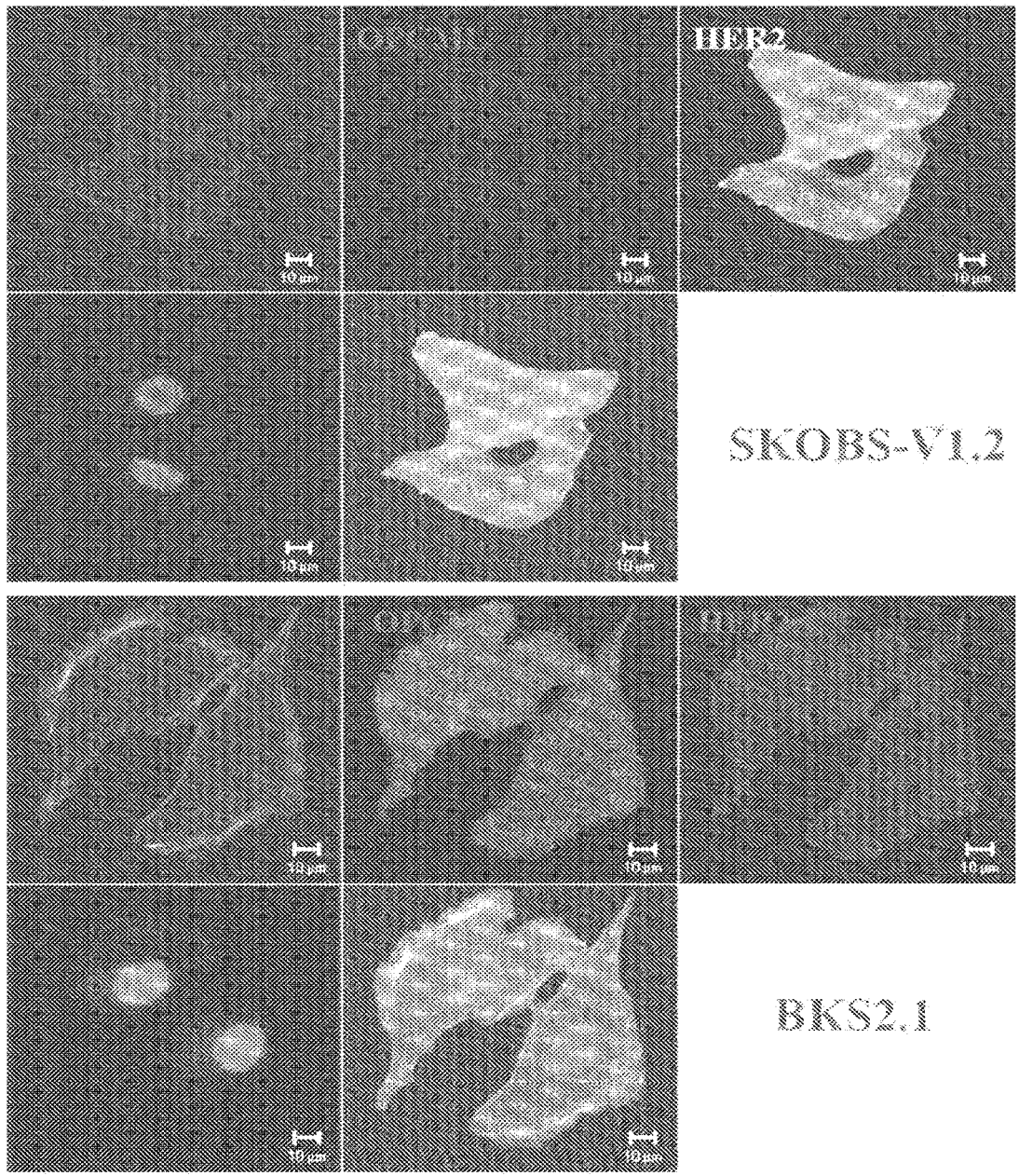
Figure 3:
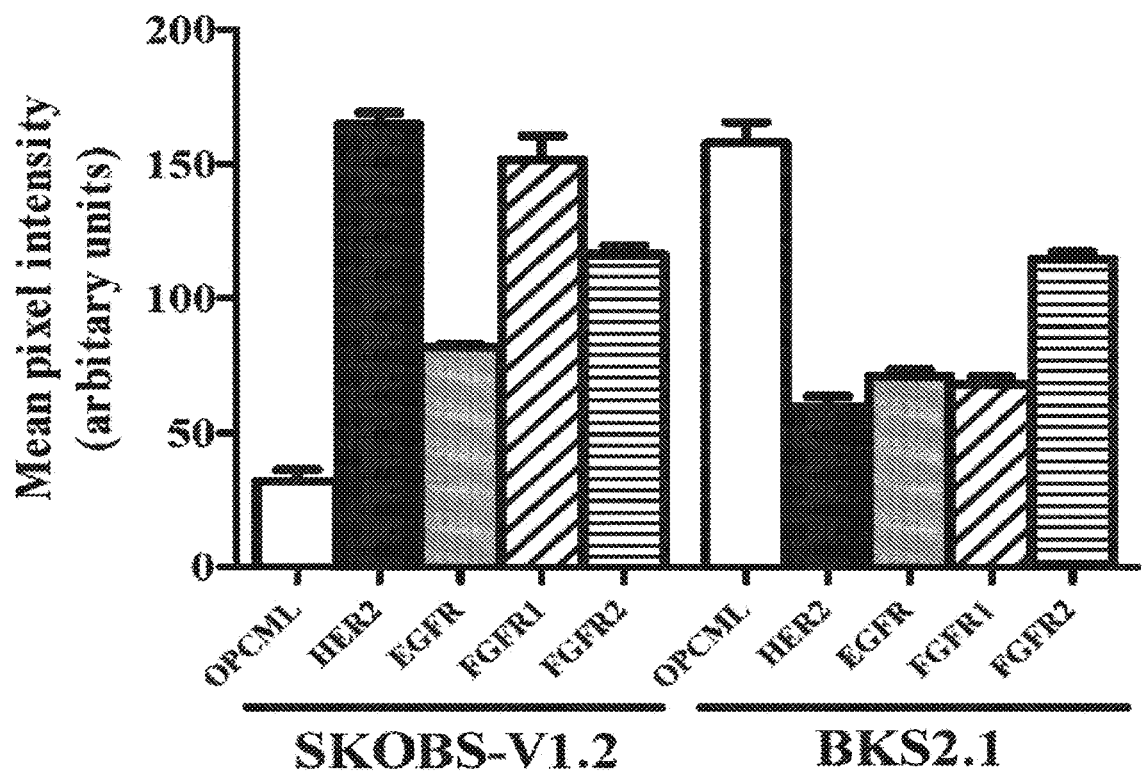
Figure 3:
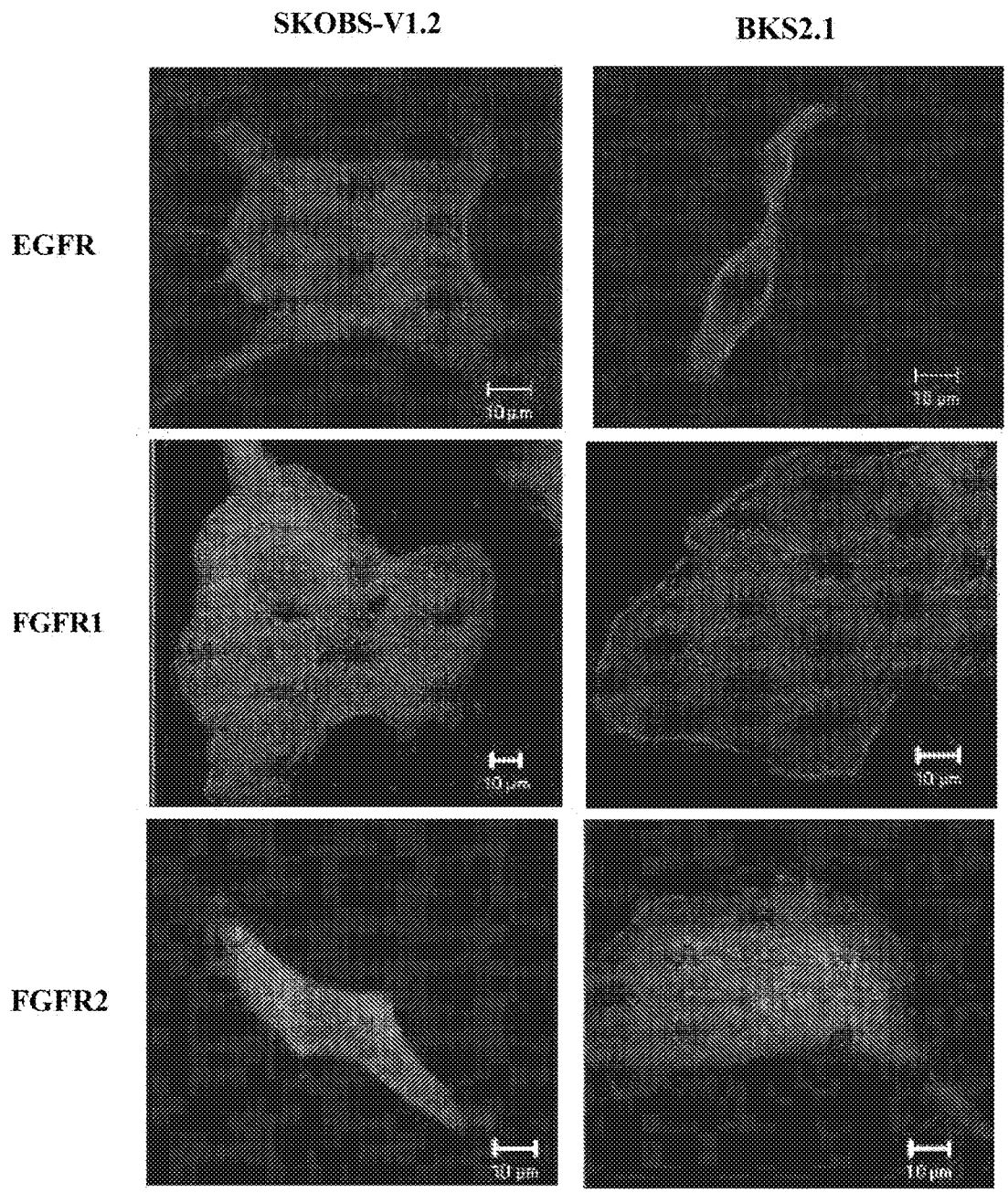
Figure 5:
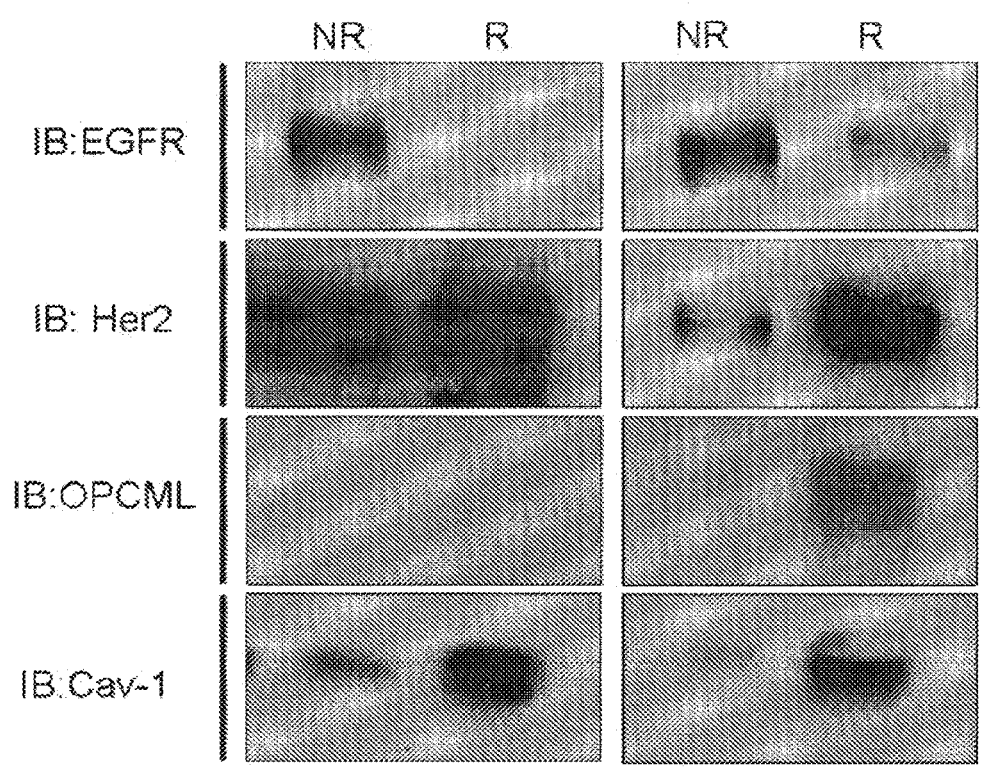
Figure 5:
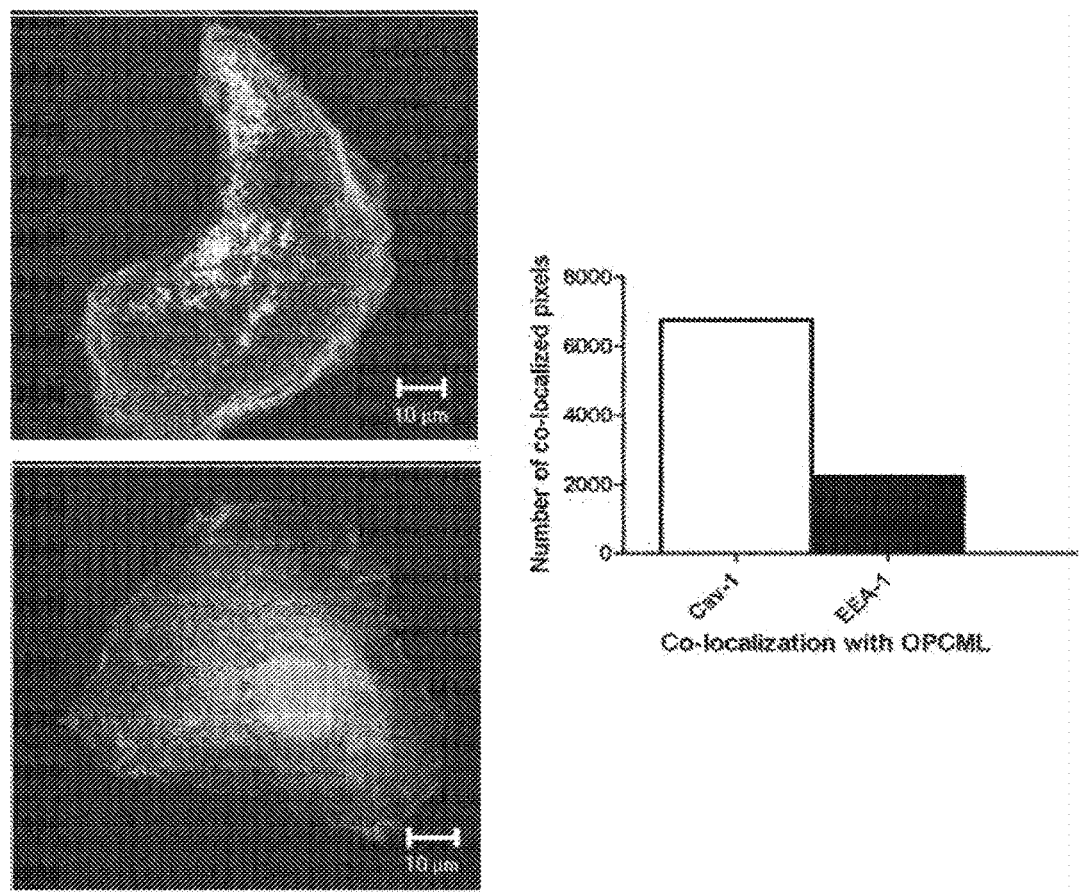
Figure 5:
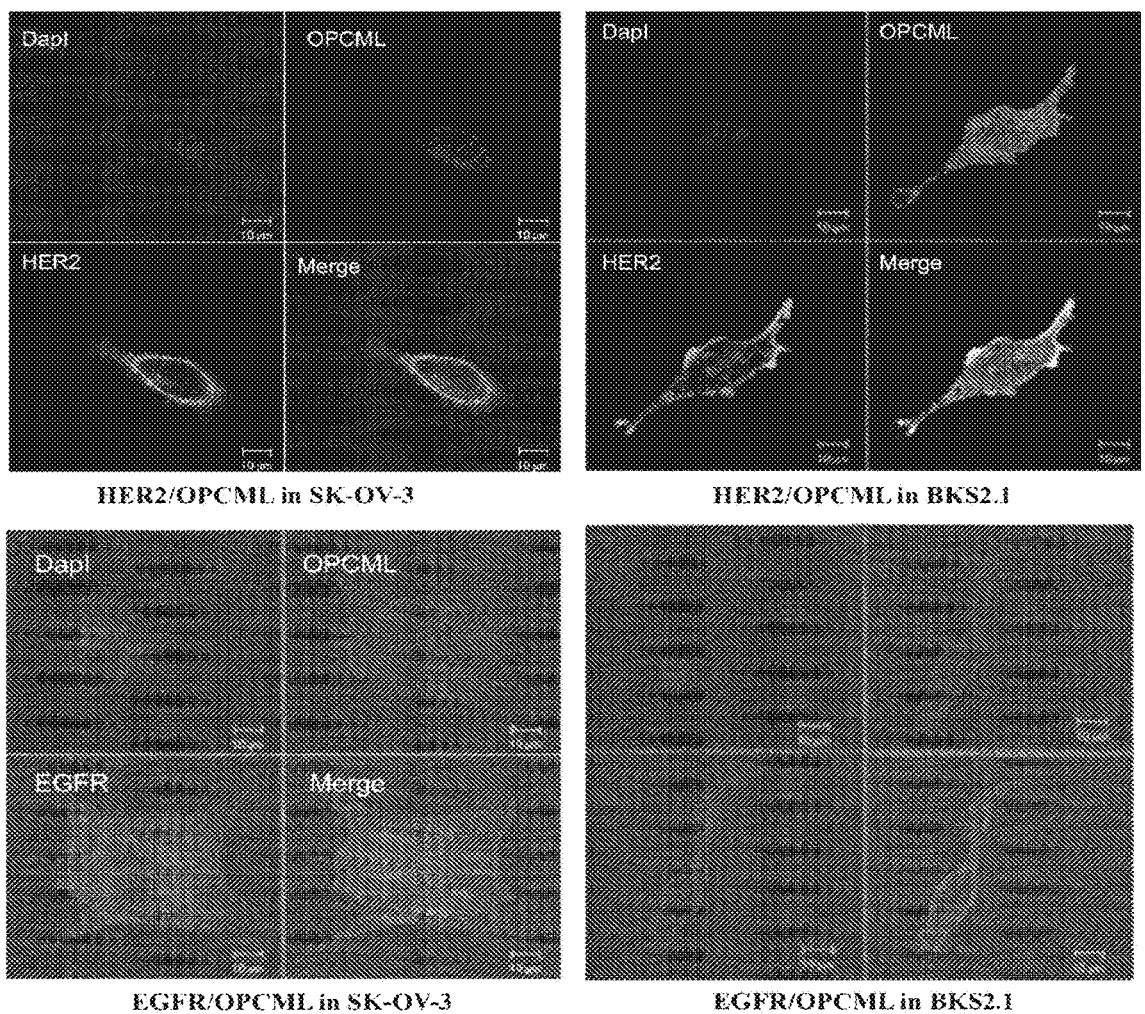
Figure 6:
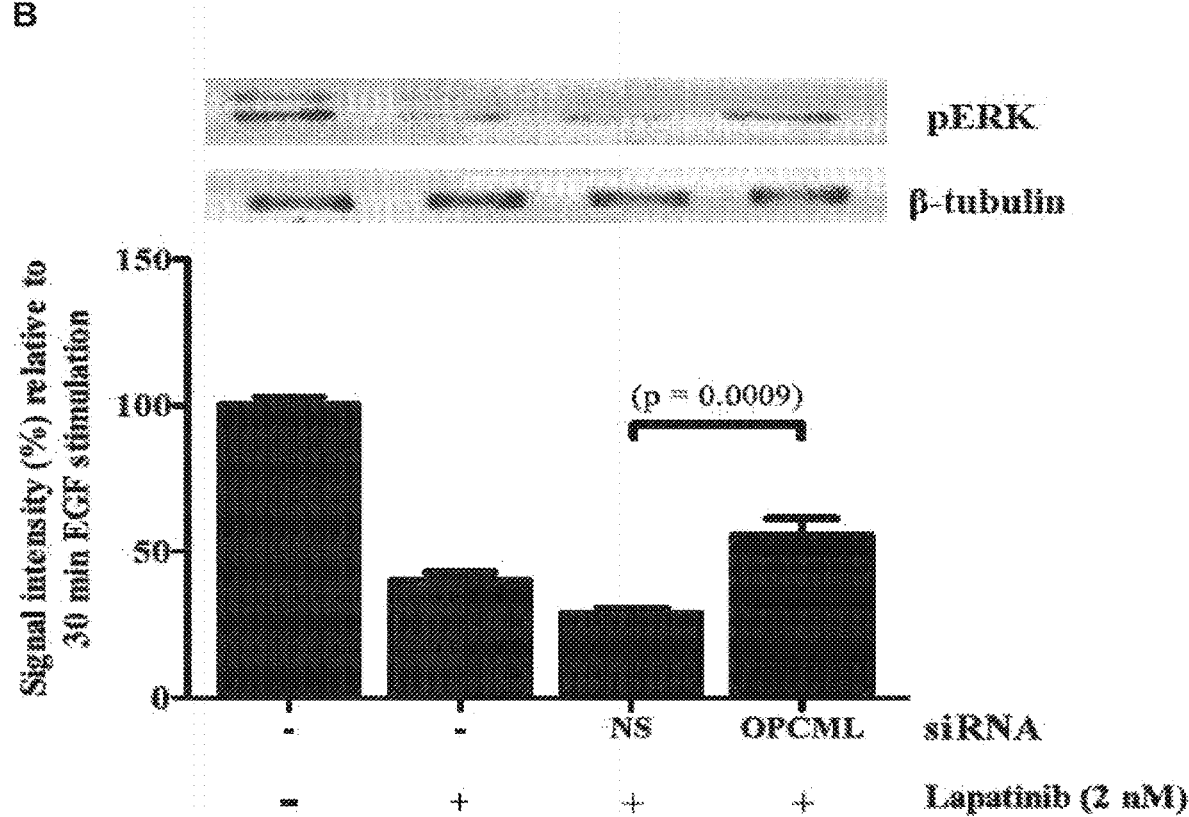
Figure 6:
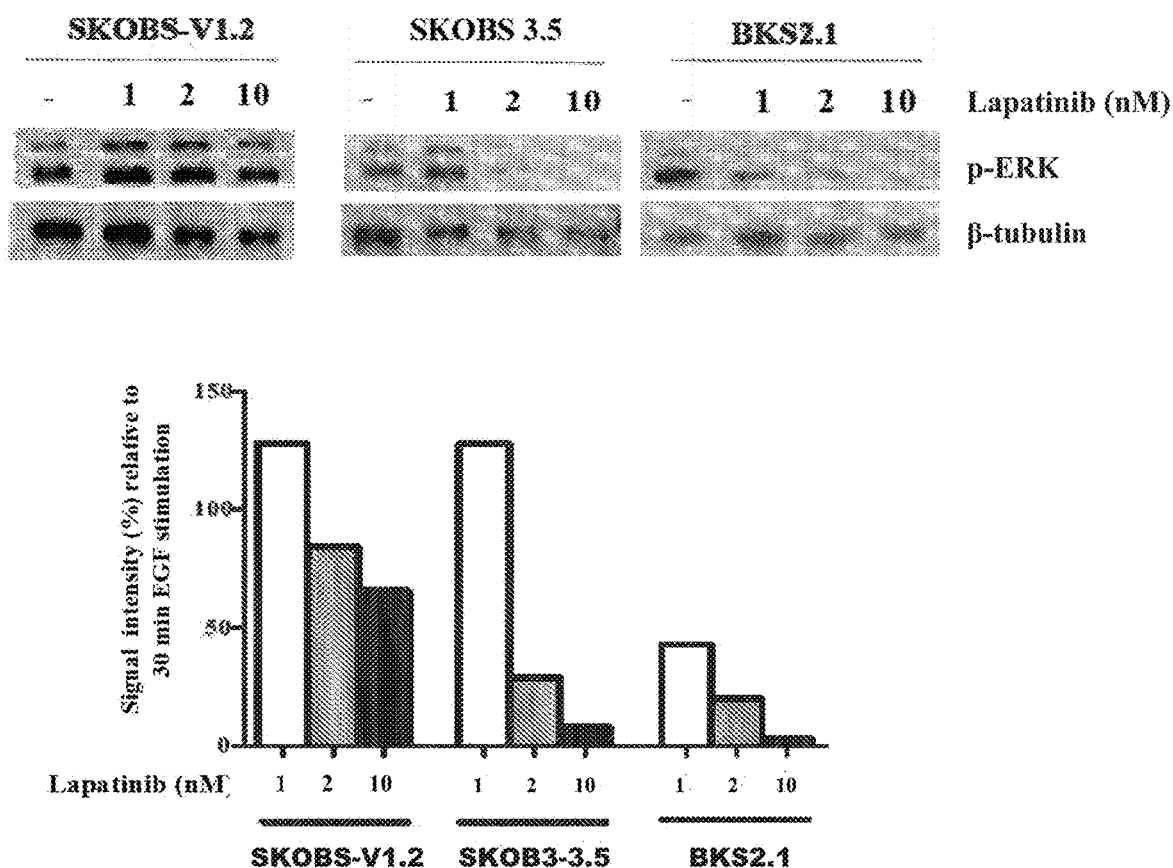
Figure 7:
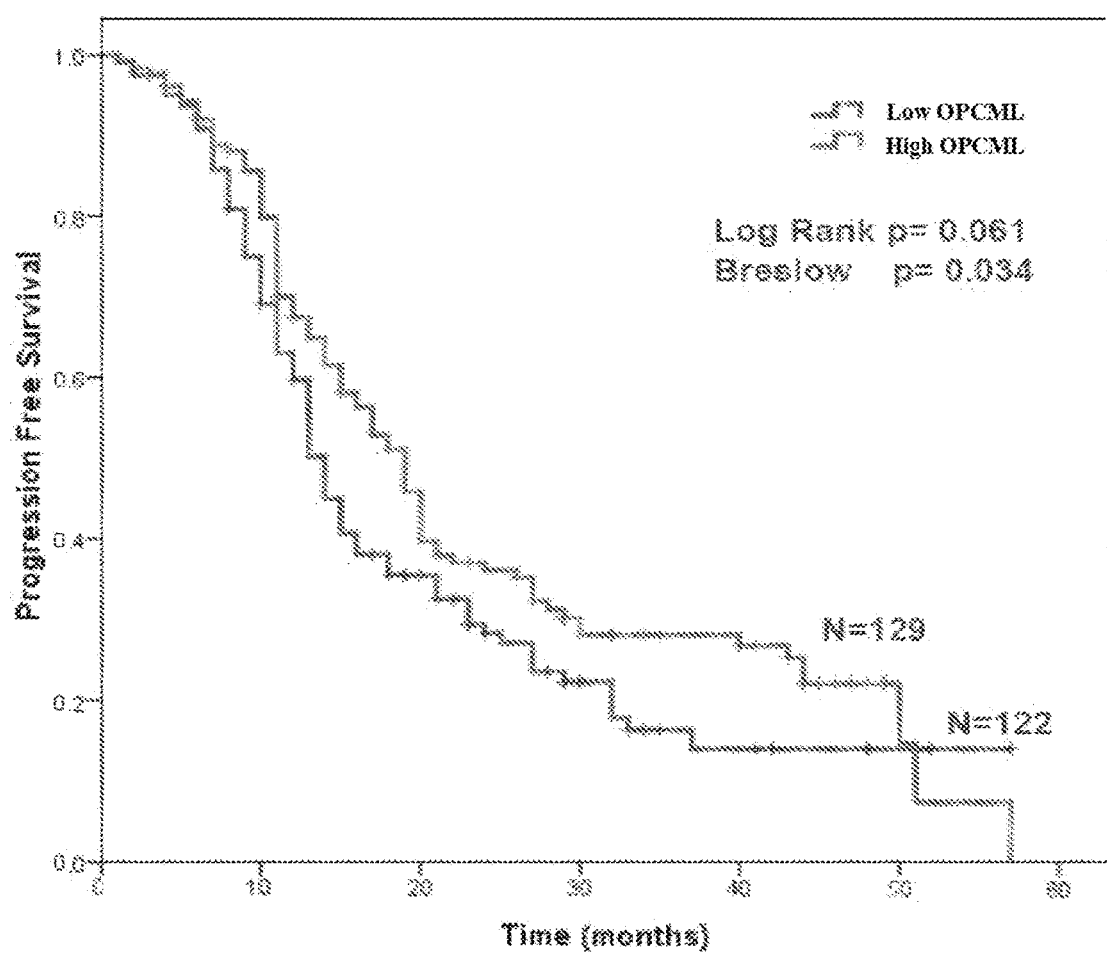
Figure 7:
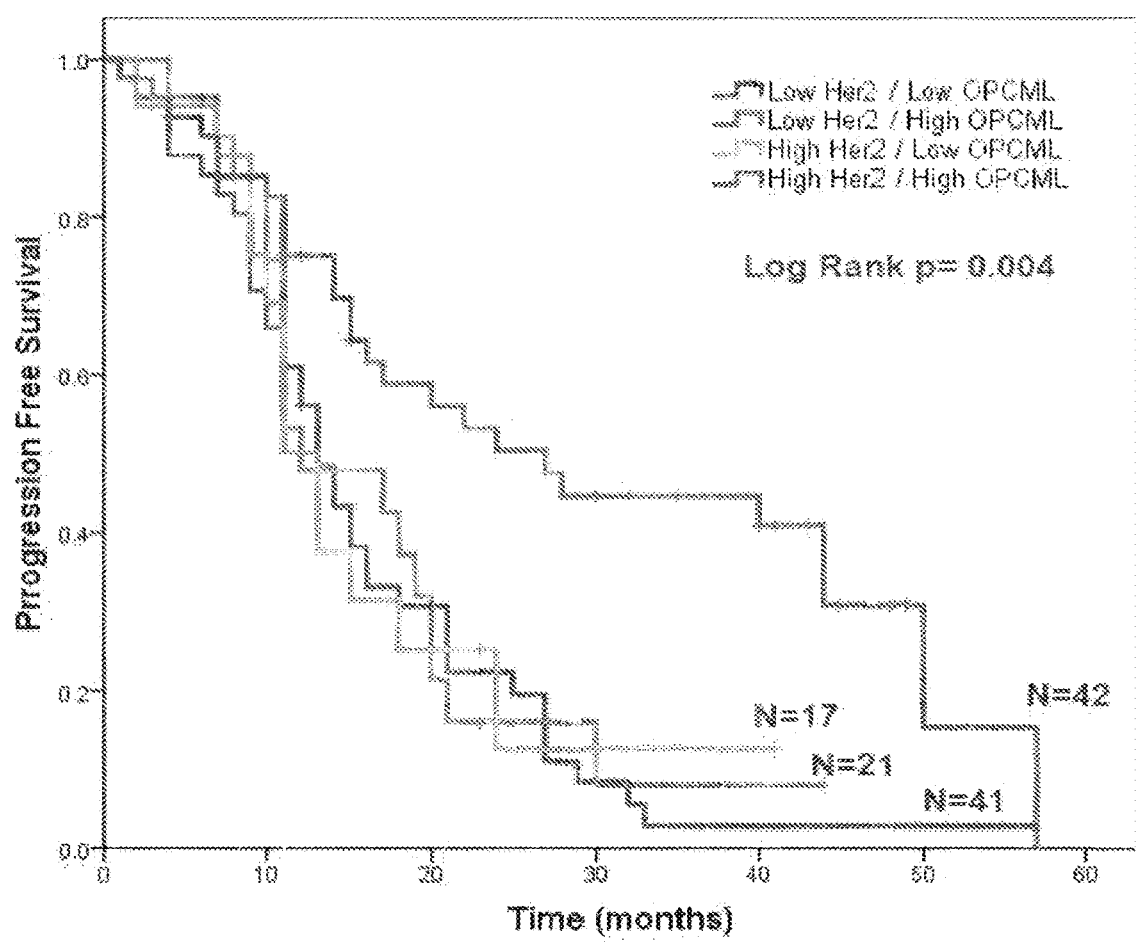
Figure 8:
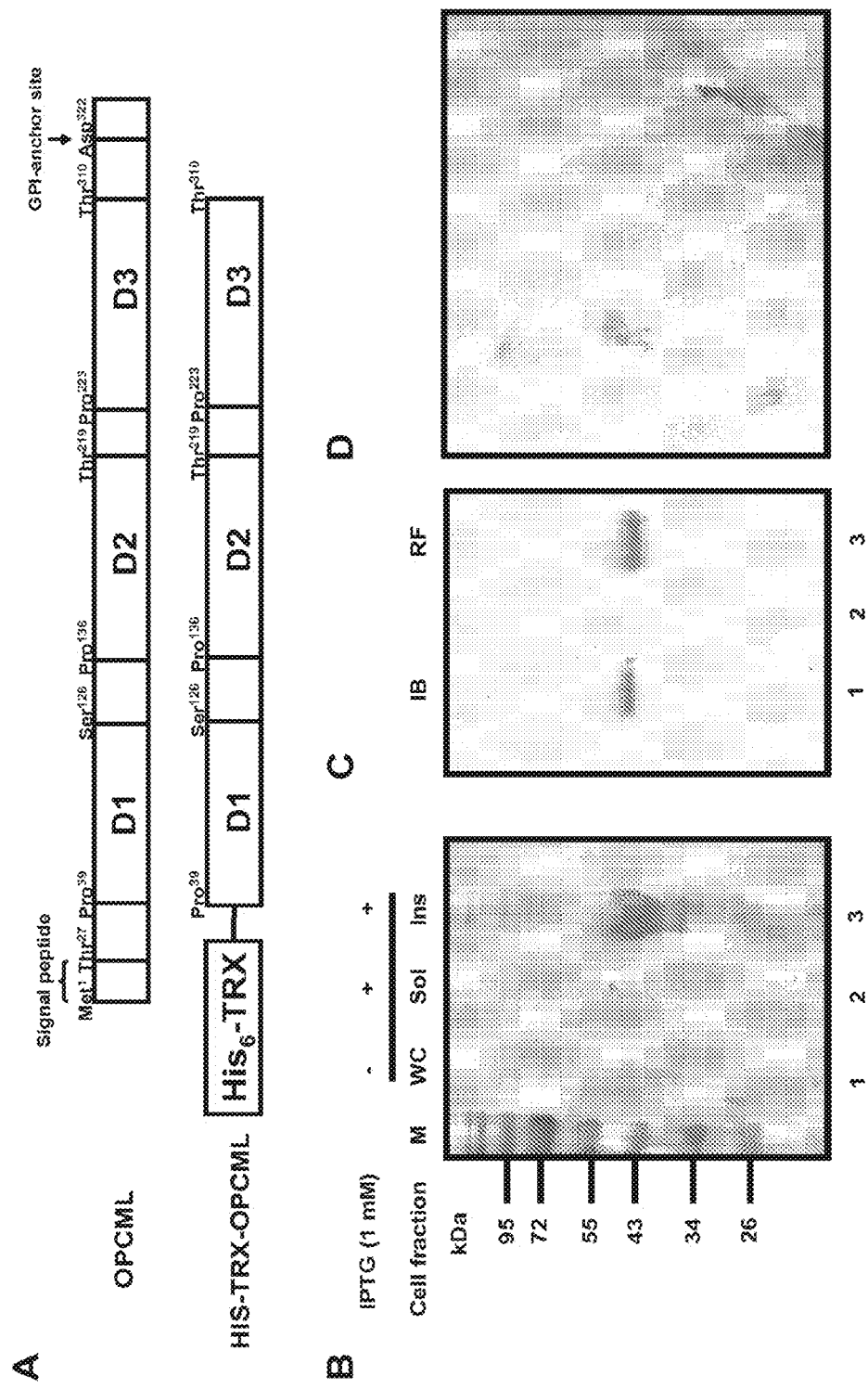
Figure 9:
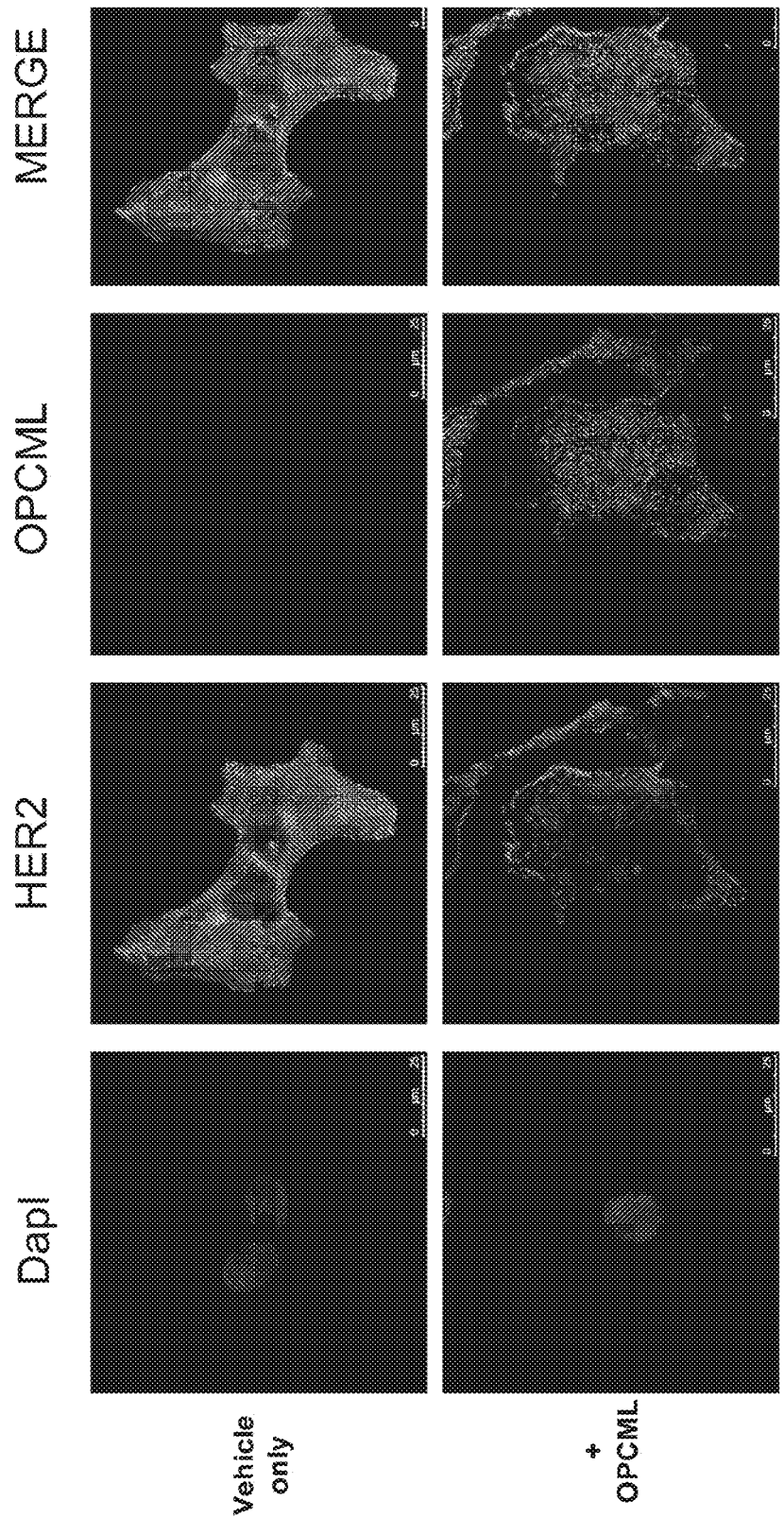
FIG. 9 shows cellular uptake of recombinant OPCML Cells which took up exogenous OPCML demonstrate down-regulation of HER2, as confirmed by IFM.
Figure 10:
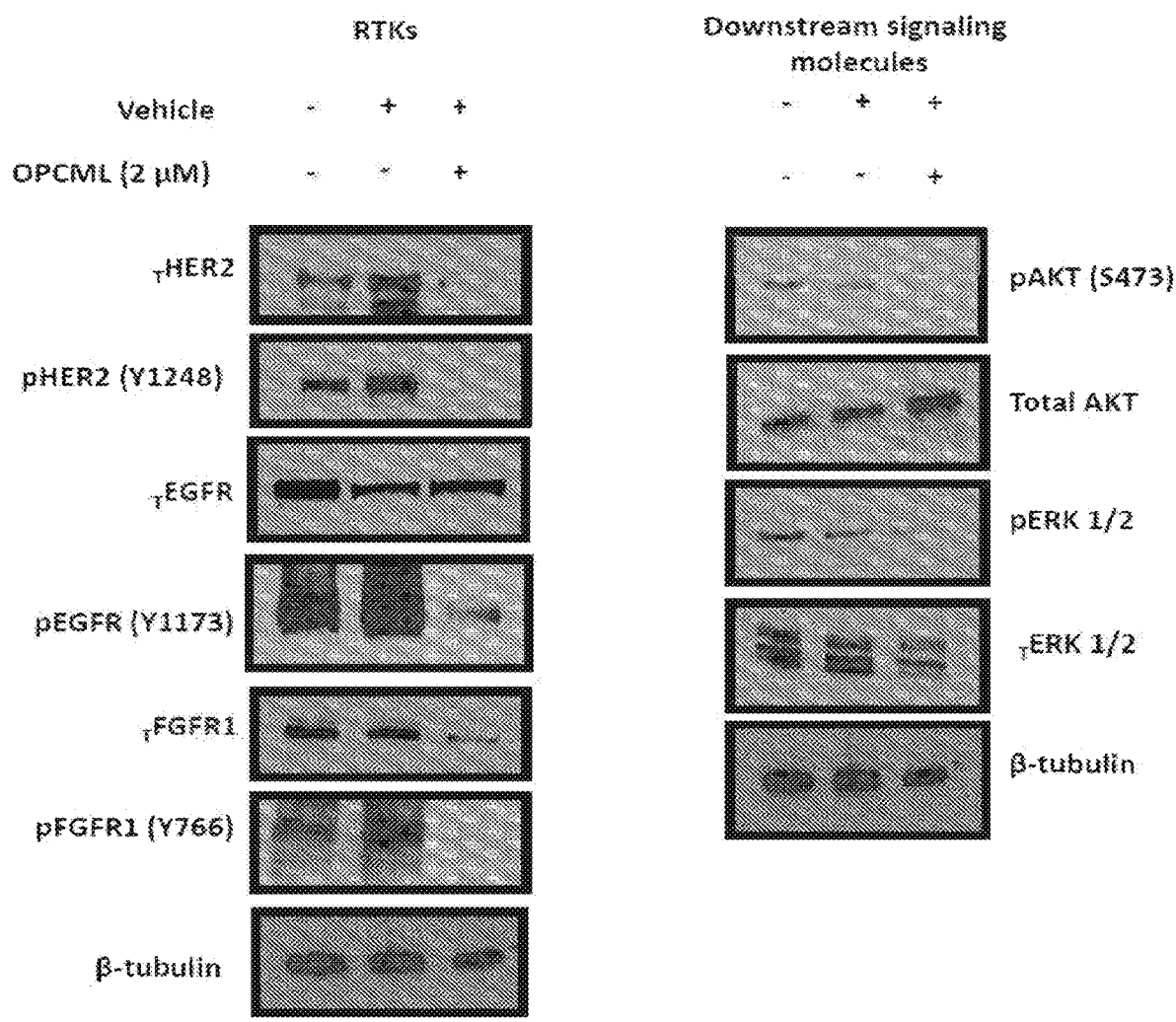
FIG. 10 shows that administration of exogenous OPCML inhibits receptor tyrosine kinase signaling in vitro. Specifically, administration of exogenous OPCML downregulates HER2 and ERK protein levels.
Figure 20:
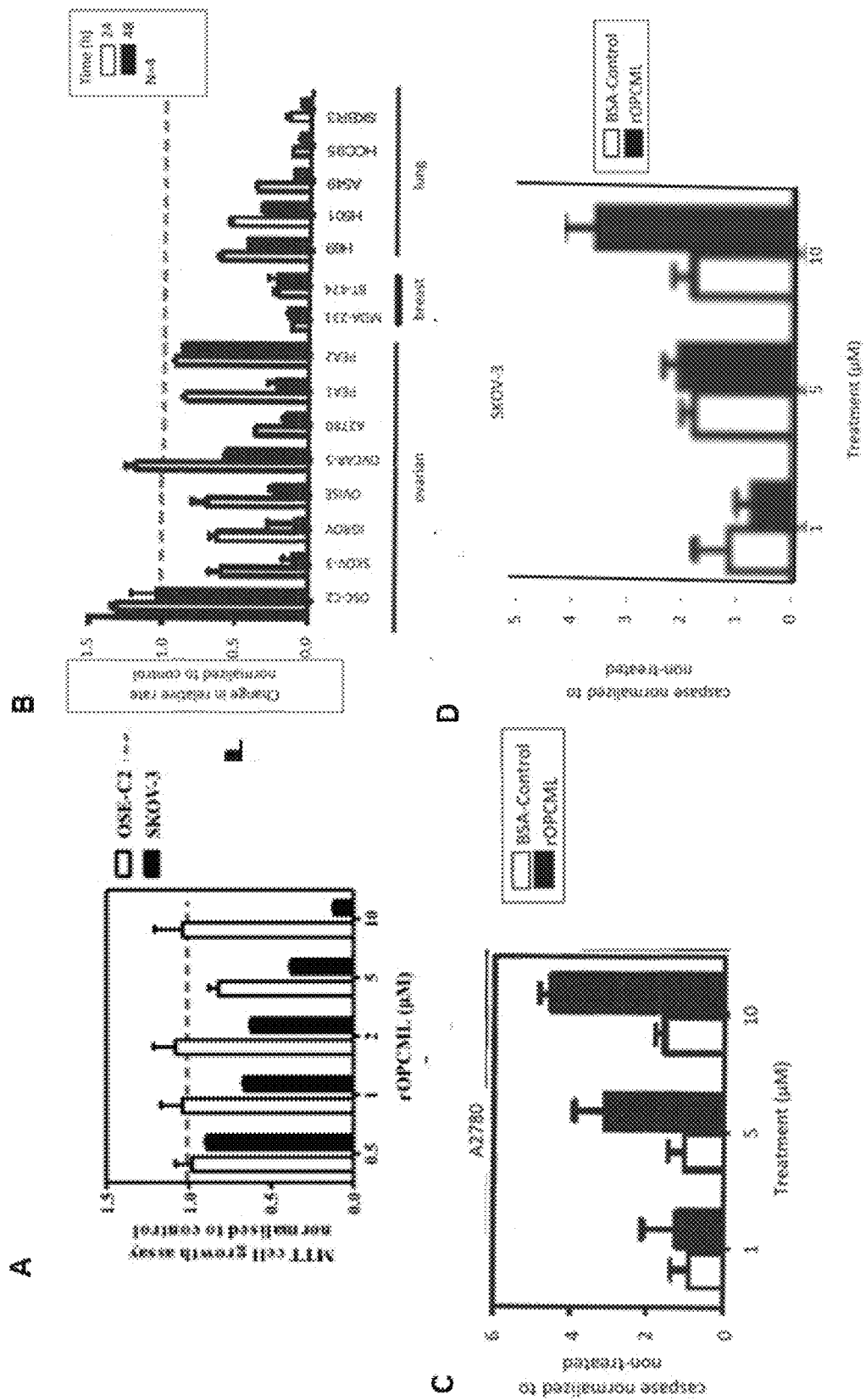
Figure 21:
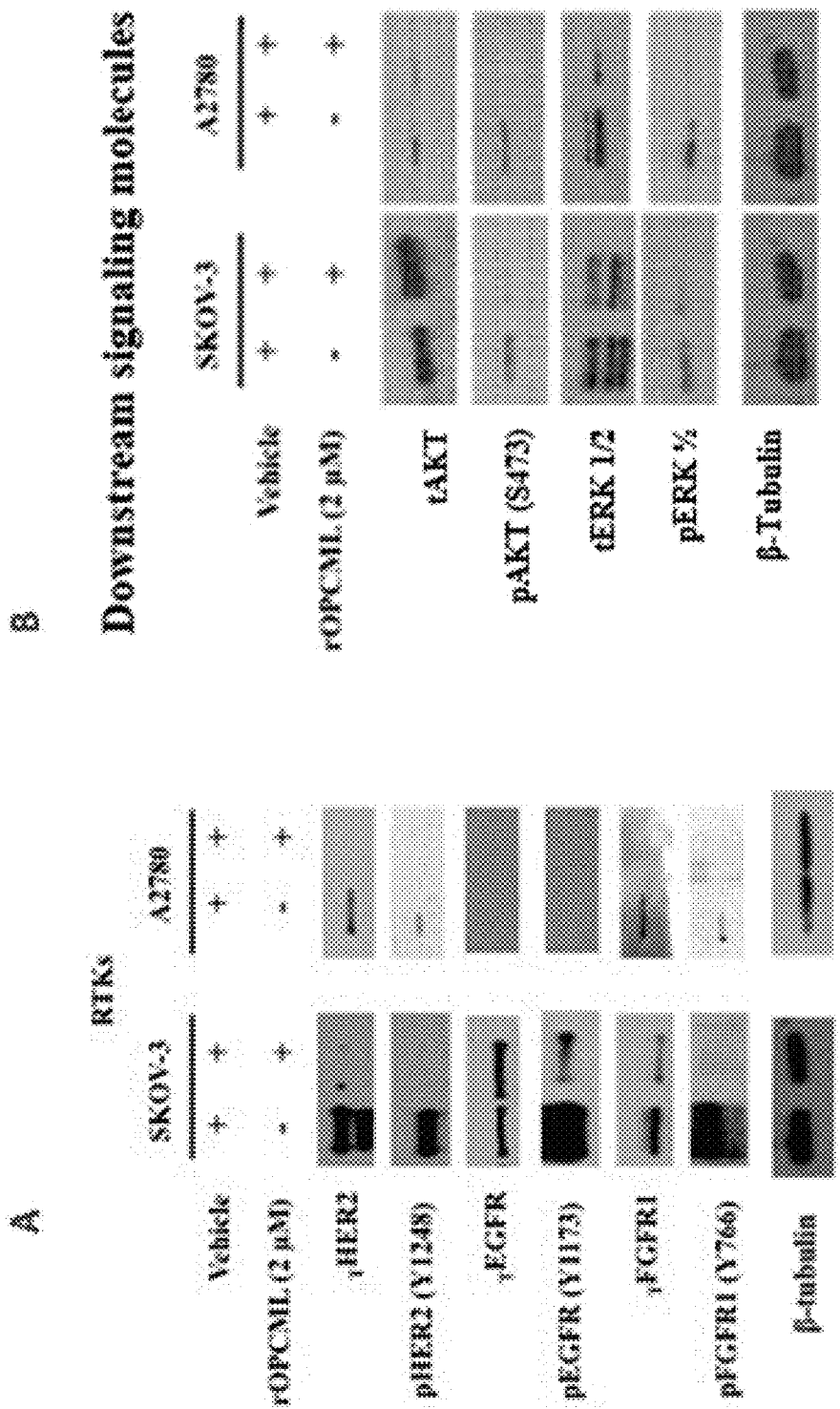

Recombinant OPCML (r-OPCML) inhibits tumour growth in vitro and in vivo Purified recombinant human OPCML domain 1-3 protein (r-OPCML) (FIG. 8) was produced from the bacterial expression vector (pHis-Trx) subcloned with domains 1-3 of OPCML, excluding the signal peptide and GPI anchor sequences (FIG. 8A). Addition of r-OPCML protein to growth media demonstrated a specific, dose-dependent inhibition of cell growth in OPCML non-expressing SKOV-3 ovarian cancer cells, without affecting normal ovarian surface epithelial cells, OSE-C2 (FIG. 20A). We have confirmed that r-OPCML profoundly inhibited cell growth in 6 of 7 additional OPCML non-expressing epithelial ovarian cancer cell lines; 2 of 2 breast HER2-positive and negative cells; and 5 of 5 lung cancer cell lines (FIG. 20B). To determine the mechanism of this pharmacological growth inhibition we performed Annexin V FACS apoptosis assay in SKOV-3 and A2780 demonstrating evidence of early apoptosis induced by r-OPCML at 2-6 hours post exposure depending on cell line (FIG. 20C). We then performed caspase-glo apoptosis assays across a concentration range in SKOV-3 and A2780 ovarian cancer cells and demonstrated that r-OPCML induces apoptosis in both these cell lines in a dose dependent fashion, demonstrating the underlying mechanism of the observed growth inhibition (FIGS. 20D&E). Immunoblotting confirmed that addition of r-OPCML protein to media potently downregulated the same spectrum of RTKs as seen by transfecting OPCML into cancer cells, as well as abrogating pERK and pAKT in both SKOV-3 and A2780 (FIG. 21). This suggests that pharmacological use of extracellular unanchored r-OPCML utilises the same mechanism of action as transfection induced intracellular re-expression of the normal GPI-anchored, glycosylated, OPCML protein. These data were confirmed by IFM for HER2 in SKOV-3, closely mirroring stable transfection of the normal protein in the same cell line (see, FIG. 9).

Figure 22:
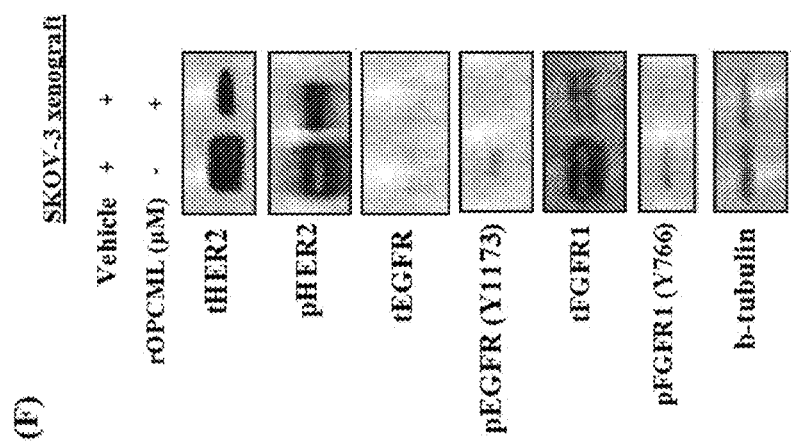

In view of these in-vitro findings, we proceeded to determine whether r-OPCML protein had potential and relevance as an in-vivo tumour suppressor therapy. Mice with either SKOV-3 or A2780 cancer cells injected intraperitoneally (IP), after tumour establishment, received twice-weekly IP injections of either 1 ml (10 μM) bovine serum albumin (BSA) or 1 ml (10 μM) r-OPCML. The experiment was terminated after 3 weeks due to obvious extensive IP tumour growth and deteriorating condition of BSA-treated control animals whereas r-OPCML treated mice remained well (FIG. 22A). r-OPCML significantly and profoundly suppressed both IP tumour growth and ascites formation in-vivo in both IP models (FIG. 22B-D), and in A2780 tumour bearing mice, profoundly inhibited the number of IP peritoneal deposits compared with BSA control (FIG. 22E). Western blotting of SKOV3 IP tumour recovered from BSA treated and r-OPCML treated animals clearly demonstrated the same spectrum of RTKs inhibited as predicted from the in-vitro analysis (FIG. 22F).

CONCLUSION

OPCML mediates its tumour suppressor function by systems level negative regulation of at least 5 RTKs and a recombinant modified OPCML derivative is a potent tumor suppressor protein therapeutic in-vitro and in-vivo.

The invention claimed is:

1. A method of tumor suppressor protein therapy comprising administering to a patient in need thereof or a tumor of a patient in need thereof an effective amount of a polypeptide comprising a fragment of OPCML consisting of residues 39-219 of human OPCML (SEQ ID NO:1) or residues 39-310 of human OPCML (SEQ ID NO: 1), wherein the fragment lacks OPCML signal sequence residues.

2. The method according to claim 1, wherein the tumor is a HER2-positive (HER2+) cancer tumor.

3. The method according to claim 1, wherein the tumor is a HER2-negative (HER2) cancer tumor.

4. The method according to claim 1, wherein the OPCML fragment is fused to a fusion partner.

5. The method according to claim 4, wherein the fusion partner is a non-OPCML polypeptide.

6. The method according to claim 4, wherein the fusion partner is fragment of human serum albumin that is the human serum albumin signal peptide.

7. The method according to claim 4, wherein the fusion partner is an antibody Fc fragment.

8. The method according to claim 1, wherein the OPCML fragment is isolated from a eukaryotic expression system.

9. The method according to claim 8, wherein the eukaryotic expression system is a mammalian cell line expression system.

10. The method according to claim 8, wherein the eukaryotic expression system is a Chinese hamster ovary (CHO) cell line expression system.

11. The method according to claim 1, wherein the OPCML fragment is isolated from a prokaryotic expression system.

12. The method according to claim 11, wherein the prokaryotic expression system is an *E. coli* expression system.

13. The method according to claim 1, wherein the OPCML fragment is administered intravenously.

14. The method according to claim 1, wherein the OPCML fragment is administered intraperitoneally.

15. The method according to claim 1, wherein the OPCML fragment is administered topically.

16. The method according to claim 1, wherein the OPCML fragment is administered orally, buccally, or sublingually.

17. The method according to claim 1, wherein the OPCML fragment is administered via catheter or stent.

18. The method according to claim 2, wherein the cancer is selected from the group consisting of ovarian cancer, breast cancer, renal cancer, gastrointestinal cancer, brain cancer, lung cancer, nasopharyngeal cancer, esophageal cancer, gastric cancer, colon cancer, liver cancer, cervical cancer, prostate cancer, non-Hodgkin lymphoma, Hodgkin lymphoma, and nasal NK/T-cell lymphoma.

19. The method according to claim 18, wherein the cancer is breast cancer.

20. The method according to claim 18, wherein the cancer is ovarian cancer.

* * * * *